US012465748B2

(12) United States Patent
Calomeni et al.

(10) Patent No.: US 12,465,748 B2
(45) Date of Patent: Nov. 11, 2025

(54) CATHETER BLOOD PUMPS AND COLLAPSIBLE PUMP HOUSINGS

(71) Applicant: Shifamed Holdings, LLC, Campbell, CA (US)

(72) Inventors: Michael Calomeni, San Jose, CA (US); Brian D. Brandt, Morgan Hill, CA (US); Daniel Hildebrand, Santa Cruz, CA (US); Gregory Michael Hamel, Redwood City, CA (US)

(73) Assignee: Supira Medical, Inc., Los Gatos, CA (US)

( * ) Notice: Subject to any disclaimer, the term of this patent is extended or adjusted under 35 U.S.C. 154(b) by 168 days.

(21) Appl. No.: 16/988,221

(22) Filed: Aug. 7, 2020

(65) Prior Publication Data

US 2021/0038786 A1 Feb. 11, 2021

Related U.S. Application Data

(60) Provisional application No. 62/884,089, filed on Aug. 7, 2019.

(51) Int. Cl.

| | |
|---|---|
| ***A61M 60/808*** | (2021.01) |
| ***A61M 60/13*** | (2021.01) |
| ***A61M 60/135*** | (2021.01) |

(52) U.S. Cl.
CPC .......... *A61M 60/808* (2021.01); *A61M 60/13* (2021.01); *A61M 60/135* (2021.01)

(58) Field of Classification Search
CPC .. A61M 60/808; A61M 60/13; A61M 60/135; A61M 60/237; A61M 60/414; A61M 60/804; A61M 60/806; A61M 60/81; A61M 60/857
See application file for complete search history.

(56) References Cited

U.S. PATENT DOCUMENTS

| | | | |
|---|---|---|---|
| 1,061,107 | A | 5/1913 | Nordmark |
| 1,596,933 | A | 8/1926 | Kister |
| 3,152,618 | A | 10/1964 | Rothermel et al. |
| 3,175,555 | A | 3/1965 | Ling |
| 3,178,833 | A | 4/1965 | Gulbransen, Jr. |
| 3,208,448 | A | 9/1965 | Woodward |
| 3,233,609 | A | 2/1966 | Leucci |
| 3,421,497 | A | 1/1969 | Chesnut |

(Continued)

FOREIGN PATENT DOCUMENTS

| | | | |
|---|---|---|---|
| CA | 2352234 | A1 | 6/2000 |
| CA | 2739899 | C | 5/2017 |

(Continued)

OTHER PUBLICATIONS

Ryan et al.; U.S. Appl. No. 17/782,675 entitled "Intravascular blood pumps, motors, and fluid control," filed Jun. 6, 2022.

(Continued)

*Primary Examiner* — Catherine M Voorhees
(74) *Attorney, Agent, or Firm* — Shay Glenn LLP

(57) ABSTRACT

Catheter blood pumps that include an expandable pump portion. The pump portions include an collapsible blood conduit that defines a blood lumen. The collapsible blood conduits include a collapsible scaffold adapted to provide radial support to the blood conduit. The pump portion also includes one or more impellers.

21 Claims, 28 Drawing Sheets

(56) References Cited

U.S. PATENT DOCUMENTS 3,502,412 A 3/1970 Burns
3,504,662 A 4/1970 Jones
3,505,987 A 4/1970 Heilman
3,568,659 A 3/1971 Karnegis
3,693,612 A 9/1972 Donahoe et al.
3,734,648 A 5/1973 Nielson
3,774,243 A 11/1973 Ng et al.
3,837,922 A 9/1974 Ng et al.
3,841,837 A 10/1974 Kitrilakis et al.
3,860,968 A 1/1975 Shapiro
3,919,722 A 11/1975 Harmison
4,015,590 A 4/1977 Normann
4,037,984 A 7/1977 Rafferty et al.
4,046,137 A 9/1977 Curless et al.
4,058,857 A 11/1977 Runge et al.
4,093,726 A 6/1978 Winn et al.
4,135,253 A 1/1979 Reich et al.
4,142,845 A 3/1979 Lepp et al.
4,173,796 A 11/1979 Jarvik
4,190,047 A 2/1980 Jacobsen et al.
4,255,821 A 3/1981 Carol et al.
4,289,141 A 9/1981 Cormier
4,310,930 A 1/1982 Goldowsky
4,311,133 A 1/1982 Robinson
4,328,806 A 5/1982 Cooper
4,370,983 A 2/1983 Lichtenstein
4,381,005 A 4/1983 Bujan
4,381,567 A 5/1983 Robinson et al.
4,382,199 A 5/1983 Isaacson
4,389,737 A 6/1983 Robinson et al.
4,397,049 A 8/1983 Robinson et al.
4,407,304 A 10/1983 Lieber et al.
4,506,658 A 3/1985 Casile
4,515,589 A 5/1985 Austin et al.
4,522,195 A 6/1985 Schiff
4,524,466 A 6/1985 Hall et al.
4,551,073 A 11/1985 Schwab
4,576,606 A 3/1986 Pol et al.
4,585,004 A 4/1986 Brownlee
4,585,007 A 4/1986 Uchigaki et al.
4,599,081 A 7/1986 Cohen
4,600,405 A 7/1986 Zibelin
4,623,350 A 11/1986 Lapeyre et al.
4,625,712 A 12/1986 Wampler
4,652,265 A 3/1987 McDougall
4,662,358 A 5/1987 Farrar et al.
4,666,598 A 5/1987 Heath et al.
4,675,361 A 6/1987 Ward
4,685,910 A 8/1987 Schweizer
4,726,379 A 2/1988 Altman et al.
4,753,221 A 6/1988 Kensey et al.
4,767,289 A 8/1988 Parrott et al.
4,771,777 A 9/1988 Horzewski et al.
4,779,614 A 10/1988 Moise
4,782,817 A 11/1988 Singh et al.
4,785,795 A 11/1988 Singh
4,802,650 A 2/1989 Stricker
4,818,186 A 4/1989 Pastrone et al.
4,826,481 A 5/1989 Sacks et al.
4,846,152 A 7/1989 Wampler et al.
4,846,831 A 7/1989 Skillin
4,850,957 A 7/1989 Summers
4,888,009 A 12/1989 Lederman et al.
4,888,011 A 12/1989 Kung et al.
4,902,272 A 2/1990 Milder et al.
4,907,592 A 3/1990 Harper
4,908,012 A 3/1990 Moise et al.
4,919,647 A 4/1990 Nash
4,936,759 A 6/1990 Clausen et al.
4,961,738 A 10/1990 Mackin
4,976,683 A 12/1990 Gauthier et al.
4,995,857 A 2/1991 Arnold
5,026,367 A 6/1991 Leckrone et al.
D318,113 S 7/1991 Moutafis et al.
5,045,051 A 9/1991 Milder et al.
5,046,503 A 9/1991 Schneiderman
5,047,147 A 9/1991 Chevallet et al.
5,049,134 A 9/1991 Golding et al.
5,061,256 A 10/1991 Wampler
5,084,064 A 1/1992 Barak et al.
5,089,016 A 2/1992 Millner et al.
5,090,957 A 2/1992 Moutafis et al.
5,092,844 A 3/1992 Schwartz et al.
5,092,879 A 3/1992 Jarvik
5,112,200 A 5/1992 Isaacson et al.
5,112,292 A 5/1992 Hwang et al.
5,114,399 A 5/1992 Kovalcheck
5,116,305 A 5/1992 Milder et al.
5,139,517 A 8/1992 Corral
5,145,333 A 9/1992 Smith
5,147,281 A 9/1992 Thornton et al.
5,171,264 A 12/1992 Merrill
5,180,378 A 1/1993 Kung et al.
5,192,314 A 3/1993 Daskalakis
5,200,050 A 4/1993 Ivory et al.
5,205,721 A 4/1993 Isaacson
5,211,546 A 5/1993 Isaacson et al.
5,261,411 A 11/1993 Hughes
5,270,005 A 12/1993 Raible
5,287,858 A 2/1994 Hammerslag et al.
5,300,111 A 4/1994 Panton et al.
5,300,112 A 4/1994 Barr
5,314,418 A 5/1994 Takano et al.
5,322,413 A 6/1994 Vescovini et al.
5,326,344 A 7/1994 Bramm et al.
5,363,856 A 11/1994 Hughes et al.
5,397,349 A 3/1995 Kolff et al.
5,399,074 A 3/1995 Nose et al.
5,405,251 A 4/1995 Sipin
5,441,636 A 8/1995 Chevallet et al.
5,443,504 A 8/1995 Hill
5,486,192 A 1/1996 Walinsky et al.
5,487,727 A 1/1996 Snider et al.
5,507,629 A 4/1996 Jarvik
5,507,795 A 4/1996 Chiang et al.
5,510,267 A 4/1996 Marshall
5,512,042 A 4/1996 Montoya et al.
5,531,789 A 7/1996 Yamazaki et al.
5,628,731 A 5/1997 Dodge et al.
5,630,835 A 5/1997 Brownlee
5,643,172 A 7/1997 Kung et al.
5,643,215 A 7/1997 Fuhrman et al.
5,653,696 A 8/1997 Shiber
5,662,643 A 9/1997 Kung et al.
5,676,526 A 10/1997 Kuwana et al.
5,683,231 A 11/1997 Nakazawa et al.
5,702,365 A 12/1997 King
5,713,730 A 2/1998 Nose et al.
5,735,892 A 4/1998 Myers et al.
5,749,839 A 5/1998 Kovacs
5,751,125 A 5/1998 Weiss
5,759,148 A 6/1998 Sipin
5,766,207 A 6/1998 Potter et al.
5,776,096 A 7/1998 Fields
5,800,138 A 9/1998 Merce Vives
5,800,457 A 9/1998 Gelbfish
5,803,720 A 9/1998 Ohara et al.
5,814,076 A 9/1998 Brownlee
5,814,102 A 9/1998 Guldner et al.
5,851,174 A 12/1998 Jarvik et al.
5,888,241 A 3/1999 Jarvik
5,906,579 A 5/1999 Vander Salm et al.
5,910,124 A 6/1999 Rubin
5,919,369 A 7/1999 Ash
5,941,813 A 8/1999 Sievers et al.
5,957,672 A 9/1999 Aber
5,964,694 A 10/1999 Siess et al.
5,984,893 A 11/1999 Ward
6,007,478 A 12/1999 Siess et al.
6,013,058 A 1/2000 Prosl et al.
6,022,363 A 2/2000 Walker et al.
6,030,336 A 2/2000 Franchi
6,042,347 A 3/2000 Scholl et al.
6,053,943 A 4/2000 Edwin et al.

(56) References Cited

U.S. PATENT DOCUMENTS

| | | | |
|---|---|---|---|
| 6,066,085 | A | 5/2000 | Heilman et al. |
| 6,066,152 | A | 5/2000 | Strauss et al. |
| 6,068,588 | A | 5/2000 | Goldowsky |
| 6,071,093 | A | 6/2000 | Hart |
| 6,071,258 | A | 6/2000 | Dalke et al. |
| 6,082,105 | A | 7/2000 | Miyata |
| 6,101,406 | A | 8/2000 | Hacker et al. |
| 6,106,509 | A | 8/2000 | Loubser |
| 6,113,536 | A | 9/2000 | Aboul Hosn et al. |
| 6,117,130 | A | 9/2000 | Kung |
| 6,117,390 | A | 9/2000 | Corey |
| 6,120,537 | A | 9/2000 | Wampler |
| 6,123,659 | A | 9/2000 | Le Blanc et al. |
| 6,123,726 | A | 9/2000 | Mori et al. |
| 6,129,660 | A | 10/2000 | Nakazeki et al. |
| 6,136,025 | A | 10/2000 | Barbut et al. |
| 6,139,487 | A | 10/2000 | Siess |
| 6,142,752 | A | 11/2000 | Akamatsu et al. |
| 6,146,771 | A | 11/2000 | Wirt et al. |
| 6,149,683 | A | 11/2000 | Lancisi et al. |
| 6,152,704 | A | 11/2000 | Aboul Hosn et al. |
| 6,155,969 | A | 12/2000 | Schima et al. |
| 6,176,848 | B1 | 1/2001 | Rau et al. |
| 6,180,058 | B1 | 1/2001 | Lindsay |
| 6,197,055 | B1 | 3/2001 | Matthews |
| 6,197,289 | B1 | 3/2001 | Wirt et al. |
| 6,210,133 | B1 | 4/2001 | Aboul Hosn et al. |
| 6,210,318 | B1 | 4/2001 | Lederman |
| 6,228,023 | B1 | 5/2001 | Zaslavsky et al. |
| 6,236,883 | B1 | 5/2001 | Ciaccio et al. |
| 6,254,359 | B1 | 7/2001 | Aber |
| 6,270,831 | B2 | 8/2001 | Kumar et al. |
| 6,273,861 | B1 | 8/2001 | Bates et al. |
| 6,283,949 | B1 | 9/2001 | Roorda |
| 6,287,319 | B1 | 9/2001 | Aboul Hosn et al. |
| 6,290,685 | B1 | 9/2001 | Insley et al. |
| 6,312,462 | B1 | 11/2001 | McDermott et al. |
| 6,314,322 | B1 | 11/2001 | Rosenberg |
| 6,319,231 | B1 | 11/2001 | Andrulitis |
| 6,361,292 | B1 | 3/2002 | Chang et al. |
| 6,361,501 | B1 | 3/2002 | Amano et al. |
| 6,364,833 | B1 | 4/2002 | Valerio et al. |
| 6,398,715 | B1 | 6/2002 | Magovern et al. |
| 6,400,991 | B1 | 6/2002 | Kung |
| 6,406,267 | B1 | 6/2002 | Mondiere |
| 6,406,422 | B1 | 6/2002 | Landesberg |
| 6,419,657 | B1 | 7/2002 | Pacetti |
| 6,422,990 | B1 | 7/2002 | Prem |
| 6,432,136 | B1 | 8/2002 | Weiss et al. |
| 6,443,944 | B1 | 9/2002 | Doshi et al. |
| 6,443,983 | B1 | 9/2002 | Nagyszalanczy et al. |
| 6,445,956 | B1 | 9/2002 | Laird et al. |
| 6,447,265 | B1 | 9/2002 | Antaki et al. |
| 6,447,266 | B2 | 9/2002 | Antaki et al. |
| 6,447,441 | B1 | 9/2002 | Yu et al. |
| 6,497,680 | B1 | 12/2002 | Holst et al. |
| 6,503,224 | B1 | 1/2003 | Forman et al. |
| 6,503,450 | B1 | 1/2003 | Afzal et al. |
| 6,508,787 | B2 | 1/2003 | Erbel et al. |
| 6,508,806 | B1 | 1/2003 | Hoste |
| 6,527,699 | B1 | 3/2003 | Goldowsky |
| 6,533,716 | B1 | 3/2003 | Schmitz-Rode et al. |
| 6,533,724 | B2 | 3/2003 | McNair |
| 6,537,315 | B2 | 3/2003 | Yamazaki et al. |
| 6,540,658 | B1 | 4/2003 | Fasciano et al. |
| 6,540,659 | B1 | 4/2003 | Milbocker |
| 6,544,543 | B1 | 4/2003 | Mandrusov et al. |
| 6,547,716 | B1 | 4/2003 | Milbocker |
| 6,562,022 | B2 | 5/2003 | Hoste et al. |
| 6,572,529 | B2 | 6/2003 | Wilk |
| 6,572,534 | B1 | 6/2003 | Milbocker et al. |
| 6,595,943 | B1 | 7/2003 | Burbank |
| 6,602,182 | B1 | 8/2003 | Milbocker |
| 6,616,596 | B1 | 9/2003 | Milbocker |
| 6,620,120 | B2 | 9/2003 | Landry et al. |
| 6,623,420 | B2 | 9/2003 | Reich et al. |
| 6,626,821 | B1 | 9/2003 | Kung et al. |
| 6,626,889 | B1 | 9/2003 | Simpson et al. |
| 6,626,935 | B1 | 9/2003 | Ainsworth et al. |
| 6,632,215 | B1 | 10/2003 | Lemelson |
| 6,635,083 | B1 | 10/2003 | Cheng et al. |
| 6,656,220 | B1 | 12/2003 | Gomez et al. |
| 6,669,624 | B2 | 12/2003 | Frazier |
| 6,669,662 | B1 | 12/2003 | Webler |
| 6,676,679 | B1 | 1/2004 | Mueller et al. |
| 6,685,696 | B2 | 2/2004 | Fleischhacker et al. |
| 6,688,869 | B1 | 2/2004 | Simonds |
| 6,699,231 | B1 | 3/2004 | Sterman et al. |
| 6,709,382 | B1 | 3/2004 | Homer |
| 6,712,844 | B2 | 3/2004 | Pacetti |
| 6,730,102 | B1 | 5/2004 | Burdulis et al. |
| 6,746,416 | B2 | 6/2004 | Hubbard et al. |
| 6,749,615 | B2 | 6/2004 | Burdulis et al. |
| 6,769,871 | B2 | 8/2004 | Yamazaki |
| 6,790,171 | B1 | 9/2004 | Gründeman et al. |
| 6,811,749 | B2 | 11/2004 | Lindsay |
| 6,821,295 | B1 | 11/2004 | Farrar |
| 6,837,890 | B1 | 1/2005 | Chludzinski et al. |
| 6,846,296 | B1 | 1/2005 | Milbocker et al. |
| 6,866,650 | B2 | 3/2005 | Stevens et al. |
| 6,879,126 | B2 | 4/2005 | Paden et al. |
| 6,884,210 | B2 | 4/2005 | Nose et al. |
| 6,908,280 | B2 | 6/2005 | Yamazaki |
| 6,908,435 | B1 | 6/2005 | Mueller et al. |
| 6,929,632 | B2 | 8/2005 | Nita et al. |
| 6,929,660 | B1 | 8/2005 | Ainsworth et al. |
| 6,942,672 | B2 | 9/2005 | Heilman et al. |
| 6,945,978 | B1 | 9/2005 | Hyde |
| 6,949,066 | B2 | 9/2005 | Bearson et al. |
| 6,969,345 | B2 | 11/2005 | Jassawalla et al. |
| 6,981,942 | B2 | 1/2006 | Khaw et al. |
| 7,022,100 | B1 | 4/2006 | Aboul Hosn et al. |
| 7,025,742 | B2 | 4/2006 | Rubenstein et al. |
| 7,027,875 | B2 | 4/2006 | Siess et al. |
| 7,029,483 | B2 | 4/2006 | Schwartz |
| 7,037,253 | B2 | 5/2006 | French et al. |
| 7,048,747 | B2 | 5/2006 | Arcia et al. |
| 7,074,018 | B2 | 7/2006 | Chang |
| 7,108,652 | B2 | 9/2006 | Stenberg et al. |
| 7,118,525 | B2 | 10/2006 | Coleman et al. |
| 7,122,151 | B2 | 10/2006 | Reeder et al. |
| 7,125,376 | B2 | 10/2006 | Viole et al. |
| 7,126,310 | B1 | 10/2006 | Barron |
| 7,150,711 | B2 | 12/2006 | Nüsser et al. |
| 7,155,291 | B2 | 12/2006 | Zarinetchi et al. |
| 7,172,551 | B2 | 2/2007 | Leasure |
| 7,189,260 | B2 | 3/2007 | Horvath et al. |
| 7,220,275 | B2 | 5/2007 | Davidson et al. |
| 7,229,258 | B2 | 6/2007 | Wood et al. |
| 7,229,402 | B2 | 6/2007 | Diaz et al. |
| 7,238,151 | B2 | 7/2007 | Frazier |
| 7,244,224 | B2 | 7/2007 | Tsukahara et al. |
| 7,247,166 | B2 | 7/2007 | Pienknagura |
| 7,303,581 | B2 | 12/2007 | Peralta |
| 7,331,972 | B1 | 2/2008 | Cox |
| 7,331,987 | B1 | 2/2008 | Cox |
| 7,361,726 | B2 | 4/2008 | Pacetti et al. |
| 7,377,927 | B2 | 5/2008 | Burdulis et al. |
| 7,392,077 | B2 | 6/2008 | Mueller et al. |
| 7,393,181 | B2 | 7/2008 | McBride et al. |
| 7,396,327 | B2 | 7/2008 | Morello |
| 7,479,102 | B2 | 1/2009 | Jarvik |
| 7,520,850 | B2 | 4/2009 | Brockway |
| 7,524,277 | B1 | 4/2009 | Wang et al. |
| 7,541,000 | B2 | 6/2009 | Stringer et al. |
| 7,544,160 | B2 | 6/2009 | Gross |
| 7,547,391 | B2 | 6/2009 | Petrie |
| 7,585,322 | B2 | 9/2009 | Azzolina |
| 7,588,530 | B2 | 9/2009 | Heilman et al. |
| 7,588,549 | B2 | 9/2009 | Eccleston |
| 7,591,199 | B2 | 9/2009 | Weldon et al. |
| 7,611,478 | B2 | 11/2009 | Lucke et al. |
| 7,628,756 | B2 | 12/2009 | Hacker et al. |
| 7,713,259 | B2 | 5/2010 | Gosiengfiao et al. |

(56) References Cited

U.S. PATENT DOCUMENTS

| | | | |
|---|---|---|---|
| RE41,394 E | 6/2010 | Bugge et al. |
| 7,736,296 B2 | 6/2010 | Siess et al. |
| 7,736,375 B2 | 6/2010 | Crow |
| 7,758,492 B2 | 7/2010 | Weatherbee |
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |
| 7,993,260 B2 | 8/2011 | Bolling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,194 B2 | 9/2011 | Edwin et al. |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahieh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,123,674 B2 | 2/2012 | Kuyava |
| 8,133,272 B2 | 3/2012 | Hyde |
| RE43,299 E | 4/2012 | Siess |
| 8,152,035 B2 | 4/2012 | Earl |
| 8,152,845 B2 | 4/2012 | Bourque |
| 8,153,083 B2 | 4/2012 | Briggs |
| 8,157,719 B1 | 4/2012 | Ainsworth et al. |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,649 B2 | 3/2013 | Woodard et al. |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |
| 8,849,398 B2 | 9/2014 | Evans |
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |

(56) References Cited

U.S. PATENT DOCUMENTS 8,927,700 B2 1/2015 McCauley et al.
8,932,141 B2 1/2015 Liebing
8,932,197 B2 1/2015 Gregoric et al.
8,934,956 B2 1/2015 Glenn et al.
8,942,828 B1 1/2015 Schecter
8,944,748 B2 2/2015 Liebing
8,945,159 B2 2/2015 Nussbaum
8,956,402 B2 2/2015 Cohn
8,961,387 B2 2/2015 Duncan
8,961,466 B2 2/2015 Steinbach
8,971,980 B2 3/2015 Mace et al.
8,974,519 B2 3/2015 Gennrich et al.
8,992,406 B2 3/2015 Corbett
8,997,349 B2 4/2015 Mori et al.
9,002,468 B2 4/2015 Shea et al.
9,023,010 B2 5/2015 Chiu et al.
9,028,216 B2 5/2015 Schumacher et al.
9,028,392 B2 5/2015 Shifflette
9,028,859 B2 5/2015 Hossainy et al.
9,033,863 B2 5/2015 Jarvik
9,033,909 B2 5/2015 Aihara
9,039,595 B2 5/2015 Ayre et al.
9,044,236 B2 6/2015 Nguyen et al.
9,056,159 B2 6/2015 Medvedev et al.
9,066,992 B2 6/2015 Stankus et al.
9,067,005 B2 6/2015 Ozaki et al.
9,067,006 B2 6/2015 Toellner
9,072,825 B2 7/2015 Pfeffer et al.
9,078,692 B2 7/2015 Shturman et al.
9,089,329 B2 7/2015 Hoarau et al.
9,089,634 B2 7/2015 Schumacher et al.
9,089,635 B2 7/2015 Reichenbach et al.
9,089,670 B2 7/2015 Scheckel
9,095,428 B2 8/2015 Kabir et al.
9,096,703 B2 8/2015 Li et al.
9,101,302 B2 8/2015 Mace et al.
9,125,977 B2 9/2015 Nishimura et al.
9,127,680 B2 9/2015 Yanal et al.
9,138,516 B2 9/2015 Vischer et al.
9,138,518 B2 9/2015 Campbell et al.
9,144,638 B2 9/2015 Zimmermann et al.
9,162,017 B2 10/2015 Evans et al.
9,168,361 B2 10/2015 Ehrenreich et al.
9,180,227 B2 11/2015 Ludwig et al.
9,180,235 B2 11/2015 Forsell
9,192,705 B2 11/2015 Yanal et al.
9,199,020 B2 12/2015 Siess
9,217,442 B2 12/2015 Wiessler et al.
D746,975 S 1/2016 Schenck et al.
9,227,002 B1 1/2016 Giridharan et al.
9,239,049 B2 1/2016 Jamagin et al.
9,265,870 B2 2/2016 Reichenbach et al.
9,278,189 B2 3/2016 Corbett
9,283,314 B2 3/2016 Prasad et al.
9,291,591 B2 3/2016 Simmons et al.
9,295,550 B2 3/2016 Nguyen et al.
9,295,767 B2 3/2016 Schmid et al.
9,308,302 B2 4/2016 Zeng
9,308,304 B2 4/2016 Peters et al.
9,314,558 B2 4/2016 Er
9,314,559 B2 4/2016 Smith et al.
9,328,741 B2 5/2016 Liebing
9,333,284 B2 5/2016 Thompson et al.
9,339,596 B2 5/2016 Roehn
9,345,824 B2 5/2016 Mohl et al.
9,358,329 B2 * 6/2016 Fitzgerald ............. A61M 60/81
9,358,330 B2 6/2016 Schumacher
9,364,255 B2 6/2016 Weber
9,364,592 B2 6/2016 McBride et al.
9,370,613 B2 6/2016 Hsu et al.
9,375,445 B2 6/2016 Hossainy et al.
9,381,285 B2 7/2016 Ozaki et al.
9,387,284 B2 7/2016 Heilman et al.
9,409,012 B2 8/2016 Eidenschink et al.
9,416,783 B2 8/2016 Schumacher et al.
9,416,791 B2 8/2016 Toellner
9,421,311 B2 8/2016 Tanner et al.
9,433,713 B2 9/2016 Corbett et al.
9,435,450 B2 9/2016 Muennich
9,446,179 B2 9/2016 Keenan et al.
9,452,249 B2 9/2016 Kearsley et al.
9,474,840 B2 10/2016 Siess
9,486,565 B2 11/2016 Göllner et al.
9,492,601 B2 11/2016 Casas et al.
9,504,491 B2 11/2016 Callas et al.
9,511,179 B2 12/2016 Casas et al.
9,522,257 B2 12/2016 Webler
9,526,818 B2 12/2016 Kearsley et al.
9,533,084 B2 1/2017 Siess et al.
9,533,085 B2 1/2017 Hanna
9,539,378 B2 1/2017 Tuseth
9,550,017 B2 1/2017 Spanier et al.
9,555,173 B2 1/2017 Spanier
9,555,175 B2 1/2017 Bulent et al.
9,555,177 B2 1/2017 Curtis et al.
9,556,873 B2 1/2017 Yanal et al.
9,561,309 B2 2/2017 Glauser et al.
9,561,313 B2 2/2017 Taskin
9,592,328 B2 3/2017 Jeevanandam et al.
9,603,983 B2 3/2017 Rochn et al.
9,603,984 B2 3/2017 Romero et al.
9,611,743 B2 4/2017 Toellner et al.
9,612,182 B2 4/2017 Olde et al.
9,616,157 B2 4/2017 Akdis
9,616,159 B2 4/2017 Anderson et al.
9,623,163 B1 4/2017 Fischi
9,631,754 B2 4/2017 Richardson et al.
9,642,984 B2 5/2017 Schumacher et al.
9,656,010 B2 5/2017 Burke
9,656,030 B1 5/2017 Webler et al.
9,662,211 B2 5/2017 Hodson et al.
9,669,141 B2 6/2017 Parker et al.
9,669,142 B2 6/2017 Spanier et al.
9,669,143 B2 6/2017 Guerrero
9,675,450 B2 6/2017 Straka et al.
9,675,738 B2 6/2017 Tanner et al.
9,675,739 B2 6/2017 Tanner et al.
9,675,742 B2 6/2017 Casas et al.
9,687,596 B2 6/2017 Poirier
9,687,630 B2 6/2017 Basu et al.
9,700,659 B2 7/2017 Kantrowitz et al.
9,713,662 B2 7/2017 Rosenberg et al.
9,713,663 B2 7/2017 Medvedev et al.
9,715,839 B2 7/2017 Pybus et al.
9,717,615 B2 8/2017 Grandt
9,717,832 B2 8/2017 Taskin et al.
9,717,839 B2 8/2017 Hashimoto
9,726,195 B2 8/2017 Cecere et al.
9,731,058 B2 8/2017 Siebenhaar et al.
9,731,101 B2 8/2017 Bertrand et al.
9,737,361 B2 8/2017 Magana et al.
9,737,651 B2 8/2017 Wampler
9,744,280 B2 8/2017 Schade et al.
9,744,287 B2 8/2017 Bulent et al.
9,750,859 B2 9/2017 Bulent et al.
9,757,502 B2 9/2017 Burke et al.
9,770,202 B2 9/2017 Ralston et al.
9,770,543 B2 9/2017 Tanner et al.
9,771,801 B2 9/2017 Schumacher et al.
9,775,930 B2 10/2017 Michal et al.
9,782,279 B2 10/2017 Kassab
9,782,527 B2 10/2017 Thomas et al.
9,795,780 B2 10/2017 Serna et al.
9,801,987 B2 10/2017 Faman et al.
9,801,992 B2 10/2017 Giordano et al.
9,821,098 B2 11/2017 Horvath et al.
9,821,146 B2 11/2017 Tao et al.
9,827,356 B2 11/2017 Muller et al.
9,833,314 B2 12/2017 Corbett
9,833,550 B2 12/2017 Siess
9,833,551 B2 12/2017 Criscione et al.
9,839,734 B1 12/2017 Menon et al.
9,844,618 B2 12/2017 Muller-Spanka et al.
9,850,906 B2 12/2017 Ozaki et al.

(56) References Cited

U.S. PATENT DOCUMENTS 9,855,437 B2 1/2018 Nguyen et al.
9,861,504 B2 1/2018 Abunassar et al.
9,861,731 B2 1/2018 Tamburino
9,872,948 B2 1/2018 Siess
9,878,087 B2 1/2018 Richardson et al.
9,878,169 B2 1/2018 Hossainy
9,889,242 B2 2/2018 Pfeffer et al.
9,895,244 B2 2/2018 Papp et al.
9,895,475 B2 2/2018 Toellner et al.
9,907,890 B2 3/2018 Muller
9,907,892 B2 3/2018 Broen et al.
9,913,937 B2 3/2018 Schwammenthal et al.
9,918,822 B2 3/2018 Abunassar et al.
9,919,085 B2 3/2018 Throckmorton et al.
9,919,088 B2 3/2018 Bonde et al.
9,919,089 B2 3/2018 Garrigue
9,950,101 B2 4/2018 Smith et al.
9,956,410 B2 5/2018 Deem et al.
9,962,258 B2 5/2018 Seguin et al.
9,974,893 B2 5/2018 Toellner
9,974,894 B2 5/2018 Morello
9,981,078 B2 5/2018 Jin et al.
9,985,374 B2 5/2018 Hodges
9,987,407 B2 6/2018 Grant et al.
10,010,273 B2 7/2018 Sloan et al.
10,022,499 B2 7/2018 Galasso
10,028,835 B2 7/2018 Kermode et al.
10,029,037 B2 7/2018 Muller et al.
10,029,038 B2 7/2018 Hodges
10,029,039 B2 7/2018 Dague et al.
10,031,124 B2 7/2018 Galasso
10,034,972 B2 7/2018 Wampler et al.
10,039,873 B2 8/2018 Siegenthaler
10,046,146 B2 8/2018 Manderfeld et al.
10,058,349 B2 8/2018 Gunderson et al.
10,058,641 B2 8/2018 Mollison et al.
10,058,652 B2 8/2018 Tsoukalis
10,058,653 B2 8/2018 Wang et al.
10,077,777 B2 9/2018 Horvath et al.
10,080,828 B2 9/2018 Wiesener et al.
10,080,834 B2 9/2018 Federspiel et al.
10,080,871 B2 9/2018 Schumacher et al.
10,569,005 B2 2/2020 Solem et al.
10,722,631 B2 7/2020 Salahieh et al.
10,881,770 B2 1/2021 Tuval et al.
11,123,538 B2 9/2021 Epple et al.
11,268,521 B2 3/2022 Toellner
11,280,345 B2 3/2022 Bredenbreuker et al.
11,850,413 B2 12/2023 Zeng et al.
12,017,056 B2 6/2024 Guo et al.
2001/0003802 A1 6/2001 Vitale
2001/0023369 A1 9/2001 Chobotov
2001/0046380 A1 11/2001 LeFebvre
2001/0053928 A1 12/2001 Edelman et al.
2002/0057989 A1 5/2002 Afzal et al.
2002/0058971 A1 5/2002 Zarinetchi et al.
2002/0068848 A1 6/2002 Zadini et al.
2002/0072679 A1 6/2002 Schock et al.
2002/0072779 A1 6/2002 Loeb
2002/0128709 A1 9/2002 Pless
2002/0147495 A1 10/2002 Petroff
2003/0069465 A1 4/2003 Benkowski et al.
2003/0088151 A1 5/2003 Kung et al.
2003/0131995 A1 7/2003 de Rouffignac et al.
2003/0155111 A1 8/2003 Vinegar et al.
2003/0173081 A1 9/2003 Vinegar et al.
2003/0173082 A1 9/2003 Vinegar et al.
2003/0173085 A1 9/2003 Vinegar et al.
2003/0178191 A1 9/2003 Maher et al.
2003/0209348 A1 11/2003 Ward et al.
2003/0217957 A1 11/2003 Bowman et al.
2004/0024285 A1 2/2004 Muckter
2004/0040715 A1 3/2004 Wellington et al.
2004/0097782 A1 5/2004 Korakianitis et al.
2004/0097783 A1 5/2004 Peters et al.
2004/0228724 A1 11/2004 Capone et al.
2004/0249363 A1 12/2004 Burke et al.
2005/0010077 A1 1/2005 Calderon
2005/0043805 A1 2/2005 Chudik
2005/0049696 A1 3/2005 Siess et al.
2005/0060036 A1 3/2005 Schultz et al.
2005/0113632 A1 5/2005 Ortiz et al.
2005/0119599 A1 6/2005 Kanz et al.
2005/0187616 A1 8/2005 Realyvasquez
2005/0209617 A1 9/2005 Koven et al.
2005/0220636 A1 10/2005 Henein et al.
2005/0246010 A1 11/2005 Alexander et al.
2005/0254976 A1 11/2005 Carrier et al.
2005/0256540 A1 11/2005 Silver et al.
2005/0277803 A1 12/2005 Pecor
2006/0111641 A1 5/2006 Manera et al.
2006/0116700 A1 6/2006 Crow
2006/0129082 A1 6/2006 Rozga
2006/0155158 A1 7/2006 Aboul Hosn
2006/0177343 A1 8/2006 Brian et al.
2006/0195098 A1 8/2006 Schumacher
2006/0257355 A1 11/2006 Stewart et al.
2006/0293664 A1 12/2006 Schumacher
2007/0106274 A1 5/2007 Ayre et al.
2007/0167091 A1 7/2007 Schumacher
2007/0203453 A1 8/2007 Mori et al.
2007/0213690 A1 9/2007 Phillips et al.
2007/0250148 A1 10/2007 Perry et al.
2007/0253842 A1 11/2007 Horvath et al.
2007/0265673 A1 11/2007 Ransbury et al.
2007/0270633 A1 11/2007 Cook et al.
2007/0299314 A1 12/2007 Bertolero et al.
2008/0045779 A1 2/2008 Rinaldi et al.
2008/0065014 A1 3/2008 Von Oepen et al.
2008/0076101 A1 3/2008 Hyde et al.
2008/0097273 A1 4/2008 Levin et al.
2008/0097562 A1 4/2008 Tan
2008/0119421 A1 5/2008 Tuszynski et al.
2008/0132748 A1 6/2008 Shifflette
2008/0132749 A1 6/2008 Hegde et al.
2008/0167679 A1 7/2008 Papp
2008/0167711 A1 7/2008 Roorda
2008/0188923 A1 8/2008 Chu
2008/0200750 A1 8/2008 James
2008/0208329 A1 8/2008 Bishop et al.
2008/0228026 A1 9/2008 Manera et al.
2008/0240947 A1 10/2008 Allaire et al.
2008/0243030 A1 10/2008 Seibel et al.
2008/0275295 A1 11/2008 Gertner
2008/0275354 A1 11/2008 Thuramalla et al.
2008/0296433 A1 12/2008 Brenner et al.
2008/0300677 A1 12/2008 Schrayer
2009/0012460 A1 1/2009 Steck et al.
2009/0061072 A1 3/2009 Isch et al.
2009/0063402 A1 3/2009 Hayter
2009/0082723 A1 3/2009 Krogh et al.
2009/0143635 A1 6/2009 Benkowski et al.
2009/0171448 A1 7/2009 Eli
2009/0177028 A1 7/2009 White
2009/0182307 A1 7/2009 Yap et al.
2009/0188964 A1 7/2009 Orlov
2009/0259089 A1 10/2009 Gelbart et al.
2010/0016703 A1 1/2010 Batkin et al.
2010/0022943 A1 1/2010 Mauch et al.
2010/0042037 A1 2/2010 Felt et al.
2010/0076380 A1 3/2010 Hui
2010/0084326 A1 4/2010 Takesawa
2010/0087742 A1 4/2010 Bishop et al.
2010/0105978 A1 4/2010 Matsui et al.
2010/0152523 A1 6/2010 MacDonald et al.
2010/0152525 A1 6/2010 Weizman et al.
2010/0152526 A1 6/2010 Pacella et al.
2010/0160751 A1 6/2010 Hete et al.
2010/0184318 A1 7/2010 Bogart et al.
2010/0185220 A1 7/2010 Naghavi et al.
2010/0222635 A1 9/2010 Poirier
2010/0222878 A1 9/2010 Poirier
2010/0249489 A1 9/2010 Jarvik

(56) References Cited

U.S. PATENT DOCUMENTS

2011/0004046 A1* 1/2011 Campbell ........... A61M 60/422 600/16
2011/0098548 A1 4/2011 Budiman et al.
2011/0106115 A1 5/2011 Haselby et al.
2011/0106120 A1 5/2011 Haselby et al.
2011/0178596 A1 7/2011 Hauck et al.
2011/0224655 A1 9/2011 Asirvatham et al.
2011/0297599 A1 12/2011 Lo et al.
2011/0301625 A1 12/2011 Mauch et al.
2011/0304240 A1 12/2011 Meitav et al.
2012/0022316 A1 1/2012 Aboul-Hosn et al.
2012/0028908 A1 2/2012 Viswanath et al.
2012/0039711 A1 2/2012 Roehn
2012/0109060 A1 5/2012 Kick et al.
2012/0165641 A1 6/2012 Burnett et al.
2012/0179184 A1 7/2012 Orlov
2012/0184803 A1 7/2012 Simon et al.
2012/0190918 A1 7/2012 Oepen et al.
2012/0239139 A1 9/2012 Whendt et al.
2012/0252709 A1 10/2012 Felts et al.
2012/0289928 A1 11/2012 Wright et al.
2012/0302458 A1 11/2012 Adamczyk et al.
2012/0330683 A1 12/2012 Ledwidge et al.
2013/0023373 A1 1/2013 Janek
2013/0040407 A1 2/2013 Brophy et al.
2013/0053693 A1 2/2013 Breznock et al.
2013/0144144 A1 6/2013 Laster et al.
2013/0211489 A1 8/2013 Makower et al.
2013/0233798 A1 9/2013 Wiktor et al.
2013/0245360 A1 9/2013 Schumacher
2013/0267892 A1 10/2013 Woolford
2013/0281761 A1 10/2013 Kapur
2013/0289696 A1 10/2013 Maggard et al.
2013/0310845 A1 11/2013 Thor et al.
2013/0317604 A1 11/2013 Min et al.
2013/0344047 A1 12/2013 Pacetti et al.
2014/0012065 A1* 1/2014 Fitzgerald ............. A61M 60/13 600/16
2014/0017200 A1 1/2014 Michal et al.
2014/0039465 A1 2/2014 Schulz et al.
2014/0039603 A1 2/2014 Wang
2014/0051908 A1 2/2014 Khanal et al.
2014/0058190 A1 2/2014 Gohean et al.
2014/0066693 A1 3/2014 Goldfarb et al.
2014/0128659 A1 5/2014 Heuring et al.
2014/0128795 A1 5/2014 Keren et al.
2014/0148638 A1 5/2014 LaRose et al.
2014/0163664 A1 6/2014 Goldsmith
2014/0190523 A1 7/2014 Garvey et al.
2014/0194678 A1 7/2014 Wildhirt et al.
2014/0194717 A1 7/2014 Wildhirt et al.
2014/0199377 A1 7/2014 Stankus et al.
2014/0200655 A1 7/2014 Webler et al.
2014/0207232 A1 7/2014 Garrigue
2014/0228741 A1 8/2014 Frankowski et al.
2014/0243970 A1 8/2014 Yanai
2014/0255176 A1 9/2014 Bredenbreuker et al.
2014/0260551 A1 9/2014 Gray et al.
2014/0275721 A1 9/2014 Yanal et al.
2014/0275725 A1 9/2014 Schenck et al.
2014/0288354 A1 9/2014 Timms et al.
2014/0309481 A1 10/2014 Medvedev et al.
2014/0336444 A1 11/2014 Bonde
2014/0336486 A1 11/2014 Ouyang et al.
2014/0336747 A1 11/2014 Rapoza et al.
2014/0341726 A1 11/2014 Wu et al.
2014/0350328 A1 11/2014 Mohl
2014/0357938 A1 12/2014 Pilla et al.
2014/0370073 A1 12/2014 Tang et al.
2015/0005571 A1 1/2015 Jeffery et al.
2015/0018747 A1 1/2015 Michal et al.
2015/0031938 A1 1/2015 Crosby et al.
2015/0051437 A1 2/2015 Miyakoshi et al.
2015/0068069 A1 3/2015 Tran et al.
2015/0080639 A1 3/2015 Radziemski et al.
2015/0080743 A1 3/2015 Siess
2015/0087890 A1 3/2015 Spanier et al.
2015/0101645 A1 4/2015 Neville et al.
2015/0112210 A1 4/2015 Webler
2015/0119859 A1 4/2015 Cajamarca et al.
2015/0120323 A1 4/2015 Galasso et al.
2015/0134048 A1 5/2015 Ding
2015/0152878 A1 6/2015 McBride et al.
2015/0159643 A1 6/2015 Koob
2015/0174060 A1 6/2015 Heit et al.
2015/0191607 A1 7/2015 McDaniel
2015/0207331 A1 7/2015 Petersen
2015/0216685 A1 8/2015 Spence et al.
2015/0222128 A1 8/2015 Hansen
2015/0222139 A1 8/2015 Petersen et al.
2015/0226691 A1 8/2015 Wang et al.
2015/0230709 A1 8/2015 Milner et al.
2015/0231317 A1 8/2015 Schima et al.
2015/0238671 A1 8/2015 Mesallum
2015/0265757 A1 9/2015 Dowling et al.
2015/0283027 A1 10/2015 Lampe et al.
2015/0285258 A1 10/2015 Foster
2015/0290370 A1 10/2015 Crunkleton et al.
2015/0290377 A1 10/2015 Kearsley et al.
2015/0306291 A1 10/2015 Bonde et al.
2015/0320926 A1 11/2015 Fitzpatrick et al.
2015/0328382 A1 11/2015 Corbett et al.
2015/0335803 A1 11/2015 Yamane
2015/0364861 A1 12/2015 Lucke et al.
2015/0366495 A1 12/2015 Gable, III et al.
2015/0367050 A1 12/2015 Bulent et al.
2015/0368335 A1 12/2015 Banerjee et al.
2015/0374892 A1 12/2015 Yanai et al.
2016/0022887 A1 1/2016 Wampler
2016/0030649 A1 2/2016 Zeng
2016/0038315 A1 2/2016 Consigny et al.
2016/0045098 A1 2/2016 Tsubouchi
2016/0045652 A1 2/2016 Comen
2016/0045654 A1 2/2016 Connor
2016/0053763 A1 2/2016 Toellner
2016/0058434 A1 3/2016 Delaloye et al.
2016/0067395 A1 3/2016 Jimenez et al.
2016/0085714 A1 3/2016 Goodnow et al.
2016/0175044 A1 6/2016 Abunassar et al.
2016/0182158 A1 6/2016 Lee et al.
2016/0184499 A1 6/2016 Ricci et al.
2016/0199543 A1* 7/2016 Venkateswara-Rao ..................... A61L 31/088 514/769
2016/0199556 A1 7/2016 Ayre et al.
2016/0199557 A1 7/2016 Bluvshtein et al.
2016/0203275 A1 7/2016 Benjamin et al.
2016/0206798 A1 7/2016 Williams et al.
2016/0220269 A1 8/2016 Labropoulos et al.
2016/0220785 A1 8/2016 Fabro
2016/0222969 A1 8/2016 Heide et al.
2016/0250399 A1 9/2016 Tiller et al.
2016/0250400 A1 9/2016 Schumacher
2016/0251720 A1 9/2016 Schulze et al.
2016/0256620 A1 9/2016 Scheckel et al.
2016/0263299 A1 9/2016 Xu et al.
2016/0271161 A1 9/2016 Dobson
2016/0271309 A1 9/2016 Throckmorton et al.
2016/0279310 A1 9/2016 Scheckel et al.
2016/0303301 A1 10/2016 Bluvshtein et al.
2016/0308403 A1 10/2016 Bluvshtein et al.
2016/0317291 A1 11/2016 Bishop et al.
2016/0317333 A1 11/2016 Ainsworth et al.
2016/0325034 A1 11/2016 Wiktor et al.
2016/0348688 A1 12/2016 Schumacher et al.
2016/0354526 A1 12/2016 Whisenant et al.
2016/0375187 A1 12/2016 Lee et al.
2017/0000361 A1 1/2017 Meyering et al.
2017/0000935 A1 1/2017 Vasilyev et al.
2017/0007552 A1 1/2017 Slepian
2017/0007762 A1 1/2017 Hayter et al.
2017/0014401 A1 1/2017 Dalton et al.
2017/0021074 A1 1/2017 Opfermann et al.
2017/0028114 A1 2/2017 Göllner et al.

(56) References Cited

U.S. PATENT DOCUMENTS

| | | | |
|---|---|---|---|
| 2017/0028115 | A1 | 2/2017 | Muller |
| 2017/0035952 | A1 | 2/2017 | Muller |
| 2017/0035954 | A1 | 2/2017 | Muller et al. |
| 2017/0043076 | A1 | 2/2017 | Wampler et al. |
| 2017/0063143 | A1 | 3/2017 | Hoarau et al. |
| 2017/0080136 | A1 | 3/2017 | Janeczek et al. |
| 2017/0100527 | A1 | 4/2017 | Schwammenthal et al. |
| 2017/0112984 | A1 | 4/2017 | Vargas Fonseca |
| 2017/0119945 | A1 | 5/2017 | Neumann |
| 2017/0119946 | A1 | 5/2017 | McChrystal et al. |
| 2017/0136165 | A1 | 5/2017 | Hansen et al. |
| 2017/0136225 | A1 | 5/2017 | Siess et al. |
| 2017/0143883 | A1 | 5/2017 | Spence |
| 2017/0143952 | A1 | 5/2017 | Siess et al. |
| 2017/0157309 | A1 | 6/2017 | Begg et al. |
| 2017/0193184 | A1 | 7/2017 | Hayter et al. |
| 2017/0196638 | A1 | 7/2017 | Serna et al. |
| 2017/0202575 | A1 | 7/2017 | Stanfield et al. |
| 2017/0215918 | A1 | 8/2017 | Tao et al. |
| 2017/0224896 | A1 | 8/2017 | Graham et al. |
| 2017/0232168 | A1 | 8/2017 | Reichenbach et al. |
| 2017/0232169 | A1 | 8/2017 | Muller |
| 2017/0232172 | A1 | 8/2017 | Mesallum |
| 2017/0239407 | A1 | 8/2017 | Hayward |
| 2017/0250575 | A1 | 8/2017 | Wong et al. |
| 2017/0265994 | A1 | 9/2017 | Krone |
| 2017/0274128 | A1 | 9/2017 | Tamburino et al. |
| 2017/0281025 | A9 | 10/2017 | Glover et al. |
| 2017/0281841 | A1 | 10/2017 | Larose et al. |
| 2017/0281842 | A1 | 10/2017 | Larose et al. |
| 2017/0290964 | A1 | 10/2017 | Barry |
| 2017/0296227 | A1 | 10/2017 | Osypka |
| 2017/0296725 | A1 | 10/2017 | Peters et al. |
| 2017/0312106 | A1 | 11/2017 | Gomez et al. |
| 2017/0312416 | A1 | 11/2017 | Strueber |
| 2017/0312492 | A1 | 11/2017 | Fantuzzi et al. |
| 2017/0319113 | A1 | 11/2017 | Hurd et al. |
| 2017/0323713 | A1 | 11/2017 | Moeller et al. |
| 2017/0325943 | A1 | 11/2017 | Robin et al. |
| 2017/0333607 | A1 | 11/2017 | Zarins |
| 2017/0333673 | A1 | 11/2017 | Tuval et al. |
| 2017/0340788 | A1 | 11/2017 | Korakianitis et al. |
| 2017/0340789 | A1 | 11/2017 | Bonde et al. |
| 2017/0340790 | A1 | 11/2017 | Wiesener et al. |
| 2017/0348470 | A1 | 12/2017 | D'Ambrosio et al. |
| 2017/0360309 | A1 | 12/2017 | Moore et al. |
| 2017/0361001 | A1 | 12/2017 | Canatella et al. |
| 2017/0361011 | A1 | 12/2017 | Muennich et al. |
| 2017/0363103 | A1 | 12/2017 | Canatella et al. |
| 2017/0363210 | A1 | 12/2017 | Durst et al. |
| 2017/0363620 | A1 | 12/2017 | Beshiri et al. |
| 2017/0368246 | A1 | 12/2017 | Criscione et al. |
| 2017/0370365 | A1 | 12/2017 | Fritz et al. |
| 2018/0001003 | A1 | 1/2018 | Moran et al. |
| 2018/0001007 | A1 | 1/2018 | Stratton |
| 2018/0001012 | A1 | 1/2018 | Ardehali |
| 2018/0001062 | A1 | 1/2018 | O'Carrol et al. |
| 2018/0015214 | A1 | 1/2018 | Lynch |
| 2018/0021494 | A1 | 1/2018 | Muller et al. |
| 2018/0021495 | A1 | 1/2018 | Muller et al. |
| 2018/0021497 | A1 | 1/2018 | Nunez et al. |
| 2018/0028736 | A1 | 2/2018 | Wong et al. |
| 2018/0035926 | A1 | 2/2018 | Stafford |
| 2018/0040418 | A1 | 2/2018 | Hansen et al. |
| 2018/0047282 | A1 | 2/2018 | He et al. |
| 2018/0050139 | A1 | 2/2018 | Siess et al. |
| 2018/0050140 | A1 | 2/2018 | Siess et al. |
| 2018/0050142 | A1 | 2/2018 | Siess et al. |
| 2018/0055383 | A1 | 3/2018 | Manera |
| 2018/0055983 | A1 | 3/2018 | Bourque |
| 2018/0058437 | A1 | 3/2018 | Eilers et al. |
| 2018/0064862 | A1 | 3/2018 | Keenan et al. |
| 2018/0071020 | A1 | 3/2018 | Laufer et al. |
| 2018/0078159 | A1 | 3/2018 | Edelman et al. |
| 2018/0085505 | A1 | 3/2018 | Casas |
| 2018/0085507 | A1 | 3/2018 | Casas et al. |
| 2018/0085509 | A1 | 3/2018 | Petersen |
| 2018/0093026 | A1 | 4/2018 | Angwin et al. |
| 2018/0097368 | A1 | 4/2018 | Hansen |
| 2018/0099076 | A1 | 4/2018 | Larose |
| 2018/0099078 | A1 | 4/2018 | Tuseth et al. |
| 2018/0100507 | A1 | 4/2018 | Wu et al. |
| 2018/0103611 | A1 | 4/2018 | Mainini et al. |
| 2018/0103870 | A1 | 4/2018 | Limaye et al. |
| 2018/0108275 | A1 | 4/2018 | Newberry et al. |
| 2018/0110514 | A1 | 4/2018 | Hoarau et al. |
| 2018/0114426 | A1 | 4/2018 | Lee |
| 2018/0133380 | A1 | 5/2018 | Liebing |
| 2018/0140759 | A1 | 5/2018 | Kaiser et al. |
| 2018/0140801 | A1 | 5/2018 | Voss et al. |
| 2018/0146968 | A1 | 5/2018 | Nitzan et al. |
| 2018/0149164 | A1 | 5/2018 | Siess |
| 2018/0149165 | A1 | 5/2018 | Siess et al. |
| 2018/0154051 | A1 | 6/2018 | Hossainy et al. |
| 2018/0154128 | A1 | 6/2018 | Woo et al. |
| 2018/0161540 | A1 | 6/2018 | Fantuzzi et al. |
| 2018/0161555 | A1 | 6/2018 | Zhadkevich |
| 2018/0168469 | A1 | 6/2018 | Granegger |
| 2018/0169312 | A1 | 6/2018 | Barry |
| 2018/0169313 | A1 | 6/2018 | Schwammenthal et al. |
| 2018/0193543 | A1 | 7/2018 | Sun |
| 2018/0193614 | A1 | 7/2018 | Nitzan et al. |
| 2018/0193616 | A1 | 7/2018 | Nitzan et al. |
| 2018/0200420 | A1 | 7/2018 | Di Paola et al. |
| 2018/0200422 | A1 | 7/2018 | Nguyen et al. |
| 2018/0202962 | A1 | 7/2018 | Simmons et al. |
| 2018/0207334 | A1 | 7/2018 | Siess |
| 2018/0207337 | A1 | 7/2018 | Spence et al. |
| 2018/0207338 | A1 | 7/2018 | Bluvshtein et al. |
| 2018/0226997 | A1 | 8/2018 | Jia |
| 2018/0228953 | A1 | 8/2018 | Siess et al. |
| 2018/0228957 | A1 | 8/2018 | Colella |
| 2018/0242891 | A1 | 8/2018 | Bemstein et al. |
| 2018/0242976 | A1 | 8/2018 | Kizuka |
| 2018/0243086 | A1 | 8/2018 | Barbarino et al. |
| 2018/0243488 | A1 | 8/2018 | Callaway et al. |
| 2018/0243489 | A1 | 8/2018 | Haddadi |
| 2018/0243490 | A1 | 8/2018 | Kallenbach et al. |
| 2018/0243492 | A1 | 8/2018 | Salys |
| 2018/0250457 | A1 | 9/2018 | Morello et al. |
| 2018/0250458 | A1 | 9/2018 | Petersen et al. |
| 2018/0256242 | A1 | 9/2018 | Bluvshtein et al. |
| 2018/0256794 | A1 | 9/2018 | Rodefeld |
| 2018/0256795 | A1 | 9/2018 | Schade et al. |
| 2018/0256797 | A1 | 9/2018 | Schenck et al. |
| 2018/0256798 | A1 | 9/2018 | Botterbusch et al. |
| 2018/0256859 | A1 | 9/2018 | Korkuch |
| 2018/0264183 | A1 | 9/2018 | Jahangir |
| 2018/0264184 | A1 | 9/2018 | Jeffries et al. |
| 2018/0269692 | A1 | 9/2018 | Petersen et al. |
| 2018/0280598 | A1 | 10/2018 | Curran et al. |
| 2018/0280599 | A1 | 10/2018 | Harjes et al. |
| 2018/0280600 | A1 | 10/2018 | Harjes et al. |
| 2018/0280601 | A1 | 10/2018 | Harjes et al. |
| 2018/0280604 | A1 | 10/2018 | Hobro et al. |
| 2018/0289295 | A1 | 10/2018 | Hoss et al. |
| 2018/0289876 | A1 | 10/2018 | Nguyen et al. |
| 2018/0289877 | A1 | 10/2018 | Schumacher et al. |
| 2018/0296572 | A1 | 10/2018 | Deisher |
| 2018/0303990 | A1 * | 10/2018 | Siess .................... A61M 60/13 |
| 2019/0030231 | A1 | 1/2019 | Aboul-Hosn et al. |
| 2019/0083690 | A1 | 3/2019 | Siess et al. |
| 2019/0143018 | A1 * | 5/2019 | Salahieh ............. A61M 60/139 600/16 |
| 2019/0167873 | A1 | 6/2019 | Koike et al. |
| 2019/0209751 | A1 | 7/2019 | Tuval et al. |
| 2019/0290822 | A1 | 9/2019 | Igarashi |
| 2019/0321531 | A1 * | 10/2019 | Cambronne ........ A61M 60/894 |
| 2019/0344001 | A1 | 11/2019 | Salahieh et al. |
| 2020/0029951 | A1 | 1/2020 | Bessler et al. |
| 2020/0030510 | A1 | 1/2020 | Higgins |
| 2020/0038568 | A1 | 2/2020 | Higgins et al. |
| 2020/0114053 | A1 | 4/2020 | Salahieh et al. |
| 2020/0121835 | A1 | 4/2020 | Farago et al. |

(56) References Cited

U.S. PATENT DOCUMENTS

| | | | |
|---|---|---|---|
| 2020/0237981 | A1 | 7/2020 | Tuval et al. |
| 2020/0246527 | A1 | 8/2020 | Hildebrand et al. |
| 2020/0316268 | A1 | 10/2020 | Antoni et al. |
| 2020/0391014 | A1 | 12/2020 | Walters et al. |
| 2021/0052794 | A1 | 2/2021 | Tuval et al. |
| 2021/0113212 | A1 | 4/2021 | Lashinski et al. |
| 2021/0121679 | A1 | 4/2021 | Mohl et al. |
| 2022/0080178 | A1 | 3/2022 | Salahieh et al. |
| 2023/0043385 | A1 | 2/2023 | Varghai et al. |
| 2023/0201558 | A1 | 6/2023 | Varghai et al. |
| 2023/0218886 | A1 | 7/2023 | Robinson et al. |
| 2023/0264012 | A1 | 8/2023 | Brandt |
| 2023/0390544 | A1 | 12/2023 | Hildebrand et al. |
| 2023/0405298 | A1 | 12/2023 | Hildebrand et al. |
| 2023/0414920 | A1 | 12/2023 | Salahieh et al. |
| 2024/0001101 | A1 | 1/2024 | Wallin et al. |
| 2024/0115849 | A1 | 4/2024 | Dhaliwal et al. |
| 2024/0173540 | A1 | 5/2024 | Wallin et al. |

FOREIGN PATENT DOCUMENTS

| | | | |
|---|---|---|---|
| CA | 3014105 | A1 | 8/2017 |
| CN | 1040073 | A | 2/1990 |
| CN | 1008307 | B | 6/1990 |
| CN | 1053108 | A | 7/1991 |
| CN | 1105103 | A | 7/1995 |
| CN | 1146329 | A | 4/1997 |
| CN | 1179708 | A | 4/1998 |
| CN | 2326258 | Y | 6/1999 |
| CN | 1222862 | A | 7/1999 |
| CN | 1045058 | C | 9/1999 |
| CN | 1235849 | A | 11/1999 |
| CN | 2361290 | Y | 2/2000 |
| CN | 1254598 | A | 5/2000 |
| CN | 2386827 | Y | 7/2000 |
| CN | 2412579 | Y | 1/2001 |
| CN | 2417173 | Y | 1/2001 |
| CN | 1310647 | A | 8/2001 |
| CN | 1342497 | A | 4/2002 |
| CN | 1088795 | C | 8/2002 |
| CN | 2504815 | Y | 8/2002 |
| CN | 1376523 | A | 10/2002 |
| CN | 1097138 | C | 12/2002 |
| CN | 1105581 | C | 4/2003 |
| CN | 1421248 | A | 6/2003 |
| CN | 2558386 | Y | 7/2003 |
| CN | 1118304 | C | 8/2003 |
| CN | 1436048 | A | 8/2003 |
| CN | 1120729 | C | 9/2003 |
| CN | 2574609 | Y | 9/2003 |
| CN | 1140228 | C | 3/2004 |
| CN | 1161581 | C | 8/2004 |
| CN | 1167472 | C | 9/2004 |
| CN | 1527906 | A | 9/2004 |
| CN | 1559361 | A | 1/2005 |
| CN | 1559626 | A | 1/2005 |
| CN | 1572331 | A | 2/2005 |
| CN | 1202871 | C | 5/2005 |
| CN | 1679974 | A | 10/2005 |
| CN | 1694338 | A | 11/2005 |
| CN | 1705462 | A | 12/2005 |
| CN | 1239133 | C | 2/2006 |
| CN | 1239209 | C | 2/2006 |
| CN | 2754637 | Y | 2/2006 |
| CN | 1244381 | C | 3/2006 |
| CN | 1249339 | C | 4/2006 |
| CN | 2776418 | Y | 5/2006 |
| CN | 2787222 | Y | 6/2006 |
| CN | 1799652 | A | 7/2006 |
| CN | 1806774 | A | 7/2006 |
| CN | 1826463 | A | 8/2006 |
| CN | 1833735 | A | 9/2006 |
| CN | 1833736 | A | 9/2006 |
| CN | 2831716 | Y | 10/2006 |
| CN | 1874805 | A | 12/2006 |
| CN | 1301583 | C | 2/2007 |
| CN | 1921947 | A | 2/2007 |
| CN | 2880096 | Y | 3/2007 |
| CN | 2899800 | Y | 5/2007 |
| CN | 101001765 | A | 7/2007 |
| CN | 1329666 | C | 8/2007 |
| CN | 101024098 | A | 8/2007 |
| CN | 101031302 | A | 9/2007 |
| CN | 101112628 | A | 1/2008 |
| CN | 101121045 | A | 2/2008 |
| CN | 101124002 | A | 2/2008 |
| CN | 101132830 | A | 2/2008 |
| CN | 100382855 | C | 4/2008 |
| CN | 101256992 | A | 9/2008 |
| CN | 100429406 | C | 10/2008 |
| CN | 100439717 | C | 12/2008 |
| CN | 100472042 | C | 3/2009 |
| CN | 201208423 | Y | 3/2009 |
| CN | 100488577 | C | 5/2009 |
| CN | 201230980 | Y | 5/2009 |
| CN | 201239369 | Y | 5/2009 |
| CN | 201246310 | Y | 5/2009 |
| CN | 101448535 | A | 6/2009 |
| CN | 101522115 | A | 9/2009 |
| CN | 101534883 | A | 9/2009 |
| CN | 201308666 | Y | 9/2009 |
| CN | 101563605 | A | 10/2009 |
| CN | 100558416 | C | 11/2009 |
| CN | 100566765 | C | 12/2009 |
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822854 | B | 9/2012 |
| CN | 101822855 | B | 9/2012 |
| CN | 101189431 | B | 10/2012 |
| CN | 101810891 | B | 10/2012 |
| CN | 102711894 | A | 10/2012 |
| CN | 102869318 | A | 1/2013 |
| CN | 102917748 | A | 2/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |

(56) References Cited

FOREIGN PATENT DOCUMENTS

| | | | |
|---|---|---|---|
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104185456 | A | 12/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |
| CN | 102257279 | B | 3/2016 |
| CN | 102472719 | B | 3/2016 |
| CN | 103154738 | B | 3/2016 |
| CN | 105451787 | A | 3/2016 |
| CN | 205083494 | U | 3/2016 |
| CN | 103850979 | B | 4/2016 |
| CN | 105477706 | A | 4/2016 |
| CN | 105517589 | A | 4/2016 |
| CN | 205163763 | U | 4/2016 |
| CN | 103002833 | B | 5/2016 |
| CN | 103861163 | B | 5/2016 |
| CN | 105555204 | A | 5/2016 |
| CN | 205215814 | U | 5/2016 |
| CN | 102940911 | B | 6/2016 |
| CN | 105641762 | A | 6/2016 |
| CN | 105641763 | A | 6/2016 |
| CN | 105662439 | A | 6/2016 |
| CN | 105709287 | A | 6/2016 |
| CN | 105722477 | A | 6/2016 |
| CN | 205322884 | U | 6/2016 |
| CN | 104069555 | B | 7/2016 |
| CN | 105744915 | A | 7/2016 |
| CN | 105790453 | A | 7/2016 |
| CN | 105792780 | A | 7/2016 |
| CN | 105792864 | A | 7/2016 |
| CN | 103260666 | B | 8/2016 |
| CN | 103732171 | B | 8/2016 |
| CN | 103928971 | B | 8/2016 |
| CN | 105833370 | A | 8/2016 |
| CN | 205411785 | U | 8/2016 |
| CN | 205460099 | U | 8/2016 |
| CN | 205528886 | U | 8/2016 |
| CN | 103889369 | B | 9/2016 |
| CN | 104849482 | B | 9/2016 |
| CN | 105980660 | A | 9/2016 |
| CN | 106075621 | A | 11/2016 |
| CN | 106102657 | A | 11/2016 |
| CN | 205681272 | U | 11/2016 |
| CN | 205698666 | U | 11/2016 |
| CN | 205698725 | U | 11/2016 |
| CN | 205753678 | U | 11/2016 |
| CN | 106214288 | A | 12/2016 |
| CN | 106256321 | A | 12/2016 |
| CN | 205779766 | U | 12/2016 |
| CN | 106334224 | A | 1/2017 |
| CN | 205867186 | U | 1/2017 |
| CN | 205876589 | U | 1/2017 |
| CN | 103281971 | B | 2/2017 |
| CN | 106390218 | A | 2/2017 |
| CN | 103533970 | B | 3/2017 |
| CN | 104826183 | B | 3/2017 |
| CN | 106512117 | A | 3/2017 |
| CN | 106581840 | A | 4/2017 |
| CN | 104068947 | B | 5/2017 |
| CN | 106620912 | A | 5/2017 |
| CN | 106691363 | A | 5/2017 |
| CN | 106716137 | A | 5/2017 |
| CN | 106794293 | A | 5/2017 |
| CN | 104225696 | B | 6/2017 |
| CN | 104918578 | B | 6/2017 |
| CN | 105915005 | B | 6/2017 |
| CN | 106902404 | A | 6/2017 |
| CN | 106955140 | A | 7/2017 |
| CN | 206325049 | U | 7/2017 |
| CN | 206355093 | U | 7/2017 |
| CN | 105377321 | B | 8/2017 |
| CN | 107050543 | A | 8/2017 |
| CN | 107050544 | A | 8/2017 |
| CN | 107080870 | A | 8/2017 |
| CN | 107080871 | A | 8/2017 |
| CN | 107110875 | A | 8/2017 |
| CN | 206414547 | U | 8/2017 |
| CN | 206443963 | U | 8/2017 |
| CN | 103930214 | B | 9/2017 |
| CN | 104619361 | B | 9/2017 |
| CN | 104936550 | B | 9/2017 |
| CN | 105188618 | B | 9/2017 |
| CN | 107115162 | A | 9/2017 |
| CN | 107126299 | A | 9/2017 |
| CN | 107126588 | A | 9/2017 |
| CN | 107134208 | A | 9/2017 |
| CN | 107157623 | A | 9/2017 |
| CN | 103857363 | B | 10/2017 |
| CN | 104768500 | B | 10/2017 |
| CN | 105008841 | B | 10/2017 |
| CN | 105492036 | B | 10/2017 |
| CN | 107252339 | A | 10/2017 |
| CN | 107281567 | A | 10/2017 |
| CN | 206592332 | U | 10/2017 |
| CN | 107349484 | A | 11/2017 |
| CN | 206660203 | U | 11/2017 |
| CN | 105287050 | B | 12/2017 |
| CN | 105597172 | B | 12/2017 |
| CN | 105854097 | B | 12/2017 |
| CN | 107412892 | A | 12/2017 |
| CN | 107440681 | A | 12/2017 |
| CN | 107496054 | A | 12/2017 |
| CN | 104602647 | B | 1/2018 |

(56) References Cited

FOREIGN PATENT DOCUMENTS

| | | | |
|---|---|---|---|
| CN | 106061523 | B | 1/2018 |
| CN | 107551341 | A | 1/2018 |
| CN | 206934393 | U | 1/2018 |
| CN | 107693868 | A | 2/2018 |
| CN | 107693869 | A | 2/2018 |
| CN | 107708765 | A | 2/2018 |
| CN | 207018256 | U | 2/2018 |
| CN | 106029120 | B | 3/2018 |
| CN | 107753153 | A | 3/2018 |
| CN | 107754071 | A | 3/2018 |
| CN | 107798980 | A | 3/2018 |
| CN | 107835826 | A | 3/2018 |
| CN | 107837430 | A | 3/2018 |
| CN | 107862963 | A | 3/2018 |
| CN | 207125933 | U | 3/2018 |
| CN | 207136890 | U | 3/2018 |
| CN | 105120796 | B | 4/2018 |
| CN | 105214153 | B | 4/2018 |
| CN | 107865988 | A | 4/2018 |
| CN | 107886825 | A | 4/2018 |
| CN | 107913442 | A | 4/2018 |
| CN | 107921195 | A | 4/2018 |
| CN | 107923311 | A | 4/2018 |
| CN | 108025120 | A | 5/2018 |
| CN | 108025123 | A | 5/2018 |
| CN | 108066834 | A | 5/2018 |
| CN | 207410652 | U | 5/2018 |
| CN | 104470579 | B | 6/2018 |
| CN | 105188604 | B | 6/2018 |
| CN | 105492909 | B | 6/2018 |
| CN | 105498002 | B | 6/2018 |
| CN | 106535824 | B | 6/2018 |
| CN | 108136110 | A | 6/2018 |
| CN | 108144146 | A | 6/2018 |
| CN | 108175884 | A | 6/2018 |
| CN | 106028807 | B | 7/2018 |
| CN | 106310410 | B | 7/2018 |
| CN | 108273148 | A | 7/2018 |
| CN | 108310486 | A | 7/2018 |
| CN | 108348667 | A | 7/2018 |
| CN | 207614108 | U | 7/2018 |
| CN | 105640635 | B | 8/2018 |
| CN | 105923112 | B | 8/2018 |
| CN | 108367106 | A | 8/2018 |
| CN | 108430533 | A | 8/2018 |
| CN | 108457844 | A | 8/2018 |
| CN | 108472138 | A | 8/2018 |
| CN | 108472395 | A | 8/2018 |
| CN | 108472424 | A | 8/2018 |
| CN | 207708246 | U | 8/2018 |
| CN | 207708250 | U | 8/2018 |
| CN | 105407937 | B | 9/2018 |
| CN | 105902298 | B | 9/2018 |
| CN | 106420113 | B | 9/2018 |
| CN | 106510902 | B | 9/2018 |
| CN | 108525039 | A | 9/2018 |
| CN | 108525040 | A | 9/2018 |
| CN | 108601653 | A | 9/2018 |
| CN | 108601872 | A | 9/2018 |
| CN | 108601874 | A | 9/2018 |
| CN | 108601875 | A | 9/2018 |
| CN | 207924984 | U | 9/2018 |
| CN | 106377810 | B | 10/2018 |
| EP | 96495 | B1 | 9/1986 |
| EP | 79373 | B1 | 12/1986 |
| EP | 54049 | B1 | 1/1988 |
| EP | 292510 | A4 | 8/1989 |
| EP | 167562 | B1 | 4/1990 |
| EP | 230532 | B1 | 9/1990 |
| EP | 241950 | B1 | 12/1990 |
| EP | 129779 | B1 | 4/1991 |
| EP | 202649 | B1 | 8/1991 |
| EP | 445782 | A1 | 9/1991 |
| EP | 464714 | A1 | 1/1992 |
| EP | 293592 | B1 | 11/1992 |
| EP | 297723 | B1 | 8/1993 |
| EP | 396575 | B1 | 3/1994 |
| EP | 397668 | B1 | 3/1994 |
| EP | 593574 | A1 | 4/1994 |
| EP | 378251 | B1 | 6/1994 |
| EP | 605621 | A1 | 7/1994 |
| EP | 467999 | B1 | 8/1994 |
| EP | 350282 | B1 | 11/1994 |
| EP | 478635 | B1 | 12/1994 |
| EP | 397720 | B1 | 3/1995 |
| EP | 421558 | B1 | 4/1995 |
| EP | 364799 | B1 | 5/1995 |
| EP | 660726 | A1 | 7/1995 |
| EP | 672386 | A1 | 9/1995 |
| EP | 349581 | B1 | 1/1996 |
| EP | 464973 | B1 | 1/1996 |
| EP | 505270 | B1 | 1/1996 |
| EP | 480101 | B1 | 5/1996 |
| EP | 583781 | B1 | 5/1996 |
| EP | 583012 | B1 | 7/1996 |
| EP | 756500 | A1 | 2/1997 |
| EP | 0764448 | A2 | 3/1997 |
| EP | 767318 | A2 | 4/1997 |
| EP | 788808 | A2 | 8/1997 |
| EP | 799060 | A1 | 10/1997 |
| EP | 823567 | A1 | 2/1998 |
| EP | 832357 | A1 | 4/1998 |
| EP | 841917 | A1 | 5/1998 |
| EP | 560000 | B1 | 9/1998 |
| EP | 879012 | A1 | 11/1998 |
| EP | 925078 | A1 | 6/1999 |
| EP | 807141 | B1 | 7/1999 |
| EP | 681654 | B1 | 9/1999 |
| EP | 958066 | A1 | 11/1999 |
| EP | 964718 | A1 | 12/1999 |
| EP | 725657 | B1 | 2/2000 |
| EP | 986409 | A1 | 3/2000 |
| EP | 1007140 | A1 | 6/2000 |
| EP | 1009466 | A1 | 6/2000 |
| EP | 1027898 | A1 | 8/2000 |
| EP | 1032437 | A1 | 9/2000 |
| EP | 1045708 | A1 | 10/2000 |
| EP | 1059885 | A2 | 12/2000 |
| EP | 746712 | B1 | 10/2001 |
| EP | 1139862 | A1 | 10/2001 |
| EP | 1147317 | A1 | 10/2001 |
| EP | 1148900 | A1 | 10/2001 |
| EP | 699447 | B1 | 11/2001 |
| EP | 591896 | B1 | 2/2002 |
| EP | 731664 | B1 | 2/2002 |
| EP | 797734 | B1 | 2/2002 |
| EP | 1217954 | A1 | 7/2002 |
| EP | 1231981 | A1 | 8/2002 |
| EP | 950057 | B1 | 11/2002 |
| EP | 751769 | B1 | 1/2003 |
| EP | 1278461 | A1 | 1/2003 |
| EP | 860046 | B1 | 2/2003 |
| EP | 597881 | B2 | 3/2003 |
| EP | 732949 | B1 | 3/2003 |
| EP | 814701 | B1 | 4/2003 |
| EP | 898479 | B1 | 5/2003 |
| EP | 905379 | B1 | 5/2003 |
| EP | 655625 | B1 | 7/2003 |
| EP | 764448 | B1 | 7/2003 |
| EP | 768091 | B1 | 7/2003 |
| EP | 825888 | B1 | 12/2003 |
| EP | 1379197 | A1 | 1/2004 |
| EP | 1382366 | A1 | 1/2004 |
| EP | 868145 | B1 | 2/2004 |
| EP | 895480 | B1 | 5/2004 |
| EP | 1441777 | A2 | 8/2004 |
| EP | 916359 | B1 | 9/2004 |
| EP | 1482999 | A1 | 12/2004 |
| EP | 1291027 | B1 | 3/2005 |
| EP | 877633 | B1 | 7/2005 |
| EP | 611228 | B2 | 8/2005 |
| EP | 1212516 | B1 | 10/2005 |
| EP | 1597457 | A2 | 11/2005 |
| EP | 1261385 | B1 | 2/2006 |

(56) References Cited

FOREIGN PATENT DOCUMENTS

| | | | |
|---|---|---|---|
| EP | 1648309 | A1 | 4/2006 |
| EP | 1354606 | B1 | 6/2006 |
| EP | 1663081 | A1 | 6/2006 |
| EP | 1321166 | B1 | 7/2006 |
| EP | 1191956 | B1 | 9/2006 |
| EP | 1722767 | A2 | 11/2006 |
| EP | 1070510 | B1 | 1/2007 |
| EP | 1317295 | B1 | 1/2007 |
| EP | 1327455 | B1 | 1/2007 |
| EP | 1776095 | A1 | 4/2007 |
| EP | 1141670 | B1 | 7/2007 |
| EP | 1807148 | A2 | 7/2007 |
| EP | 1827448 | A1 | 9/2007 |
| EP | 1374928 | B1 | 12/2007 |
| EP | 1877133 | A2 | 1/2008 |
| EP | 1379294 | B1 | 5/2008 |
| EP | 1930034 | A1 | 6/2008 |
| EP | 1318848 | B1 | 7/2008 |
| EP | 1356859 | B1 | 8/2008 |
| EP | 1955725 | A2 | 8/2008 |
| EP | 2058017 | A2 | 5/2009 |
| EP | 1731957 | B1 | 8/2009 |
| EP | 1173238 | B1 | 10/2009 |
| EP | 2043553 | B1 | 3/2010 |
| EP | 2158491 | A2 | 3/2010 |
| EP | 2178580 | A2 | 4/2010 |
| EP | 2182844 | A1 | 5/2010 |
| EP | 2194278 | A1 | 6/2010 |
| EP | 1471952 | B1 | 7/2010 |
| EP | 2207578 | A1 | 7/2010 |
| EP | 2216059 | A1 | 8/2010 |
| EP | 2218469 | A1 | 8/2010 |
| EP | 2219699 | A1 | 8/2010 |
| EP | 2222635 | A2 | 9/2010 |
| EP | 2222788 | A1 | 9/2010 |
| EP | 2229965 | A1 | 9/2010 |
| EP | 2235204 | A1 | 10/2010 |
| EP | 1280581 | B1 | 11/2010 |
| EP | 2246078 | A1 | 11/2010 |
| EP | 2248544 | A1 | 11/2010 |
| EP | 2252337 | A1 | 11/2010 |
| EP | 2266640 | A1 | 12/2010 |
| EP | 2269670 | A1 | 1/2011 |
| EP | 2297583 | A2 | 3/2011 |
| EP | 2298371 | A1 | 3/2011 |
| EP | 2298372 | A1 | 3/2011 |
| EP | 2298373 | A1 | 3/2011 |
| EP | 2299119 | A1 | 3/2011 |
| EP | 1464348 | B1 | 4/2011 |
| EP | 2314330 | A1 | 4/2011 |
| EP | 2314331 | A1 | 4/2011 |
| EP | 2338539 | A1 | 6/2011 |
| EP | 2338540 | A1 | 6/2011 |
| EP | 2338541 | A1 | 6/2011 |
| EP | 1654027 | B1 | 7/2011 |
| EP | 2343091 | A1 | 7/2011 |
| EP | 2347778 | A1 | 7/2011 |
| EP | 1812094 | B1 | 8/2011 |
| EP | 2349385 | A1 | 8/2011 |
| EP | 2353626 | A1 | 8/2011 |
| EP | 2356458 | A1 | 8/2011 |
| EP | 2363157 | A1 | 9/2011 |
| EP | 2366412 | A2 | 9/2011 |
| EP | 1907049 | B1 | 11/2011 |
| EP | 2388027 | A1 | 11/2011 |
| EP | 2388029 | A1 | 11/2011 |
| EP | 2399639 | A1 | 12/2011 |
| EP | 1514571 | B1 | 1/2012 |
| EP | 2407185 | A1 | 1/2012 |
| EP | 2407186 | A1 | 1/2012 |
| EP | 2407187 | A1 | 1/2012 |
| EP | 2422735 | A1 | 2/2012 |
| EP | 2322600 | B1 | 3/2012 |
| EP | 2429603 | A2 | 3/2012 |
| EP | 2459269 | A1 | 6/2012 |
| EP | 2497521 | A1 | 9/2012 |
| EP | 2140892 | B1 | 10/2012 |
| EP | 2505228 | A1 | 10/2012 |
| EP | 2150811 | B1 | 1/2013 |
| EP | 1833529 | B1 | 2/2013 |
| EP | 2554191 | A1 | 2/2013 |
| EP | 2277463 | B1 | 3/2013 |
| EP | 2564771 | A1 | 3/2013 |
| EP | 2151257 | B1 | 4/2013 |
| EP | 2575922 | A2 | 4/2013 |
| EP | 1623730 | B1 | 5/2013 |
| EP | 2606919 | A1 | 6/2013 |
| EP | 2606920 | A1 | 6/2013 |
| EP | 2607712 | A1 | 6/2013 |
| EP | 1919550 | B1 | 7/2013 |
| EP | 2620173 | A1 | 7/2013 |
| EP | 1331017 | B1 | 8/2013 |
| EP | 2101840 | B1 | 9/2013 |
| EP | 2401003 | B1 | 10/2013 |
| EP | 2654878 | A2 | 10/2013 |
| EP | 2654883 | A2 | 10/2013 |
| EP | 2671083 | A1 | 12/2013 |
| EP | 1412001 | B1 | 1/2014 |
| EP | 1942965 | B1 | 1/2014 |
| EP | 2231222 | B1 | 2/2014 |
| EP | 2697890 | A2 | 2/2014 |
| EP | 1017433 | B1 | 3/2014 |
| EP | 1629855 | B1 | 4/2014 |
| EP | 2736581 | A2 | 6/2014 |
| EP | 2744460 | A1 | 6/2014 |
| EP | 2745869 | A1 | 6/2014 |
| EP | 1485613 | B1 | 7/2014 |
| EP | 1605988 | B1 | 8/2014 |
| EP | 2792696 | A2 | 10/2014 |
| EP | 2195043 | B1 | 12/2014 |
| EP | 1962949 | B1 | 2/2015 |
| EP | 2030641 | B1 | 2/2015 |
| EP | 2643927 | B1 | 4/2015 |
| EP | 2868331 | A2 | 5/2015 |
| EP | 1460972 | B1 | 6/2015 |
| EP | 2150569 | B1 | 6/2015 |
| EP | 2152783 | B1 | 6/2015 |
| EP | 2345439 | B1 | 6/2015 |
| EP | 2895215 | A2 | 7/2015 |
| EP | 1761306 | B1 | 8/2015 |
| EP | 2663347 | B1 | 8/2015 |
| EP | 2209508 | B1 | 9/2015 |
| EP | 2915129 | A1 | 9/2015 |
| EP | 2920421 | A2 | 9/2015 |
| EP | 2533732 | B1 | 11/2015 |
| EP | 1317305 | B1 | 12/2015 |
| EP | 1339443 | B1 | 1/2016 |
| EP | 2967284 | A1 | 1/2016 |
| EP | 2967547 | A1 | 1/2016 |
| EP | 2984731 | A1 | 2/2016 |
| EP | 2167158 | B1 | 3/2016 |
| EP | 2061531 | B1 | 4/2016 |
| EP | 2519274 | B1 | 4/2016 |
| EP | 1996252 | B1 | 5/2016 |
| EP | 2464395 | B1 | 5/2016 |
| EP | 3047873 | A1 | 7/2016 |
| EP | 3047911 | A1 | 7/2016 |
| EP | 2643053 | B1 | 8/2016 |
| EP | 2734251 | B1 | 8/2016 |
| EP | 3050537 | A1 | 8/2016 |
| EP | 1942128 | B1 | 9/2016 |
| EP | 2099509 | B1 | 9/2016 |
| EP | 2719403 | B1 | 9/2016 |
| EP | 3072210 | A1 | 9/2016 |
| EP | 3072211 | A1 | 9/2016 |
| EP | 2405140 | B1 | 10/2016 |
| EP | 2197507 | B1 | 11/2016 |
| EP | 2538086 | B1 | 11/2016 |
| EP | 3086834 | A1 | 11/2016 |
| EP | 2806911 | B1 | 12/2016 |
| EP | 3110468 | A1 | 1/2017 |
| EP | 3113808 | A1 | 1/2017 |
| EP | 3119452 | A1 | 1/2017 |
| EP | 3120811 | A2 | 1/2017 |

(56) References Cited

FOREIGN PATENT DOCUMENTS

| | | | |
|---|---|---|---|
| EP | 3131595 | A1 | 2/2017 |
| EP | 3131596 | A1 | 2/2017 |
| EP | 3131599 | A1 | 2/2017 |
| EP | 3131600 | A1 | 2/2017 |
| EP | 3131615 | A1 | 2/2017 |
| EP | 2585129 | B1 | 3/2017 |
| EP | 2594799 | B1 | 3/2017 |
| EP | 3146987 | A1 | 3/2017 |
| EP | 3157597 | A1 | 4/2017 |
| EP | 3173110 | A1 | 5/2017 |
| EP | 2825107 | B1 | 7/2017 |
| EP | 3185924 | A1 | 7/2017 |
| EP | 3185925 | A1 | 7/2017 |
| EP | 3189526 | A1 | 7/2017 |
| EP | 3191164 | A1 | 7/2017 |
| EP | 2618001 | B1 | 8/2017 |
| EP | 3197602 | A1 | 8/2017 |
| EP | 3198677 | A1 | 8/2017 |
| EP | 3204989 | A1 | 8/2017 |
| EP | 3212250 | A1 | 9/2017 |
| EP | 3219339 | A1 | 9/2017 |
| EP | 3223880 | A1 | 10/2017 |
| EP | 3232948 | A1 | 10/2017 |
| EP | 1885409 | B1 | 11/2017 |
| EP | 2292282 | B1 | 11/2017 |
| EP | 2945661 | B1 | 11/2017 |
| EP | 3238764 | A1 | 11/2017 |
| EP | 3244814 | A1 | 11/2017 |
| EP | 3247420 | A1 | 11/2017 |
| EP | 3247421 | A2 | 11/2017 |
| EP | 3248628 | A1 | 11/2017 |
| EP | 2136861 | B1 | 12/2017 |
| EP | 3256183 | A1 | 12/2017 |
| EP | 3256184 | A1 | 12/2017 |
| EP | 3256185 | A1 | 12/2017 |
| EP | 3256186 | A1 | 12/2017 |
| EP | 3007742 | B1 | 1/2018 |
| EP | 3277200 | A1 | 2/2018 |
| EP | 3287155 | A1 | 2/2018 |
| EP | 2482916 | B1 | 3/2018 |
| EP | 2948202 | B1 | 3/2018 |
| EP | 3294367 | A1 | 3/2018 |
| EP | 2945662 | B1 | 4/2018 |
| EP | 3310409 | A1 | 4/2018 |
| EP | 3222301 | B1 | 5/2018 |
| EP | 3222302 | B1 | 5/2018 |
| EP | 3313471 | A1 | 5/2018 |
| EP | 3324840 | A1 | 5/2018 |
| EP | 3325035 | A1 | 5/2018 |
| EP | 3326487 | A1 | 5/2018 |
| EP | 1789129 | B1 | 6/2018 |
| EP | 1990358 | B1 | 6/2018 |
| EP | 3329953 | A1 | 6/2018 |
| EP | 3335647 | A2 | 6/2018 |
| EP | 3341069 | A1 | 7/2018 |
| EP | 3349839 | A1 | 7/2018 |
| EP | 2219698 | B1 | 8/2018 |
| EP | 2890420 | B1 | 8/2018 |
| EP | 3352808 | A1 | 8/2018 |
| EP | 3352835 | A1 | 8/2018 |
| EP | 3360233 | A1 | 8/2018 |
| EP | 3360515 | A1 | 8/2018 |
| EP | 1534381 | B1 | 9/2018 |
| EP | 3108909 | B1 | 9/2018 |
| EP | 3377001 | A1 | 9/2018 |
| EP | 3377002 | A1 | 9/2018 |
| EP | 3377134 | A1 | 9/2018 |
| EP | 3377135 | A1 | 9/2018 |
| EP | 3377136 | A1 | 9/2018 |
| EP | 2249746 | B1 | 10/2018 |
| EP | 2988795 | B1 | 10/2018 |
| EP | 3383300 | A1 | 10/2018 |
| EP | 3383448 | A1 | 10/2018 |
| EP | 3388005 | A1 | 10/2018 |
| EP | 3542835 | A1 | 9/2019 |

| | | | |
|---|---|---|---|
| FR | 2331995 | A2 | 6/1977 |
| JP | 64-52472 | A | 2/1989 |
| JP | 02289241 | A | 11/1990 |
| JP | 04176471 | A | 6/1992 |
| JP | 04224760 | A | 8/1992 |
| JP | H05-078996 | U | 10/1993 |
| JP | H11-062856 | A | 3/1999 |
| JP | H11-244376 | A | 9/1999 |
| JP | 2000102604 | A | 4/2000 |
| JP | 2000107281 | A | 4/2000 |
| JP | 2000283062 | A | 10/2000 |
| JP | 03131696 | B2 | 2/2001 |
| JP | 2001061957 | A | 3/2001 |
| JP | 2001090687 | A | 4/2001 |
| JP | 03174338 | B2 | 6/2001 |
| JP | 2001173402 | A | 6/2001 |
| JP | 2001523983 | A | 11/2001 |
| JP | 03278160 | B2 | 4/2002 |
| JP | 2002191123 | A | 7/2002 |
| JP | 03313061 | B2 | 8/2002 |
| JP | 2003047656 | A | 2/2003 |
| JP | 2003070906 | A | 3/2003 |
| JP | 2003205030 | A | 7/2003 |
| JP | 2004011525 | A | 1/2004 |
| JP | 2004016426 | A | 1/2004 |
| JP | 2004028102 | A | 1/2004 |
| JP | 2004073400 | A | 3/2004 |
| JP | 2004209240 | A | 7/2004 |
| JP | 2004278375 | A | 10/2004 |
| JP | 03612581 | B2 | 1/2005 |
| JP | 2005058617 | A | 3/2005 |
| JP | 2005192687 | A | 7/2005 |
| JP | 2005199076 | A | 7/2005 |
| JP | 2005348996 | A | 12/2005 |
| JP | 2006000631 | A | 1/2006 |
| JP | 03786289 | B2 | 6/2006 |
| JP | 03803417 | B2 | 8/2006 |
| JP | 2006280571 | A | 10/2006 |
| JP | 03854972 | B2 | 12/2006 |
| JP | 2007044302 | A | 2/2007 |
| JP | 2007075541 | A | 3/2007 |
| JP | 2007089607 | A | 4/2007 |
| JP | 2007089973 | A | 4/2007 |
| JP | 2007236564 | A | 9/2007 |
| JP | 04016441 | B2 | 12/2007 |
| JP | 04022372 | B2 | 12/2007 |
| JP | 2008018242 | A | 1/2008 |
| JP | 04051812 | B2 | 2/2008 |
| JP | 04072721 | B2 | 4/2008 |
| JP | 04077902 | B2 | 4/2008 |
| JP | 04084060 | B2 | 4/2008 |
| JP | 04086185 | B2 | 5/2008 |
| JP | 04121709 | B2 | 7/2008 |
| JP | 04163384 | B2 | 10/2008 |
| JP | 04179634 | B2 | 11/2008 |
| JP | 2008264586 | A | 11/2008 |
| JP | 04198986 | B2 | 12/2008 |
| JP | 2009090882 | A | 4/2009 |
| JP | 04279494 | B2 | 6/2009 |
| JP | 2009178570 | A | 8/2009 |
| JP | 2009254436 | A | 11/2009 |
| JP | 2009273214 | A | 11/2009 |
| JP | 04387106 | B2 | 12/2009 |
| JP | 04391680 | B2 | 12/2009 |
| JP | 04440499 | B2 | 3/2010 |
| JP | 04467187 | B2 | 5/2010 |
| JP | 04468965 | B2 | 5/2010 |
| JP | 04484320 | B2 | 6/2010 |
| JP | 2010158532 | A | 7/2010 |
| JP | 04548450 | B2 | 9/2010 |
| JP | 2010246941 | A | 11/2010 |
| JP | 04646393 | B2 | 3/2011 |
| JP | 04674978 | B2 | 4/2011 |
| JP | 2011072533 | A | 4/2011 |
| JP | 2011116765 | A | 6/2011 |
| JP | 04728351 | B2 | 7/2011 |
| JP | 04741242 | B2 | 8/2011 |
| JP | 2011161401 | A | 8/2011 |
| JP | 04795536 | B2 | 10/2011 |

(56) References Cited

FOREIGN PATENT DOCUMENTS

| | | | |
|---|---|---|---|
| JP | 04865825 | B2 | 2/2012 |
| JP | 04907028 | B2 | 3/2012 |
| JP | 04908737 | B2 | 4/2012 |
| JP | 04964854 | B2 | 7/2012 |
| JP | 04987999 | B2 | 8/2012 |
| JP | 05047447 | B2 | 10/2012 |
| JP | 05048749 | B2 | 10/2012 |
| JP | 05093869 | B2 | 12/2012 |
| JP | 05102033 | B2 | 12/2012 |
| JP | 05185629 | B2 | 4/2013 |
| JP | 05193059 | B2 | 5/2013 |
| JP | 2013078564 | A | 5/2013 |
| JP | 2013192711 | A | 9/2013 |
| JP | 2014004303 | A | 1/2014 |
| JP | 05429714 | B2 | 2/2014 |
| JP | 2014091049 | A | 5/2014 |
| JP | 2014114784 | A | 6/2014 |
| JP | 05539484 | B2 | 7/2014 |
| JP | 05596974 | B2 | 10/2014 |
| JP | 05611948 | B2 | 10/2014 |
| JP | 05656835 | B2 | 1/2015 |
| JP | 05675786 | B2 | 2/2015 |
| JP | 05676118 | B2 | 2/2015 |
| JP | 05701848 | B2 | 4/2015 |
| JP | 05711245 | B2 | 4/2015 |
| JP | 05750492 | B2 | 7/2015 |
| JP | 05781597 | B2 | 9/2015 |
| JP | 2015159947 | A | 9/2015 |
| JP | 05894116 | B2 | 3/2016 |
| JP | 05894678 | B2 | 3/2016 |
| JP | 2016028764 | A | 3/2016 |
| JP | 2016182342 | A | 10/2016 |
| JP | 06034858 | B2 | 11/2016 |
| JP | 06038018 | B2 | 12/2016 |
| JP | 2016202553 | A | 12/2016 |
| JP | 2017035323 | A | 2/2017 |
| JP | 2017517306 | A | 6/2017 |
| JP | 2017127675 | A | 7/2017 |
| JP | 2017159083 | A | 9/2017 |
| JP | 06220867 | B2 | 10/2017 |
| JP | 06236451 | B2 | 11/2017 |
| JP | 2018020199 | A | 2/2018 |
| JP | 06295204 | B2 | 3/2018 |
| JP | 06329358 | B2 | 5/2018 |
| JP | 06339371 | B2 | 6/2018 |
| JP | 06345112 | B2 | 6/2018 |
| JP | 06353787 | B2 | 7/2018 |
| JP | 06382285 | B2 | 8/2018 |
| JP | 2018122146 | A | 8/2018 |
| JP | 2018523541 | A | 8/2018 |
| WO | WO87/002894 | A2 | 5/1987 |
| WO | WO88/009874 | A1 | 12/1988 |
| WO | WO92/002263 | A1 | 2/1992 |
| WO | WO92/003181 | A1 | 3/1992 |
| WO | WO96/14027 | A1 | 5/1995 |
| WO | WO95/031196 | A1 | 11/1995 |
| WO | WO96/016684 | A1 | 6/1996 |
| WO | WO98/042984 | A1 | 10/1998 |
| WO | WO00/019097 | A1 | 4/2000 |
| WO | WO00/027446 | A1 | 5/2000 |
| WO | WO00/035515 | A1 | 6/2000 |
| WO | WO01/017581 | A2 | 3/2001 |
| WO | WO01/019444 | A1 | 3/2001 |
| WO | WO01/041070 | A1 | 6/2001 |
| WO | WO01/074419 | A1 | 10/2001 |
| WO | WO01/087176 | A1 | 11/2001 |
| WO | WO01/095813 | A1 | 12/2001 |
| WO | WO02/47751 | A2 | 6/2002 |
| WO | WO02/053226 | A2 | 7/2002 |
| WO | WO02/070039 | A2 | 9/2002 |
| WO | WO02/072000 | A1 | 9/2002 |
| WO | WO02/081021 | A1 | 10/2002 |
| WO | WO03/024501 | A2 | 3/2003 |
| WO | WO03/061727 | A2 | 7/2003 |
| WO | WO03/094716 | A1 | 11/2003 |
| WO | WO03/103745 | A2 | 12/2003 |
| WO | WO2004/026394 | A1 | 4/2004 |
| WO | WO2004/034034 | A1 | 4/2004 |
| WO | WO2004/088480 | A2 | 10/2004 |
| WO | WO2004/098677 | A1 | 11/2004 |
| WO | WO2005/020848 | A2 | 3/2005 |
| WO | WO2005/033671 | A1 | 4/2005 |
| WO | WO2005/037348 | A1 | 4/2005 |
| WO | WO2005/054680 | A1 | 6/2005 |
| WO | WO2005/108796 | A1 | 11/2005 |
| WO | WO2006/040252 | A1 | 4/2006 |
| WO | WO2006/053384 | A1 | 5/2006 |
| WO | WO2006/081255 | A2 | 8/2006 |
| WO | WO2006/121698 | A2 | 11/2006 |
| WO | WO2007/008907 | A2 | 1/2007 |
| WO | WO2007/033933 | A1 | 3/2007 |
| WO | WO2007/053881 | A1 | 5/2007 |
| WO | WO2007/065408 | A2 | 6/2007 |
| WO | WO2007/092494 | A2 | 8/2007 |
| WO | WO2007/105842 | A1 | 9/2007 |
| WO | WO2007/146231 | A2 | 12/2007 |
| WO | WO2008/005747 | A2 | 1/2008 |
| WO | WO2008/008427 | A2 | 1/2008 |
| WO | WO2008/088874 | A2 | 7/2008 |
| WO | WO2008/102015 | A1 | 8/2008 |
| WO | WO2008/121143 | A1 | 10/2008 |
| WO | WO2008/121145 | A1 | 10/2008 |
| WO | WO2008/137237 | A2 | 11/2008 |
| WO | WO2008/140034 | A1 | 11/2008 |
| WO | WO2009/017549 | A1 | 2/2009 |
| WO | WO2009035581 | A1 | 3/2009 |
| WO | WO2009/046789 | A1 | 4/2009 |
| WO | WO2009/075668 | A2 | 6/2009 |
| WO | WO2009/096991 | A1 | 8/2009 |
| WO | WO2010/025411 | A2 | 3/2010 |
| WO | WO2010/119110 | A1 | 10/2010 |
| WO | WO2011/003043 | A1 | 1/2011 |
| WO | WO2011/024928 | A1 | 3/2011 |
| WO | WO2011/035925 | A1 | 3/2011 |
| WO | WO2011/039091 | A1 | 4/2011 |
| WO | WO2011/081629 | A1 | 7/2011 |
| WO | WO2011/082212 | A1 | 7/2011 |
| WO | WO2011/085040 | A1 | 7/2011 |
| WO | WO2011/117566 | A1 | 9/2011 |
| WO | WO2011/119060 | A2 | 9/2011 |
| WO | WO2012/037506 | A2 | 3/2012 |
| WO | WO2012/051454 | A2 | 4/2012 |
| WO | WO2012/064674 | A1 | 5/2012 |
| WO | WO2012/075152 | A1 | 6/2012 |
| WO | WO2012/075262 | A1 | 6/2012 |
| WO | WO2012/087811 | A2 | 6/2012 |
| WO | WO2012/094535 | A2 | 7/2012 |
| WO | WO2012/094641 | A2 | 7/2012 |
| WO | WO2012/096716 | A2 | 7/2012 |
| WO | WO2012/112129 | A1 | 8/2012 |
| WO | WO2013/034547 | A1 | 3/2013 |
| WO | WO2013/093058 | A1 | 6/2013 |
| WO | WO2013/127182 | A1 | 9/2013 |
| WO | WO2013/134319 | A1 | 9/2013 |
| WO | WO2013/148560 | A1 | 10/2013 |
| WO | WO2013/148697 | A1 | 10/2013 |
| WO | WO2014/070458 | A1 | 5/2014 |
| WO | WO2014/096408 | A1 | 6/2014 |
| WO | WO2014/106635 | A1 | 7/2014 |
| WO | WO2014/116639 | A1 | 7/2014 |
| WO | WO2014/142754 | A1 | 9/2014 |
| WO | WO2014/143593 | A1 | 9/2014 |
| WO | WO2014/164136 | A1 | 10/2014 |
| WO | WO2014/164292 | A1 | 10/2014 |
| WO | WO2014/166128 | A1 | 10/2014 |
| WO | WO2014/169023 | A2 | 10/2014 |
| WO | WO2015/119705 | A1 | 8/2015 |
| WO | WO2015/160943 | A1 | 10/2015 |
| WO | WO2015/160979 | A1 | 10/2015 |
| WO | WO2015/171156 | A1 | 11/2015 |
| WO | WO2015/175711 | A1 | 11/2015 |
| WO | WO2015/175718 | A1 | 11/2015 |
| WO | WO2015/177793 | A2 | 11/2015 |
| WO | WO2015/187659 | A2 | 12/2015 |

(56) References Cited

FOREIGN PATENT DOCUMENTS

| | | | |
|---|---|---|---|
| WO | WO2016/100600 | A2 | 6/2016 |
| WO | WO2016/113266 | A1 | 7/2016 |
| WO | WO2016/116630 | A2 | 7/2016 |
| WO | WO2017/001358 | A1 | 1/2017 |
| WO | WO2017/011257 | A1 | 1/2017 |
| WO | WO2017/032751 | A1 | 3/2017 |
| WO | WO2017/048733 | A1 | 3/2017 |
| WO | WO2017/060254 | A1 | 4/2017 |
| WO | WO2017/060257 | A1 | 4/2017 |
| WO | WO2017/075322 | A1 | 5/2017 |
| WO | WO2017/087380 | A1 | 5/2017 |
| WO | WO2017/120453 | A1 | 7/2017 |
| WO | WO2017/133425 | A1 | 8/2017 |
| WO | WO2017/134657 | A1 | 8/2017 |
| WO | WO2017/139113 | A1 | 8/2017 |
| WO | WO2017/139246 | A1 | 8/2017 |
| WO | WO2017/147082 | A1 | 8/2017 |
| WO | WO2017/147103 | A1 | 8/2017 |
| WO | WO2017/147291 | A1 | 8/2017 |
| WO | WO2017/151987 | A1 | 9/2017 |
| WO | WO2017/156386 | A1 | 9/2017 |
| WO | WO2017/159849 | A1 | 9/2017 |
| WO | WO2017/165372 | A1 | 9/2017 |
| WO | WO2017/178904 | A1 | 10/2017 |
| WO | WO2017/183124 | A1 | 10/2017 |
| WO | WO2017/190155 | A2 | 11/2017 |
| WO | WO2017/192119 | A1 | 11/2017 |
| WO | WO2017/196271 | A1 | 11/2017 |
| WO | WO2017/205909 | A1 | 12/2017 |
| WO | WO2017/210318 | A2 | 12/2017 |
| WO | WO2017/214118 | A1 | 12/2017 |
| WO | WO2017/214183 | A1 | 12/2017 |
| WO | WO2017/217946 | A1 | 12/2017 |
| WO | WO2018/007120 | A1 | 1/2018 |
| WO | WO2018/007471 | A1 | 1/2018 |
| WO | WO2018/017678 | A1 | 1/2018 |
| WO | WO2018/017683 | A1 | 1/2018 |
| WO | WO2018/017716 | A1 | 1/2018 |
| WO | WO2018/026764 | A1 | 2/2018 |
| WO | WO2018/026769 | A1 | 2/2018 |
| WO | WO2018/031741 | A1 | 2/2018 |
| WO | WO2018/035069 | A1 | 2/2018 |
| WO | WO2018/039124 | A1 | 3/2018 |
| WO | WO2018/039326 | A1 | 3/2018 |
| WO | WO2018/041963 | A1 | 3/2018 |
| WO | WO2018/045299 | A1 | 3/2018 |
| WO | WO2018/051091 | A1 | 3/2018 |
| WO | WO2018/052482 | A1 | 3/2018 |
| WO | WO2018/057482 | A1 | 3/2018 |
| WO | WO2018/057563 | A1 | 3/2018 |
| WO | WO2018/061002 | A1 | 4/2018 |
| WO | WO2018/064437 | A1 | 4/2018 |
| WO | WO2018/067410 | A1 | 4/2018 |
| WO | WO2018/073150 | A1 | 4/2018 |
| WO | WO2018/078370 | A1 | 5/2018 |
| WO | WO2018/078615 | A1 | 5/2018 |
| WO | WO2018/082987 | A1 | 5/2018 |
| WO | WO2018/088939 | A1 | 5/2018 |
| WO | WO2018/089970 | A1 | 5/2018 |
| WO | WO2018/093663 | A1 | 5/2018 |
| WO | WO2018/096531 | A1 | 5/2018 |
| WO | WO2018/118756 | A1 | 6/2018 |
| WO | WO2018/132181 | A1 | 7/2018 |
| WO | WO2018/132182 | A1 | 7/2018 |
| WO | WO2018/135477 | A1 | 7/2018 |
| WO | WO2018/135478 | A1 | 7/2018 |
| WO | WO2018/136592 | A2 | 7/2018 |
| WO | WO2018/139508 | A1 | 8/2018 |
| WO | WO2018/145434 | A1 | 8/2018 |
| WO | WO2018/146045 | A1 | 8/2018 |
| WO | WO2018/146170 | A1 | 8/2018 |
| WO | WO2018/146173 | A1 | 8/2018 |
| WO | WO2018/146177 | A1 | 8/2018 |
| WO | WO2018/148456 | A1 | 8/2018 |
| WO | WO2018/156524 | A1 | 8/2018 |
| WO | WO2018/158636 | A1 | 9/2018 |
| WO | WO2018/177344 | A1 | 10/2018 |
| WO | WO2018/178939 | A1 | 10/2018 |
| WO | WO2018/183128 | A1 | 10/2018 |
| WO | WO2018/187576 | A2 | 10/2018 |
| WO | WO2018/226991 | A1 | 12/2018 |
| WO | WO2019/094963 | A1 | 5/2019 |
| WO | WO2019/138350 | A2 | 7/2019 |
| WO | WO2019/158996 | A1 | 8/2019 |
| WO | WO2019/191851 | A1 | 9/2019 |
| WO | WO2019/194956 | A1 | 10/2019 |
| WO | WO2019/229222 | A1 | 12/2019 |
| WO | WO2020/028537 | A1 | 2/2020 |
| WO | WO2020/0234785 | A1 | 11/2020 |
| WO | WO2020/247612 | A1 | 12/2020 |
| WO | WO2021/026469 | A1 | 2/2021 |
| WO | WO2021/026472 | A1 | 2/2021 |
| WO | WO2021/062260 | A1 | 4/2021 |
| WO | WO2021/062265 | A1 | 4/2021 |
| WO | WO2021/062270 | A1 | 4/2021 |
| WO | WO2021/119478 | A1 | 6/2021 |
| WO | WO2021/127503 | A1 | 6/2021 |
| WO | WO2021/158967 | A1 | 8/2021 |
| WO | WO2021/195617 | A1 | 9/2021 |
| WO | WO2021/222403 | A1 | 11/2021 |
| WO | WO2021/231574 | A1 | 11/2021 |
| WO | WO2021/243263 | A1 | 12/2021 |

OTHER PUBLICATIONS

Robinson et al.; U.S. Appl. No. 17/784,758 Descending aorta and vena cava blood pumps, filed Jun. 13, 2022.

Jagani et al.; Dual-propeller cavopulmonary pump for assisting patients with hypoplastic right ventricle; ASAIO Joumal (American Society for Artificial Internal Organs); 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Calomeni et al.; U.S. Appl. No. 16/927,705 entitled "Intravascular blood pumps and methods of manufacture and use," filed Jul. 13, 2020.

Brandt; U.S. Appl. No. 16/936,160 entitled "Intravascular blood pumps with struts and methods of use and manufacture," filed Jul. 22, 2020.

Hildebrand et al.; U.S. Appl. No. 17/615,685 entitled "Catheter blood pumps and methods of use and manufacture," filed Dec. 1, 2021.

Salahieh et al.; U.S. Appl. No. 17/552,311 entitled "Intravascular blood pumps and methods of use and manufacture," filed Dec. 15, 2021.

Calomeni et al.; U.S. Appl. No. 17/033,455 entitled "Catheter blood pump and collapsible blood conduits," filed Sep. 25, 2020.

Wallin et al.; U.S. Appl. No. 17/033,482 entitled "Intravascular blood pump system and methods of use and control thereof," filed Sep. 25, 2020.

Dhaliwal et al.; U.S. Appl. No. 17/033,493 entitled "Catheter blood pumps and collapsible pump housings," filed Sep. 25, 2020.

Saul et al.; U.S. Appl. No. 17/264,927 entitled "Intravascular blood pumps and methods of use," filed Feb. 1, 2021.

Hildebrand et al.; U.S. Appl. No. 17/632,550 entitled Catheter blood pumps and impellers, filed Feb. 3, 2022.

Ryan et al.; U.S. Appl. No. 17/632,554 entitled "Catheter blood pump delivery, guiding systems and methods of use," filed Feb. 3, 2022.

Hildebrand et al.; U.S. Appl. No. 17/907,321 entitled "Intravascular blood pumps," filed Sep. 26, 2022.

Salahieh et al.; U.S. Appl. No. 18/047,076 entitled "Intravascular fluid movement devices, systems, and methods of use," filed Oct. 17, 2022.

(56) References Cited

OTHER PUBLICATIONS

Merchant et al.; U.S. Appl. No. 17/997,489 entitled "Intravascular blood pumps and control thereof," filed Oct. 28, 2022.
Saul et al.; U.S. Appl. No. 17/998,614 entitled "Inflatable medical devices, methods of manufacture and use," filed Nov. 11, 2022.
Ryan et al.; U.S. Appl. No. 17/998,624 entitled "Catheter blood pumps and collapsible pump housings," filed 111/11/2022.
Salahieh et al.; U.S. Appl. No. 18/342,634 entitled "Intravascular fluid movement devices, systems, and methods of use," filed Jun. 27, 2023.
Calomeni et al.; U.S. Appl. No. 18/614,131 entitled "Intravascular blood pumps and methods of manufacture and use," filed Mar. 22, 2024.
Ryan et al.; U.S. Appl. No. 18/552,430 entitled "Catheter blood pumps," filed Sep. 25, 2023.
Ryan et al.; U.S. Appl. No. 18/554,746 entitled "catheter blood pump distal bearing assemblies," filed Oct. 10, 2023.
Calomeni et al.; U.S. Appl. No. 18/549,128 entitled "Intravascular blood pumps and pumps with expandable scaffolds," filed Sep. 5, 2024.
Brandt et al.; U.S. Appl. No. 18/554,756 entitled "Catheter blood pump shrouds and assembly thereof," filed Oct. 10, 2023.
Ryan et al.; U.S. Appl. No. 18/559,231 entitled "Intravascular blood pump outflow flow disruptor," filed Nov. 6, 2023.

* cited by examiner

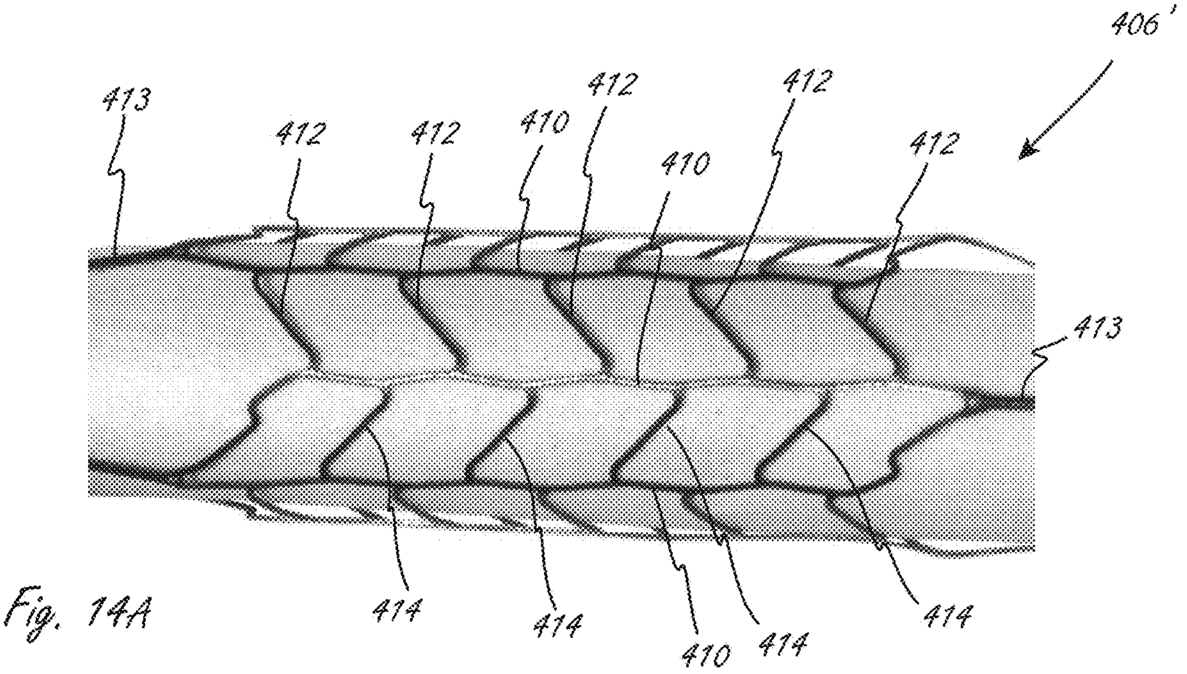
Fig. 14A
Fig. 14B
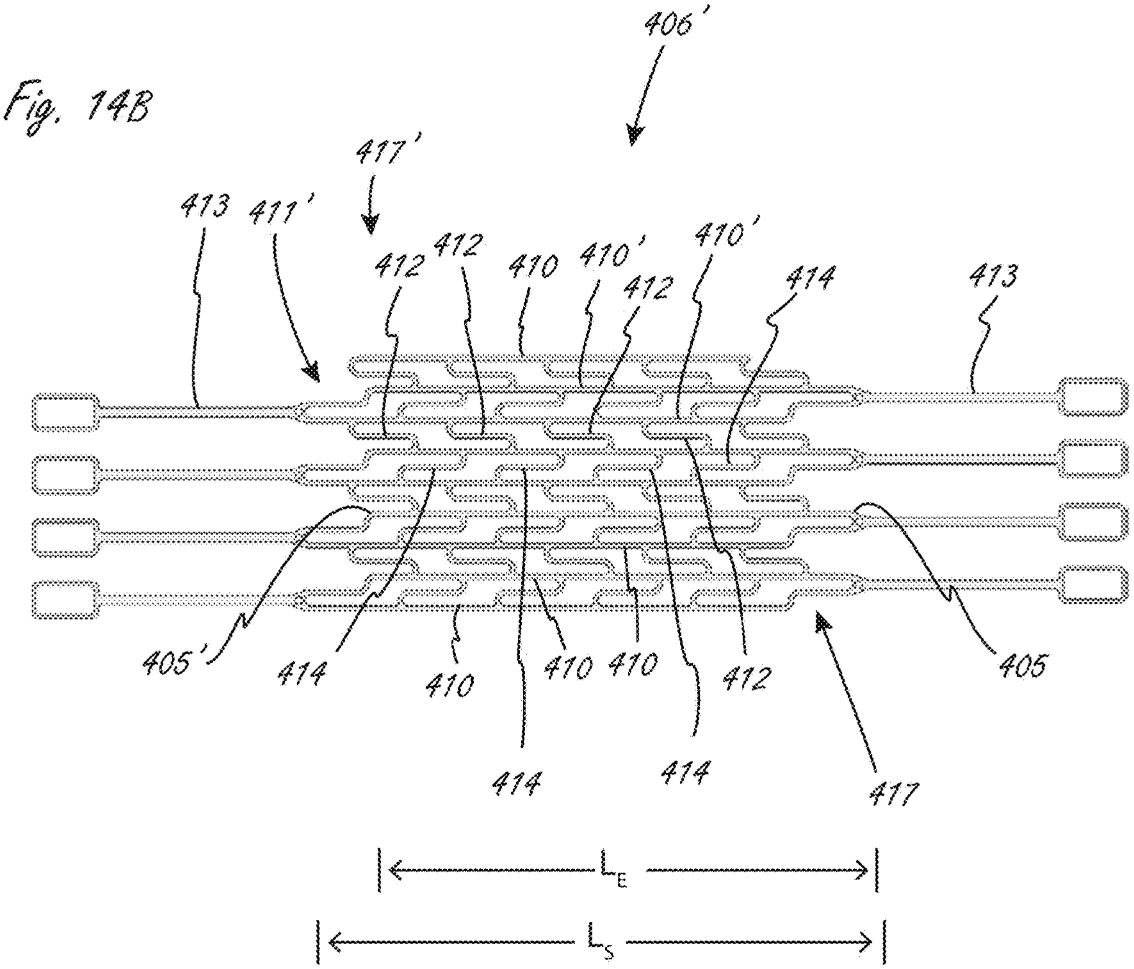

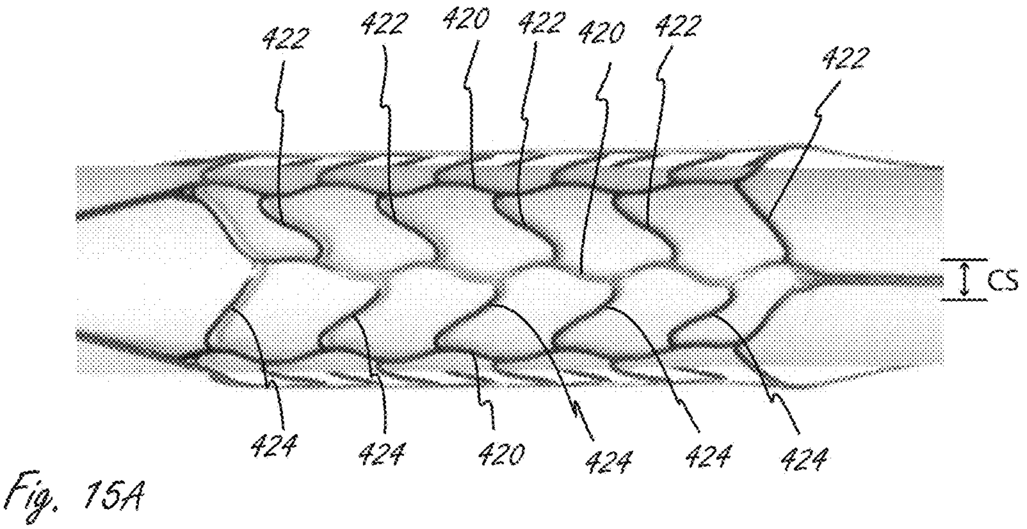
Fig. 15A
Fig. 15B
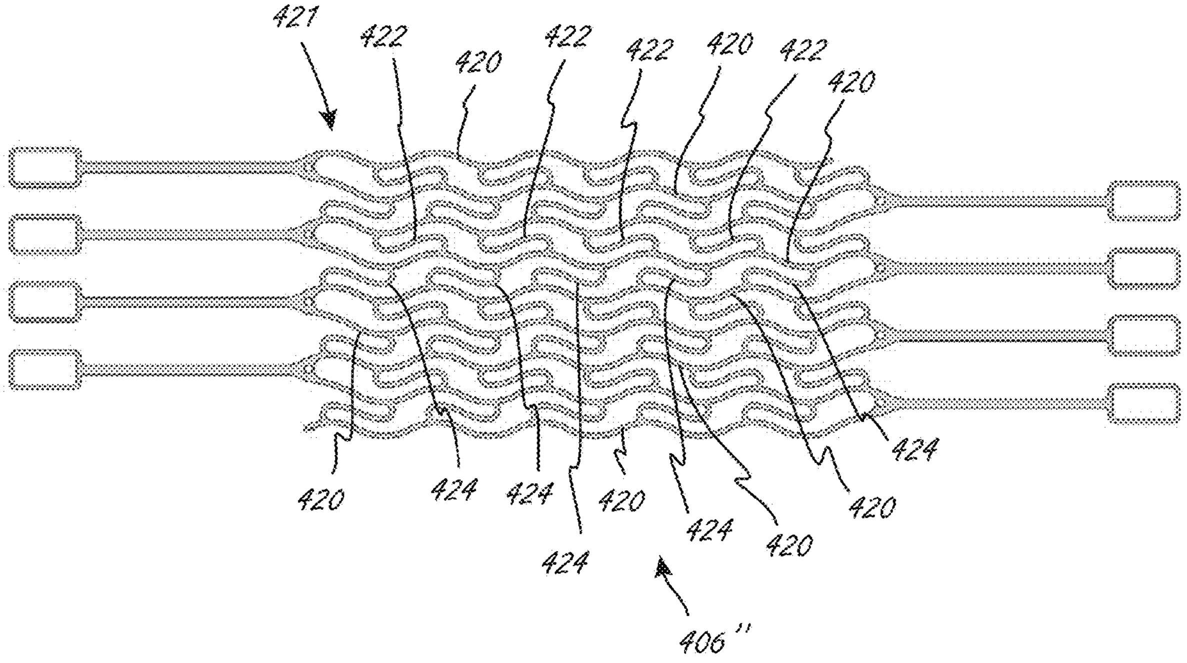

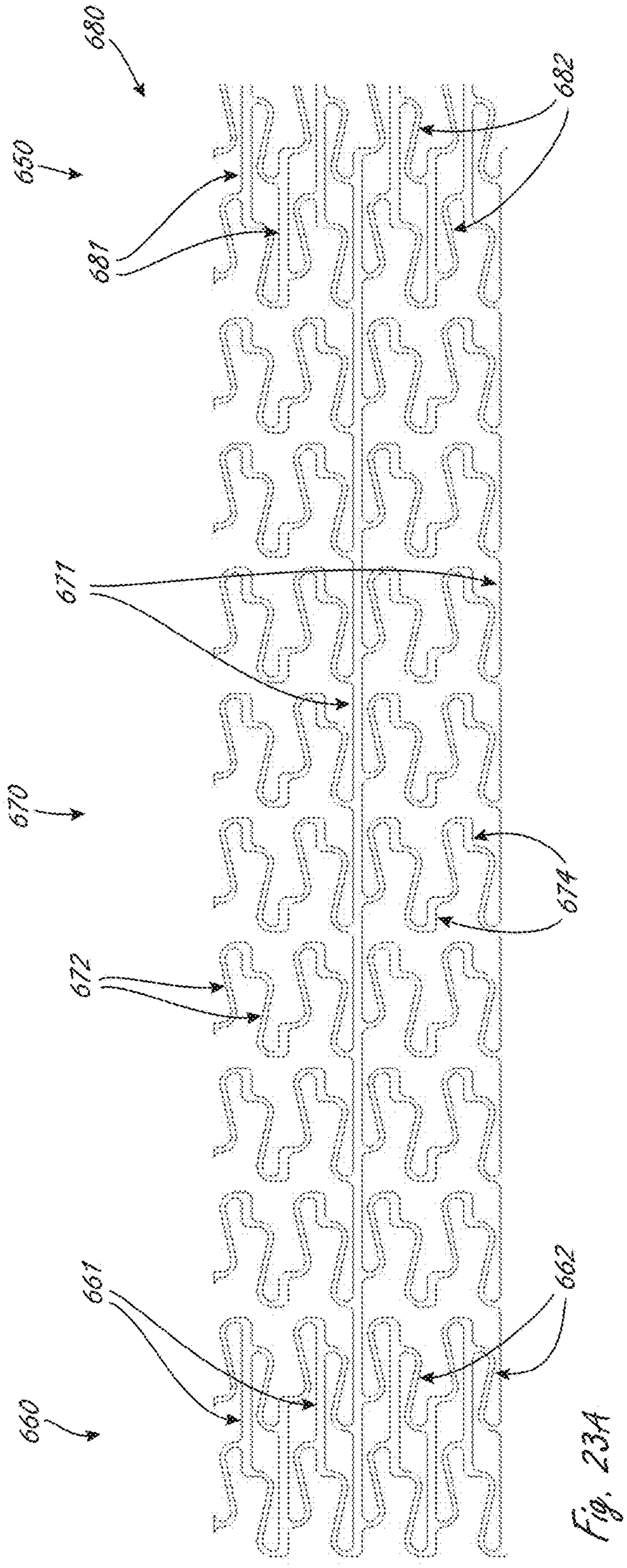
Fig. 23A
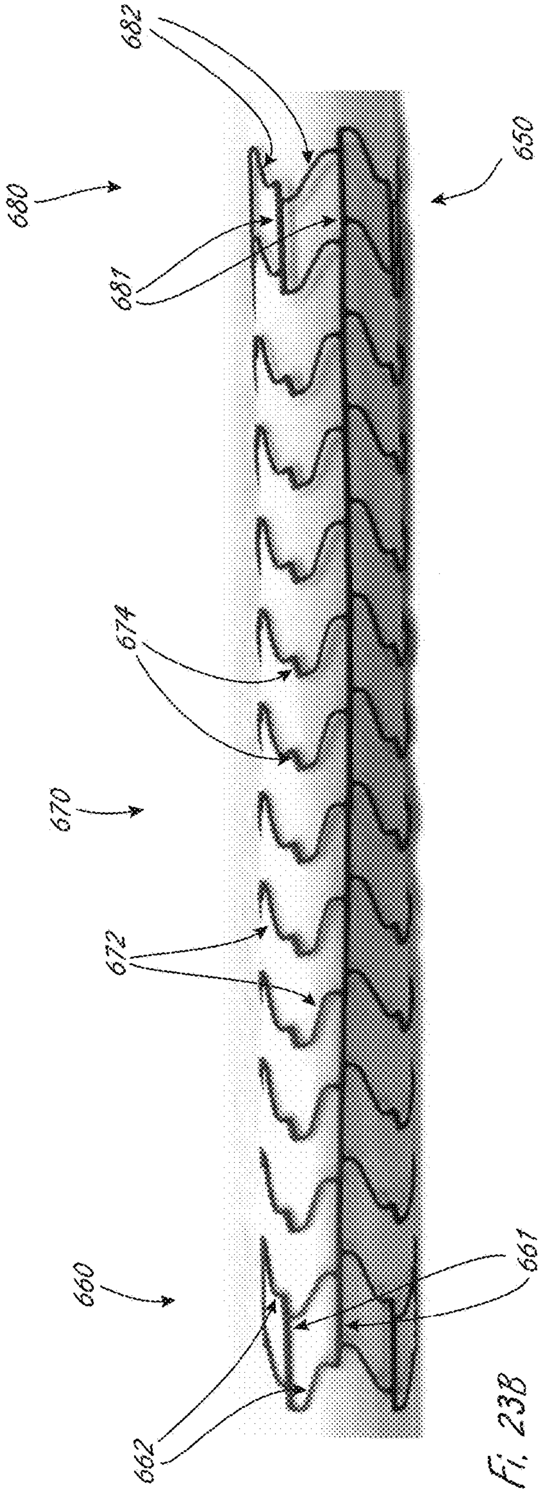
Fi. 23B

CATHETER BLOOD PUMPS AND COLLAPSIBLE PUMP HOUSINGS

CROSS REFERENCE TO RELATED APPLICATIONS

This applications claims benefit of priority to U.S. Prov. App. No. 62/884,089, filed Aug. 7, 2019, the entire disclosure of which is incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

One aspect of the disclosure is a catheter blood pump. The blood pump may include an expandable pump portion extending distally relative to a catheter. The pump portion may include an impeller housing that includes an expandable blood conduit defining a blood lumen. The expandable blood conduit may include a scaffold that provides radial support to the blood conduit.

In any embodiment of this aspect, the scaffold may include one or more of a proximal scaffold, a distal scaffold, or a central scaffold disposed between a proximal scaffold and a distal scaffold.

In any embodiment of this aspect, a central scaffold may be less stiff in response to a radially inward force than one or both of a proximal scaffold and a distal scaffold.

In any embodiment of this aspect, a proximal scaffold may be a proximal impeller scaffold.

In any embodiment of this aspect, a distal scaffold may be a distal impeller scaffold.

In any embodiment of this aspect, the one or more scaffold sections may be coupled to a membrane, the membrane at least partially defining the blood lumen.

In any embodiment of this aspect, a proximal impeller may disposed at least partially within the proximal scaffold and a distal impeller may be disposed at least partially within a distal scaffold.

In any embodiment of this aspect, a central scaffold may be connected with at least one of the proximal impeller scaffold and the distal impeller scaffold, optionally unitarily connected to one or both.

In any embodiment of this aspect, a central scaffold may be attached to a proximal impeller scaffold and to a distal impeller scaffold, optionally with welds.

In any embodiment of this aspect, a central scaffold may have a configuration that is different than the proximal impeller scaffold and the distal impeller scaffold.

In any embodiment of this aspect, a proximal impeller scaffold and a distal impeller scaffold may have the same or substantially the same configuration. A dimension of a first feature of a proximal impeller scaffold may be different than a corresponding feature of the distal impeller scaffold.

In any embodiment of this aspect, a proximal impeller scaffold and a distal impeller scaffold may have different configurations.

In any embodiment of this aspect, a distal impeller scaffold may have a length that is greater than a length of a proximal impeller scaffold.

In any embodiment of this aspect, a distal impeller may have a length that is less than a length of a proximal impeller.

In any embodiment of this aspect, a width dimension of a central scaffold axially extending element may be less than a width dimension of a proximal impeller scaffold axially extending element. A central scaffold linear element may be axially linear. A central scaffold linear element may be helically linear. Proximal impeller scaffold linear elements may be axially linear.

In any embodiment of this aspect, at least one of the proximal impeller scaffold and the distal impeller scaffold may comprise a plurality of axially extending elements (optionally linear) spaced apart around the blood conduit. First and second adjacent axially extending elements may each be connected by a circumferential connector having at least one bend formed therein, the circumferential connectors defining a plurality of circumferential connectors around the blood conduit. Circumferentially adjacent circumferential connectors of the plurality of circumferential connectors may be displaced axially relative to one another, and wherein each one of the linear axially extending elements connects adjacent circumferential connectors that are axially displaced. A first group of a plurality of circumferential connectors may have a first axial position, and wherein a second group of the plurality of circumferential connectors may have a second axial position, wherein the first and second axial positions alternate circumferentially around the blood conduit.

In any embodiment of this aspect, at least one of a proximal impeller scaffold and a distal impeller scaffold may comprise a second plurality of circumferential connectors that are mirrored with a first plurality of circumferential connectors.

In any embodiment of this aspect, a length of a proximal impeller scaffold may be less than a length of a distal impeller scaffold. A length of a distal impeller may be less than a length of a proximal impeller. A proximal impeller may extend proximally out of the blood conduit.

In any embodiment of this aspect, a central scaffold may include a plurality of helical elements having a helical configuration between a proximal scaffold and a distal scaffold. Adjacent helical elements of the plurality of helical elements may be connected by a plurality of connectors. A plurality of these connectors may comprise an inflection point where the connectors transitions from convex to concave. The helical elements may be an extension of a linear axial element in at least one of the proximal scaffold or the distal scaffold. Linear axial elements in a proximal and a distal scaffold that extend from a first helical element may not be circumferentially aligned.

In any embodiment of this aspect, a distal scaffold may be circumferentially offset relative to a proximal scaffold, optionally between one and ninety degrees relative to a proximal scaffold.

In any embodiment of this aspect, first circumferential members in a distal scaffold may be axially closer together than corresponding second circumferential members in a proximal scaffold.

BRIEF DESCRIPTION OF THE DRAWINGS

FIG. 14A illustrates an exemplary expanded scaffold that may be part of any of the expandable pump portions herein.

FIG. 14B illustrates the scaffold and struts from FIG. 14A in a flattened and non-expanded configuration.

FIG. 15A illustrates an exemplary expanded scaffold that may be part of any of the expandable pump portions herein.

FIG. 15B illustrates the scaffold and struts from FIG. 15A in a flattened and non-expanded configuration.

FIG. 23A illustrates an exemplary scaffold in a flattened and non-expanded configuration.

FIG. 23B illustrates the scaffold from FIG. 23A in an expanded configuration.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
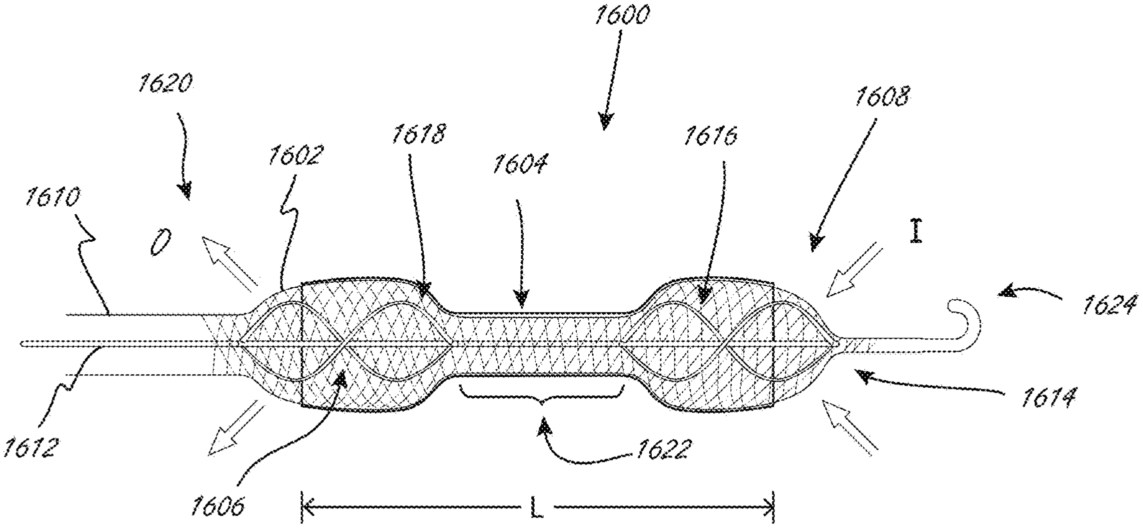
FIG. 1 is a side view of an exemplary expandable pump portion that includes an expandable impeller housing that includes a scaffold and blood conduit, and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to herein as expandable scaffolds or scaffold sections. Expandable scaffold 1602 is disposed radially outside of the impellers along the axial length of the impellers. Expandable scaffold 1602 can be constructed in a manner and made from materials similar to many types of expandable structures that are known in the medical arts to be able to be collapsed and expanded, examples of which are provided herein. Examples of suitable materials include, but are not limited to, polyurethane, polyurethane elastomers, metallic alloys, etc.

Pump portion 1600 also includes blood conduit 1604, which is coupled to and supported by expandable member 1602, has a length L, and extends axially between the impellers. Conduit 1604 creates and provides a fluid lumen between the two impellers. When in use, fluid moves through the lumen defined by conduit 1604. The conduits herein may be non-permeable, or they may be semipermeable, or even porous as long as they still define a lumen. The conduits herein are also flexible, unless otherwise indicated. The conduits herein extend completely around (i.e., 360 degrees) at least a portion of the pump portion. In pump portion 1600, the conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "0." Conduit 1604 improves impeller pumping dynamics, compared to pump portions without a conduit. As described herein, expandable members or scaffolds may also be considered to be a part of the blood conduit generally, which together define a blood lumen. In these instances the scaffold and material supported by the scaffold may be referred to herein as an expandable impeller housing or housing.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24F (4.0-8.0 mm) where the impellers are axially within the expandable member, and to an outermost dimension of 10-20F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or 8,052,749, the disclosures of which are incorporated by reference herein.

Figure 2:
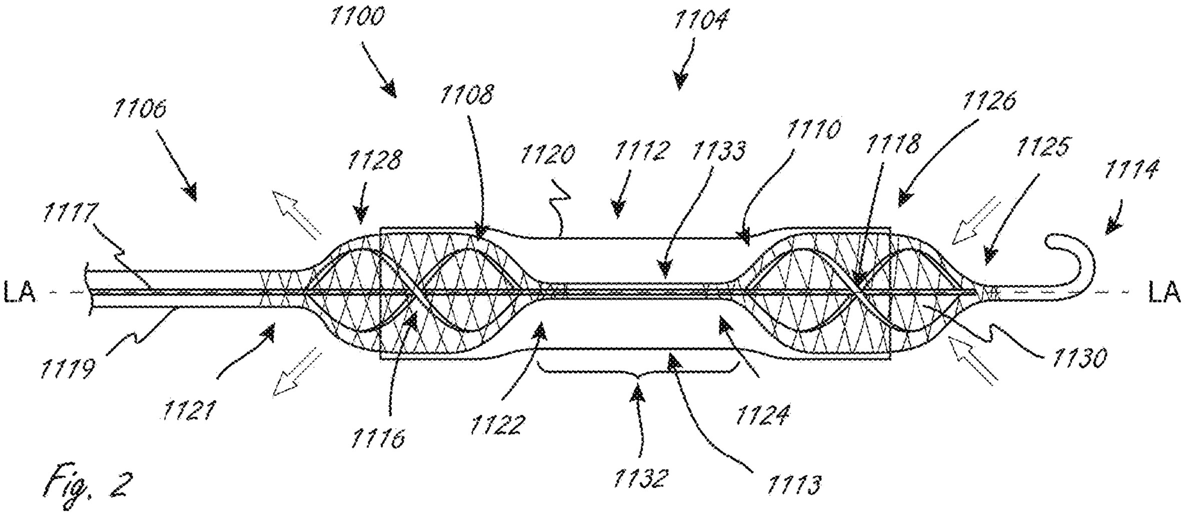
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841,976 or 8,052,749, the disclosures of which are incorporated by reference herein for all purposes.

Figure 3A:
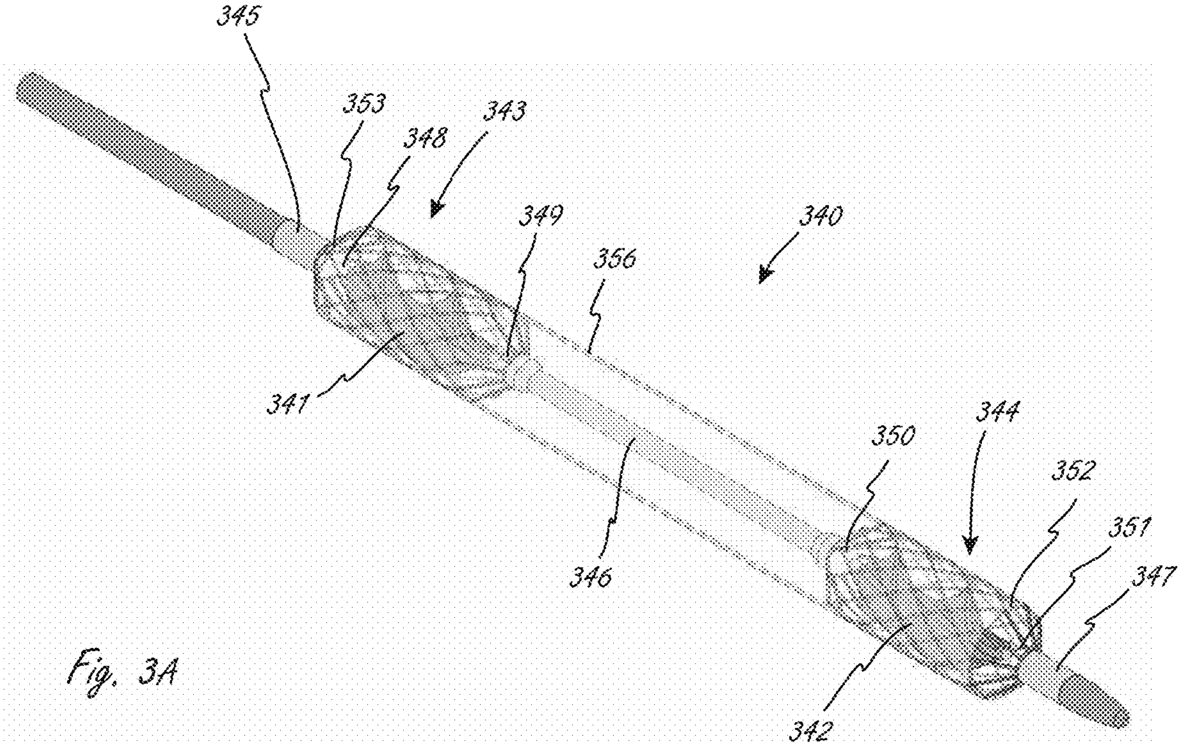
FIGS. 3A, 3B, 3C and 3D illustrate an exemplary expandable pump portion that includes a blood conduit, a plurality of impellers, and a plurality of expandable scaffold sections or support members.
Figure 3B:
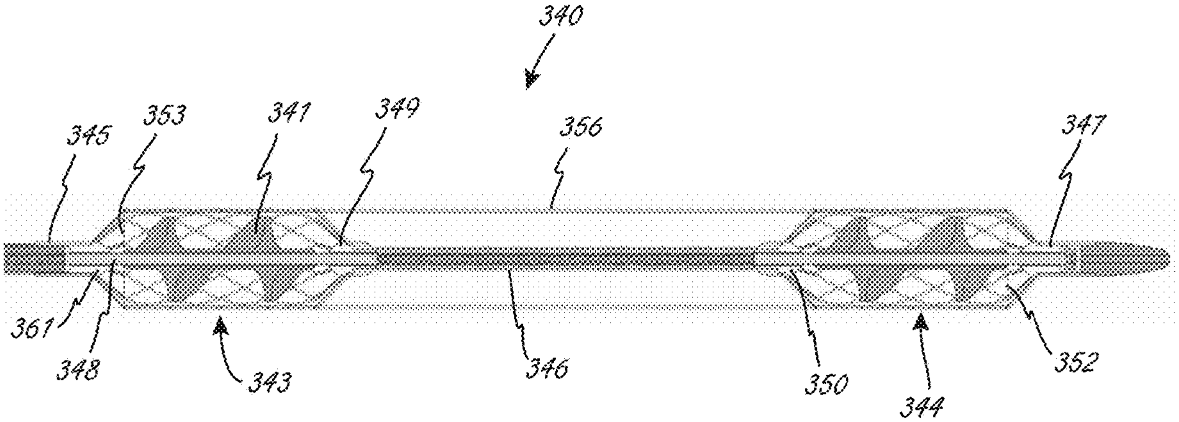
Figure 3C:
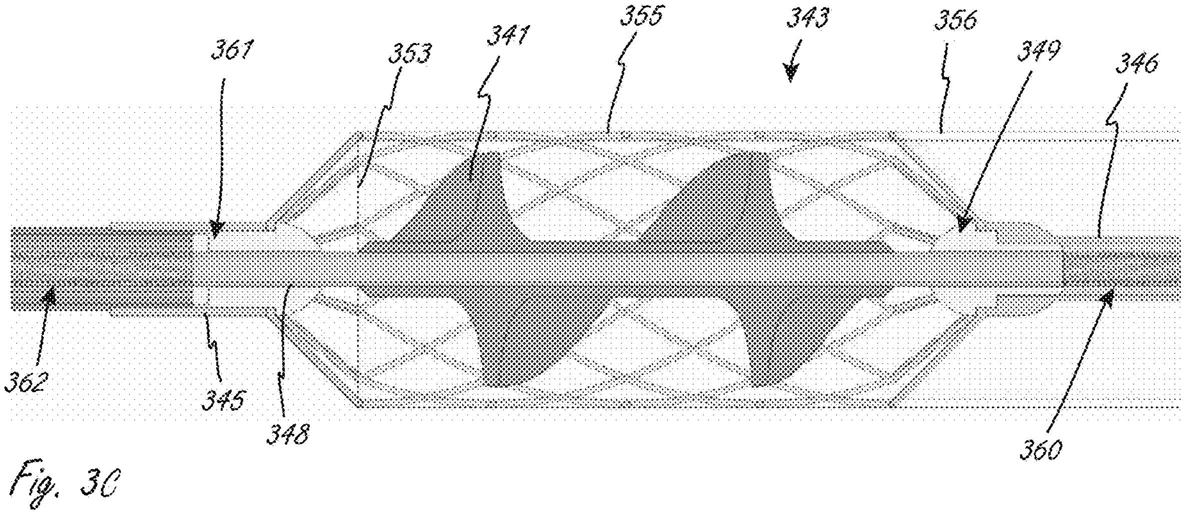
Figure 3D:
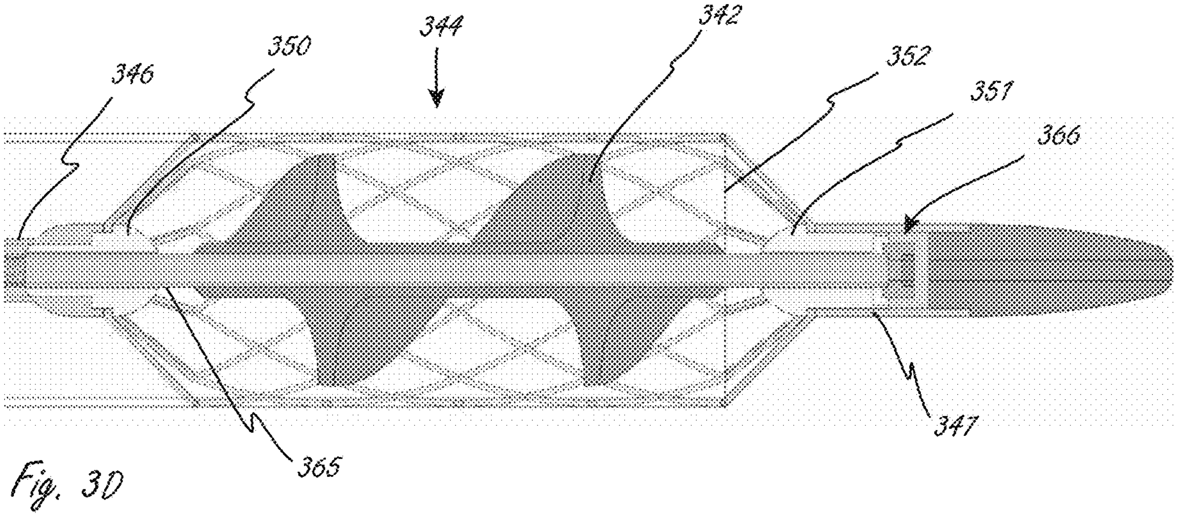

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
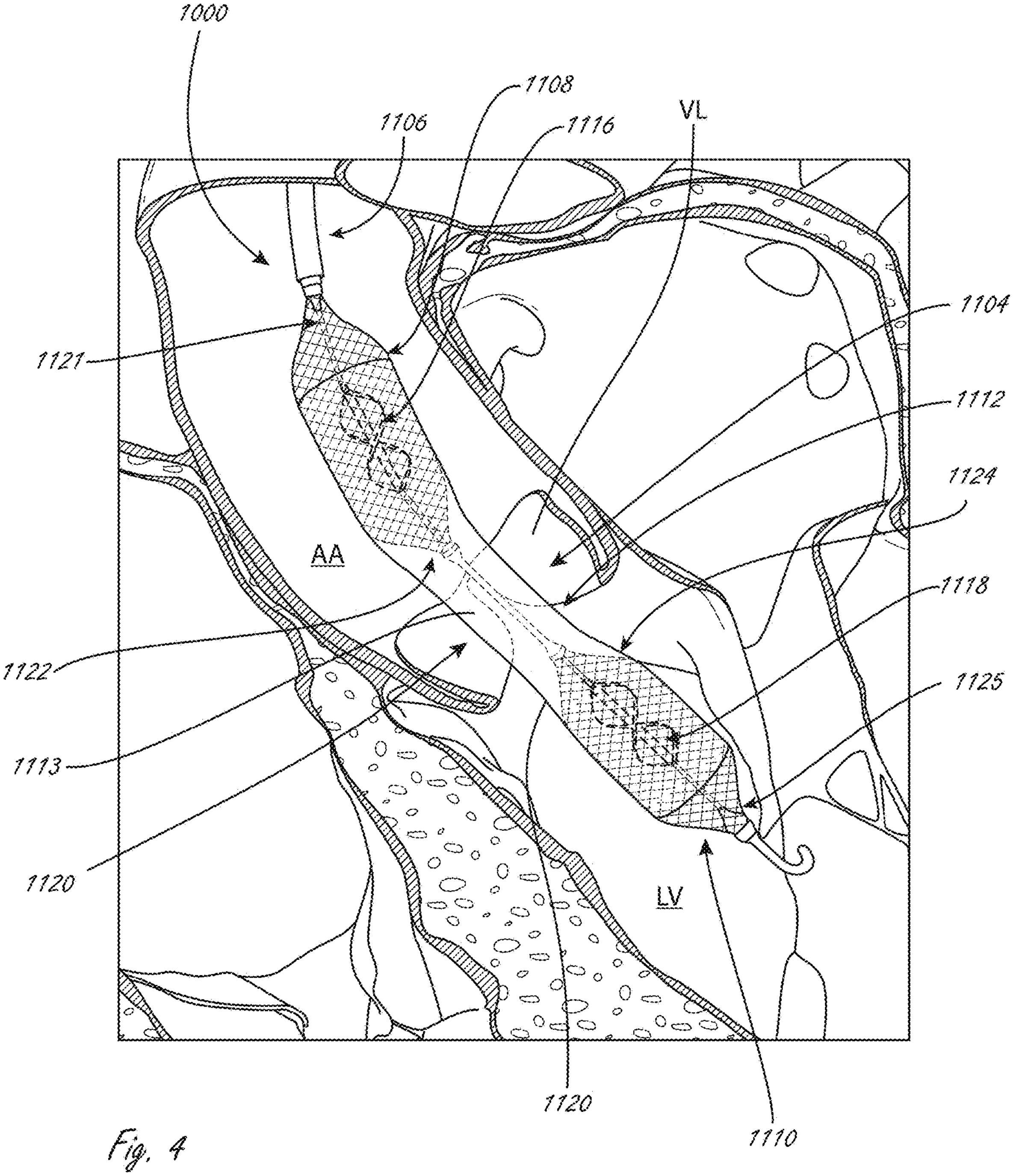
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIG. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
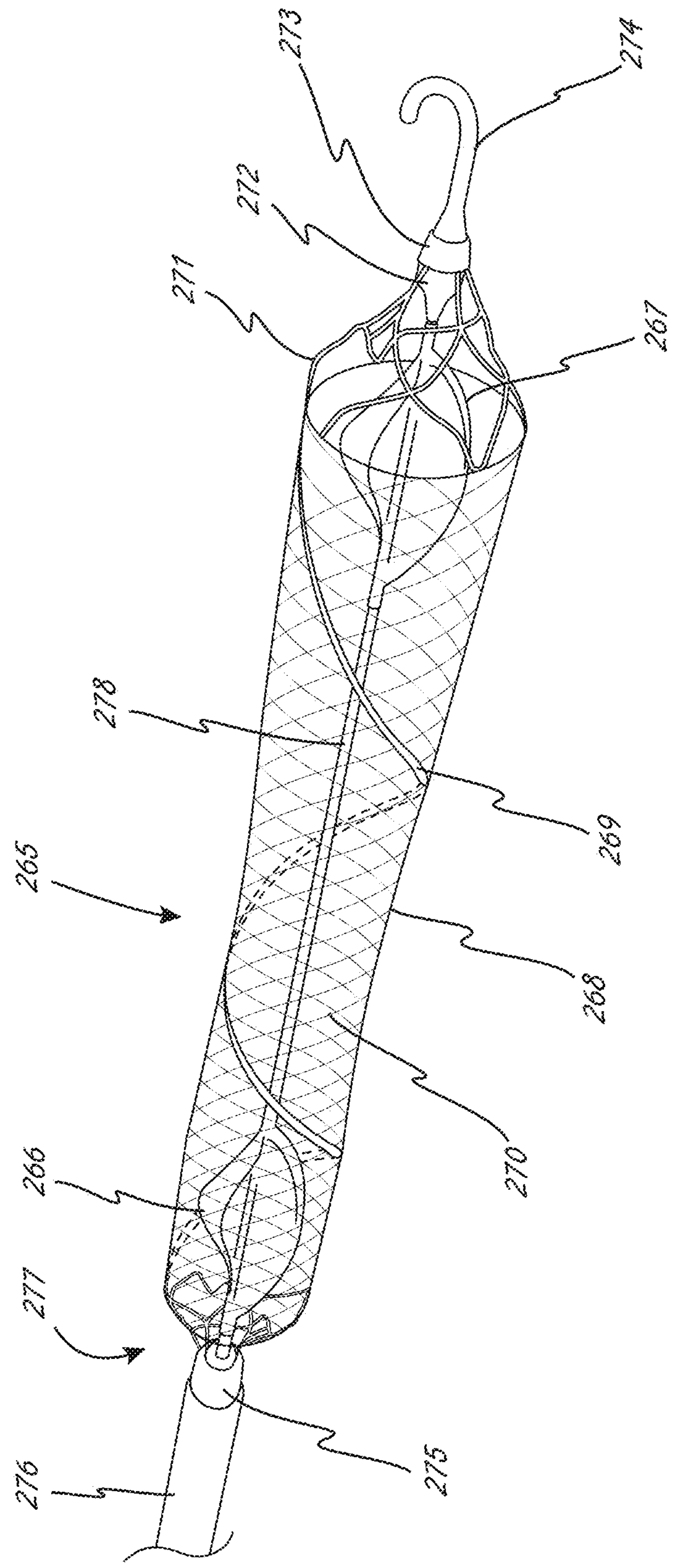
FIG. 5 illustrates an exemplary pump portion including an expandable impeller housing, a blood conduit, and a plurality of impellers.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
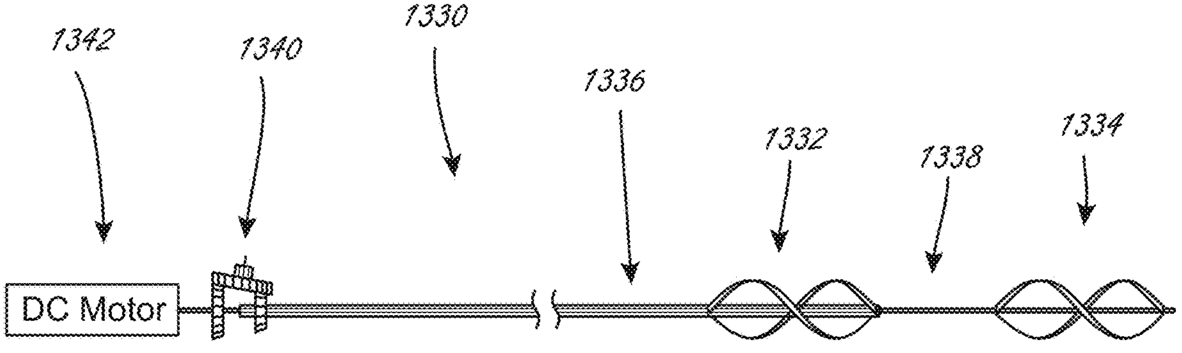
FIG. 6A illustrates at least a portion of an exemplary catheter blood pump that includes a pump portion, wherein at least two different impellers can be rotated at different speeds.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 6B:
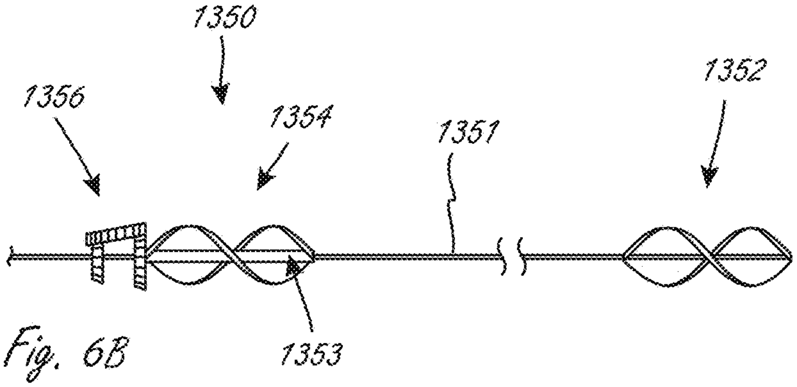
FIG. 6B illustrates at least a portion of an exemplary catheter blood pump that includes a pump portion, where at least two different impellers can be rotated at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

Figure 7:
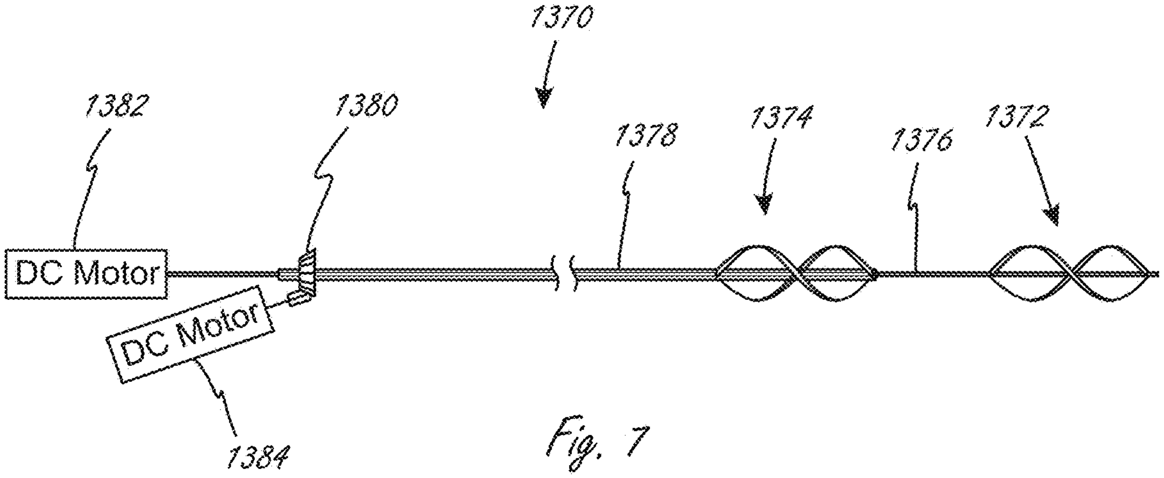
FIG. 7 illustrates a portion of an exemplary catheter blood pump that includes a pump portion.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

Figure 6C:
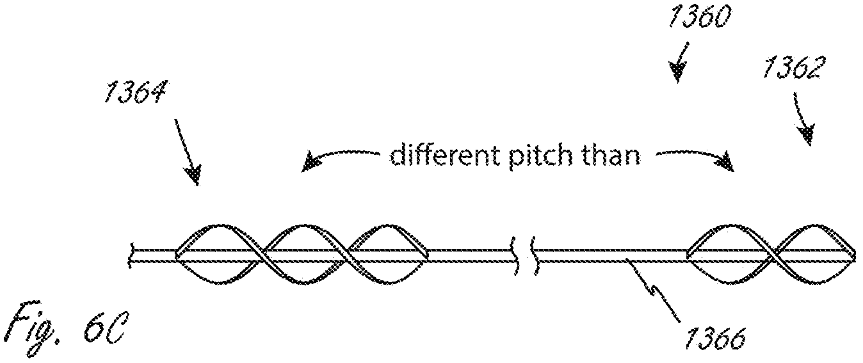
FIG. 6C illustrates at least a portion of an exemplary catheter blood pump that includes a pump portion with at least two impellers having different pitches.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figure 8:
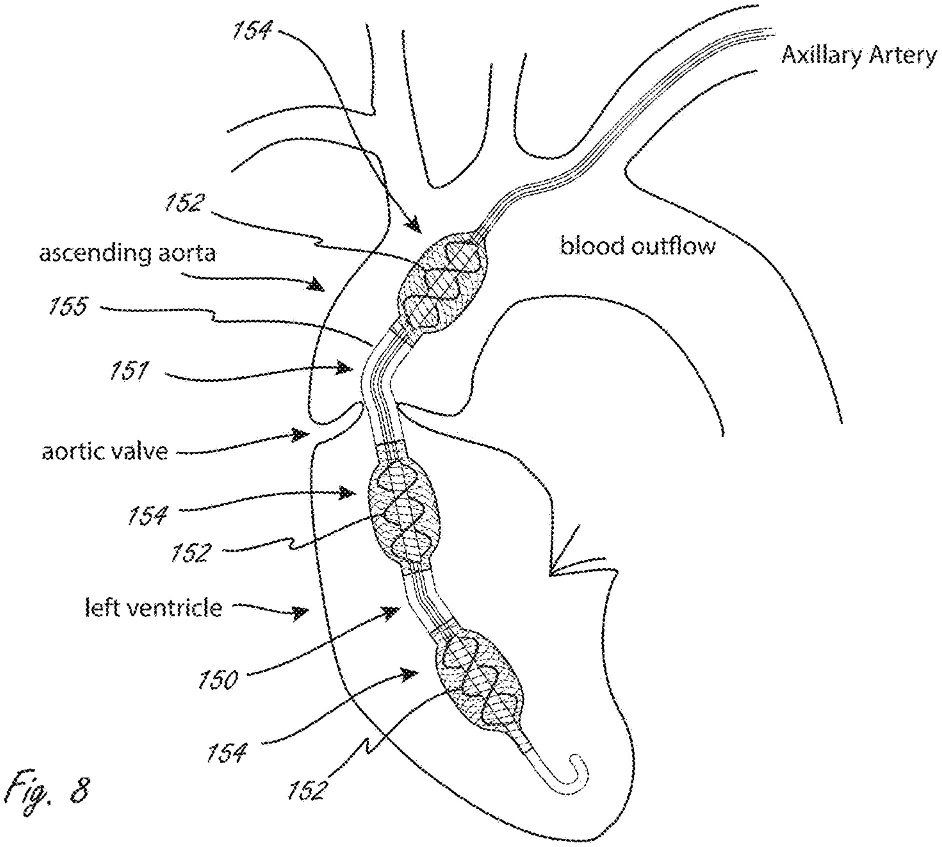
FIG. 8 illustrates an exemplary expandable pump portion including a plurality of expandable impellers, including one or more bends formed therein between adjacent impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. I t can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

Figure 9:
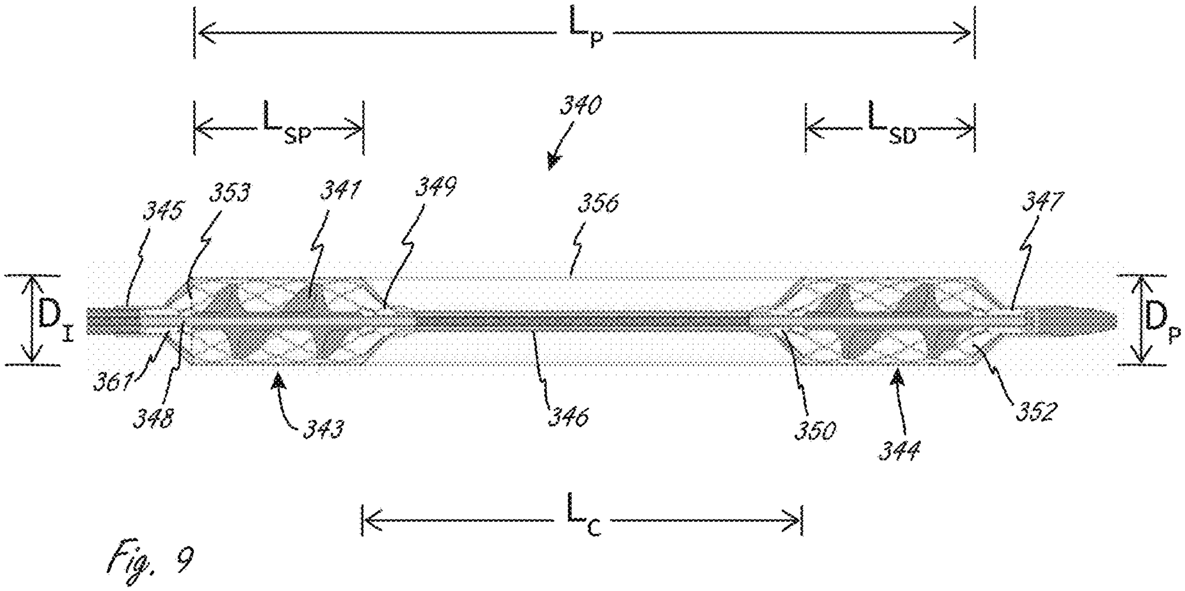
FIG. 9 illustrates an exemplary expandable pump portion comprising a plurality of impellers and a blood conduit.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
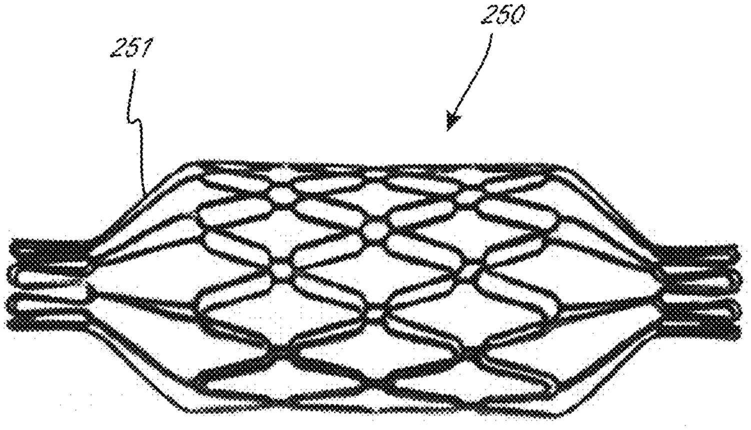
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
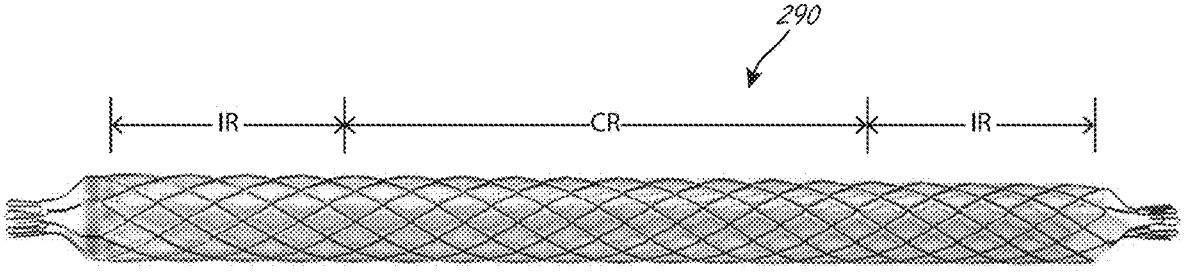
FIG. 11 illustrate an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
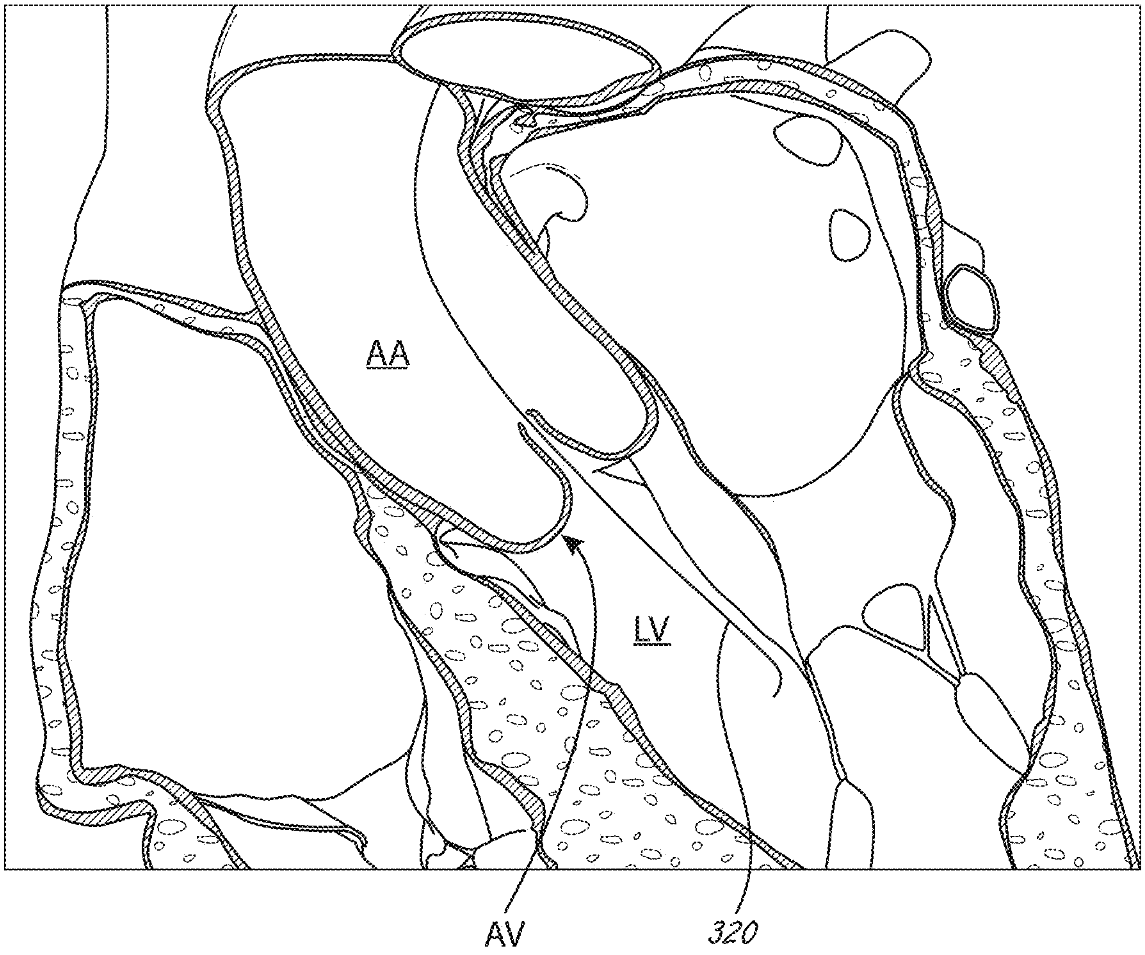
FIGS. 12A-12F illustrate an exemplary sequence of steps that may be performed to deploy an exemplary pump portion of a catheter blood pump.
Figure 12B:
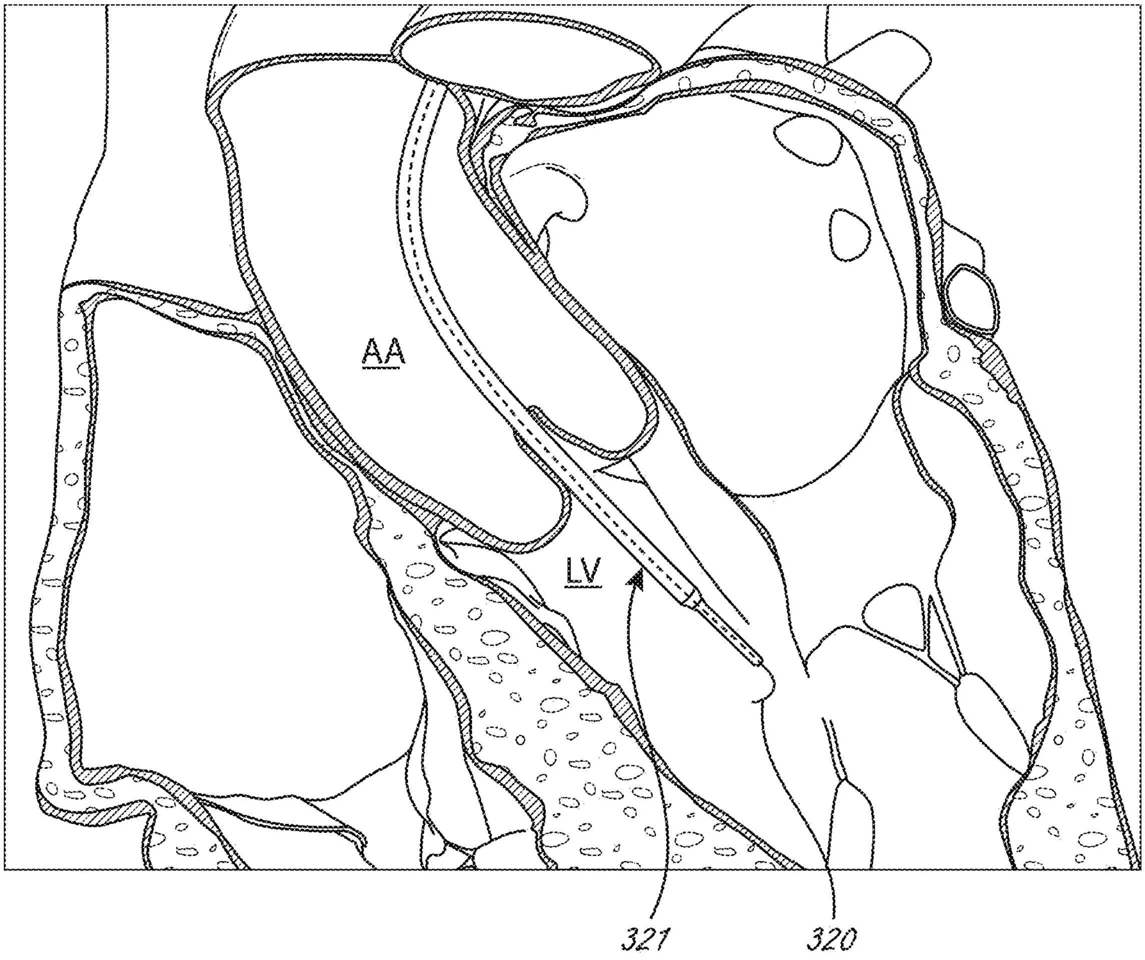

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
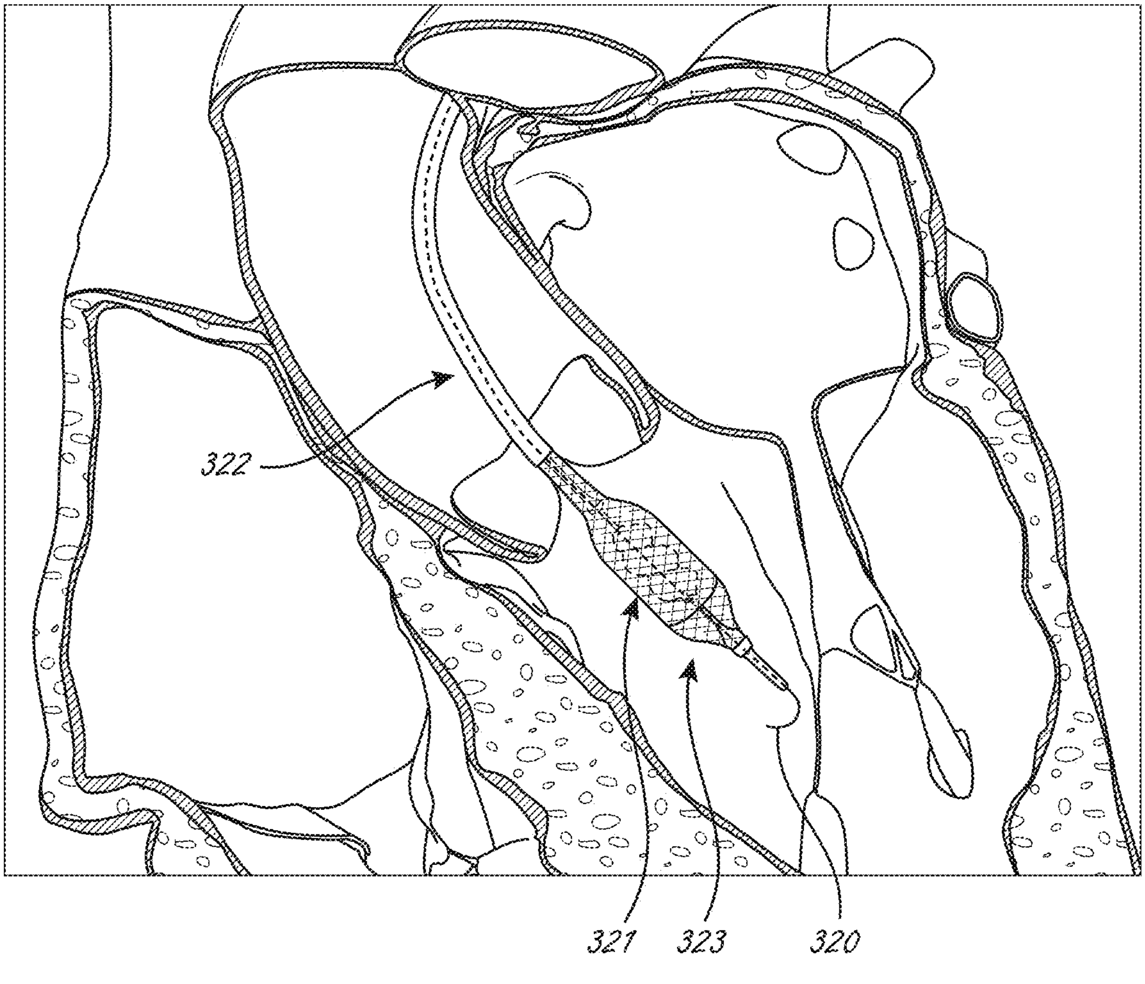
Figure 12D:
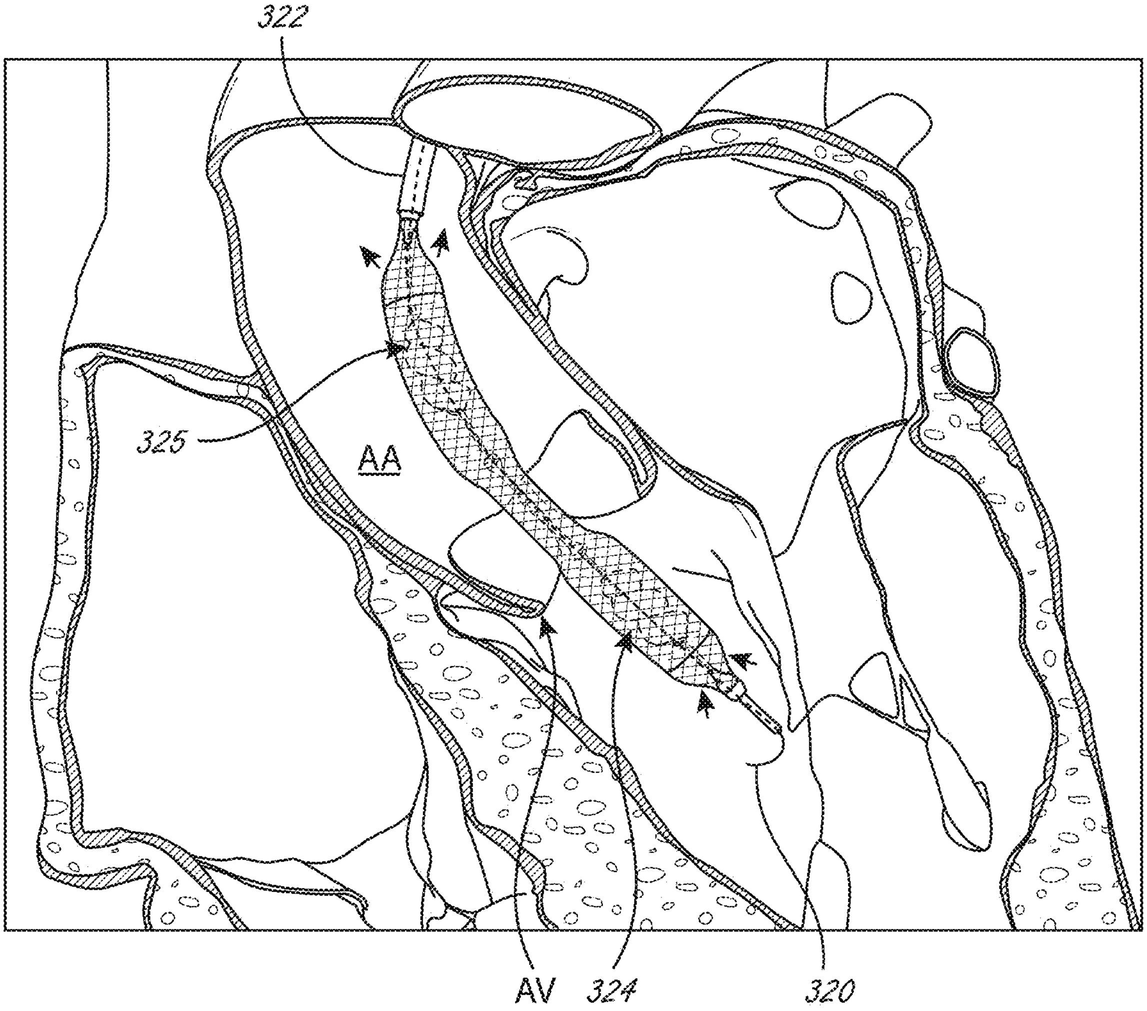

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
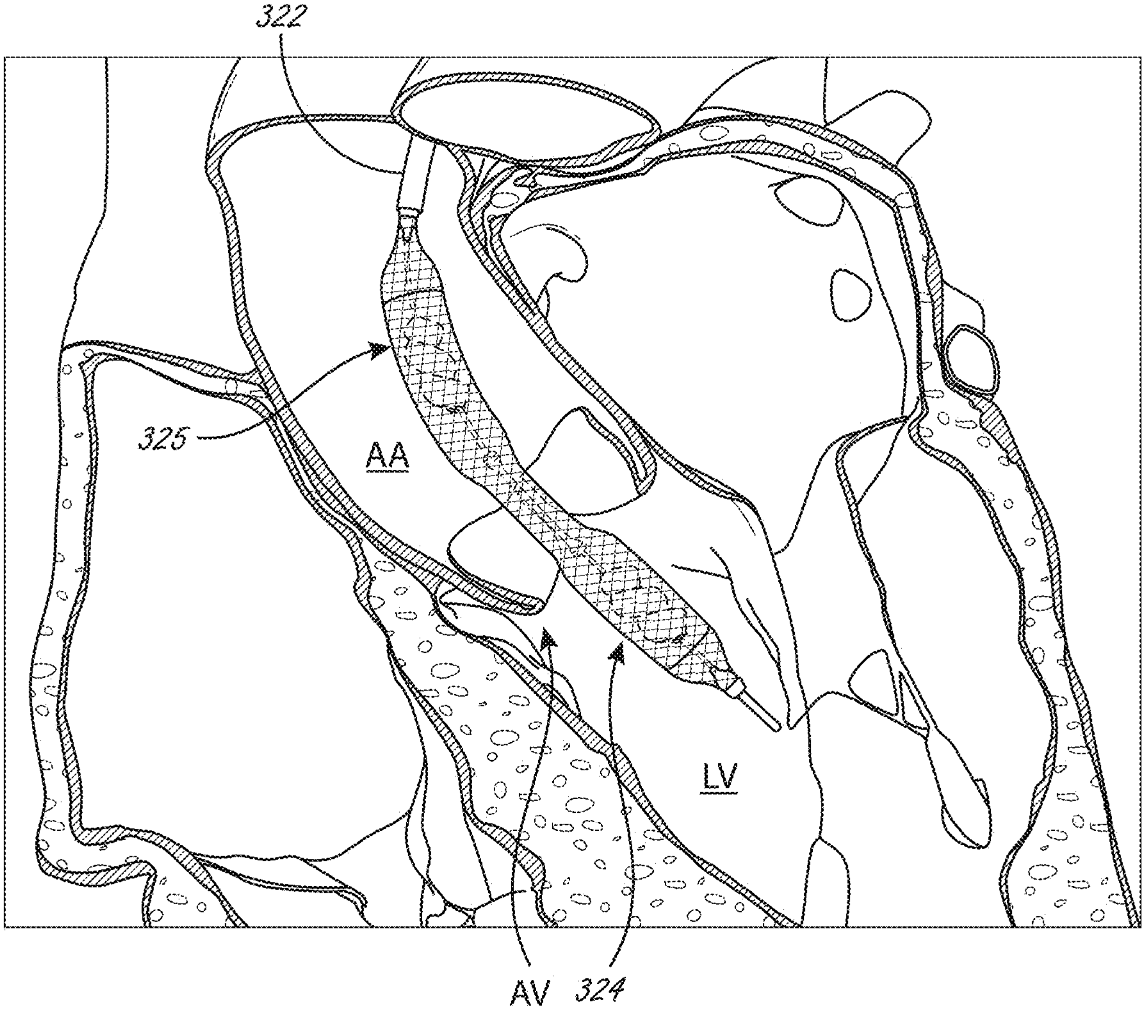
Figure 12F:
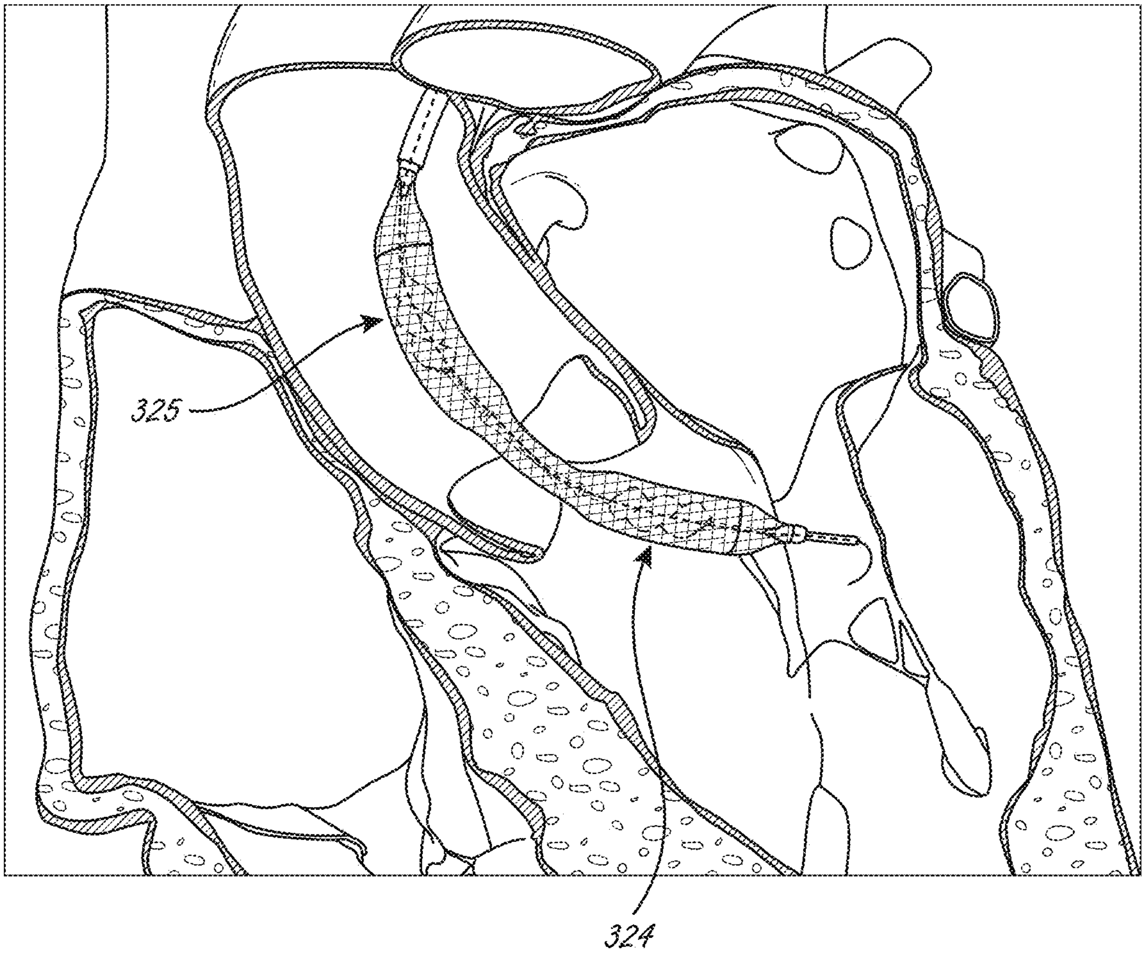

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

As set forth above, this disclosure includes catheter blood pumps that include an expandable pump portion extending distally relative to a catheter. The pump portions include an impeller housing that includes an expandable blood conduit that defines a blood lumen. The blood conduit may include one or more scaffold sections that together may also be referred to herein as a single scaffold. In some exemplary embodiments the expandable blood conduit may include one or more of a proximal impeller scaffold, a distal impeller scaffold, and a central scaffold disposed between the proximal impeller scaffold and the distal impeller scaffold, where any combination thereof may also be referred to herein as a scaffold. Any individual proximal impeller scaffold or distal impeller scaffold may also be referred to herein as an expandable member, such as is shown in FIGS. 3A-3D. In some embodiments the expandable blood conduit may include a proximal impeller scaffold and additional scaffold extending distally therefrom, such as if the pump portion includes a proximal impeller but does not include a distal impeller. In any of the embodiments herein, a reference to a distal impeller is only by way of example, and pump portions herein need not include a distal impeller. Central scaffolds herein are generally less stiff in response to a radially inward force than a proximal scaffold, and optionally also less stiff than a distal scaffold, such as a distal impeller scaffold. Exemplary advantages of central scaffold sections that are less stiffness are set forth elsewhere herein. The blood conduit may also include a membrane coupled to the one or more scaffolds, the membrane at least partially defining the blood lumen. Membranes in this context may incorporate by reference herein the disclosure of conduits, including any feature or method of manufacturing described above. The catheter blood pumps may include an impeller disposed in a proximal region of the impeller housing, which may be a proximal impeller. The catheter blood pumps may also include a distal impeller in a distal region of the impeller housing. Exemplary impellers, including exemplary proximal and distal impellers, are set forth herein by way of example. An impeller that is at least partially within a portion of a scaffold may be described with respect to the relative position of the scaffold, such the a proximal impeller within at least a portion of a proximal scaffold, or a distal impeller within at least a portion of a distal scaffold.

When a proximal impeller is described as being within a proximal scaffold, it is understood that the proximal scaffold need not axially extend over an entire length of the impeller, as long as there is some amount of axial overlap. For example, some proximal impellers herein extend proximally from a blood conduit, and a proximal region of the proximal impeller is not surrounded by a blood conduit scaffold, while a distal region of the impeller is surrounded by scaffold. Similarly, when a distal impeller herein (if the pump includes a distal impeller) is described as being within a distal scaffold, it is understood that the distal scaffold need not axially extend over an entire length of the impeller, as long as there is some degree of axial overlap therebetween.

FIGS. 13A-17 illustrate exemplary designs for expandable scaffolds herein, which may at least partially surround an impeller that is at least partially disposed within a conduit that creates a fluid lumen. The scaffold patterns in FIGS. 13A-17 may be scaffold patterns that only extend over a particular impeller (e.g., a proximal basket or distal basket), or they may be scaffold patterns that extend over an entire blood conduit scaffold.

FIGS. 13A-17 illustrate expandable support members or scaffolds that each have an expanded configuration, wherein in the expanded configuration the support member has a plurality of continuous axially extending elements (e.g., 408, 410, 420, 430, 440) that are continuous and axially extending over at least 50% of a length of the expandable support member (e.g., $L_s$), and wherein the expandable support member includes a plurality of sets of connectors (e.g., 412/414, 409, 422/424, 432/434, 442/444) each set of connectors extending between first and second circumferentially adjacent continuous axially extending elements. In some embodiment the axially extending elements are linear or substantially linear.

Figure 13A:
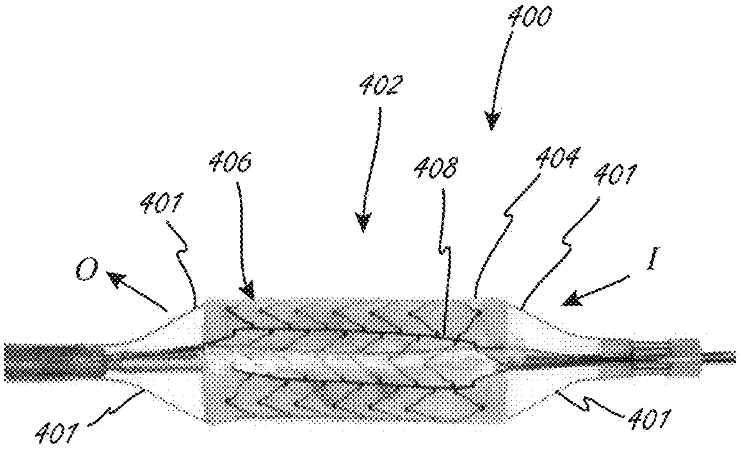
FIGS. 13A and 13B illustrate exemplary portions of an expandable pump portion.
Figure 13B:
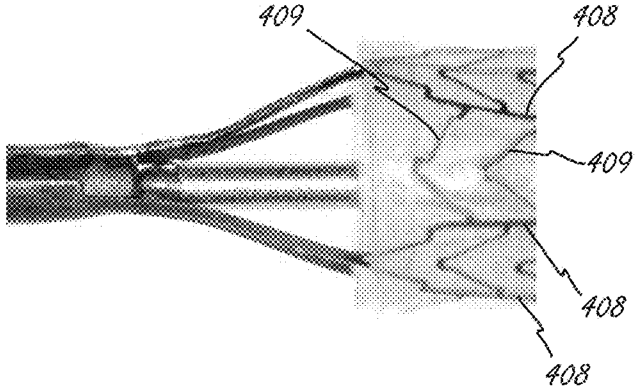
Figure 13C:
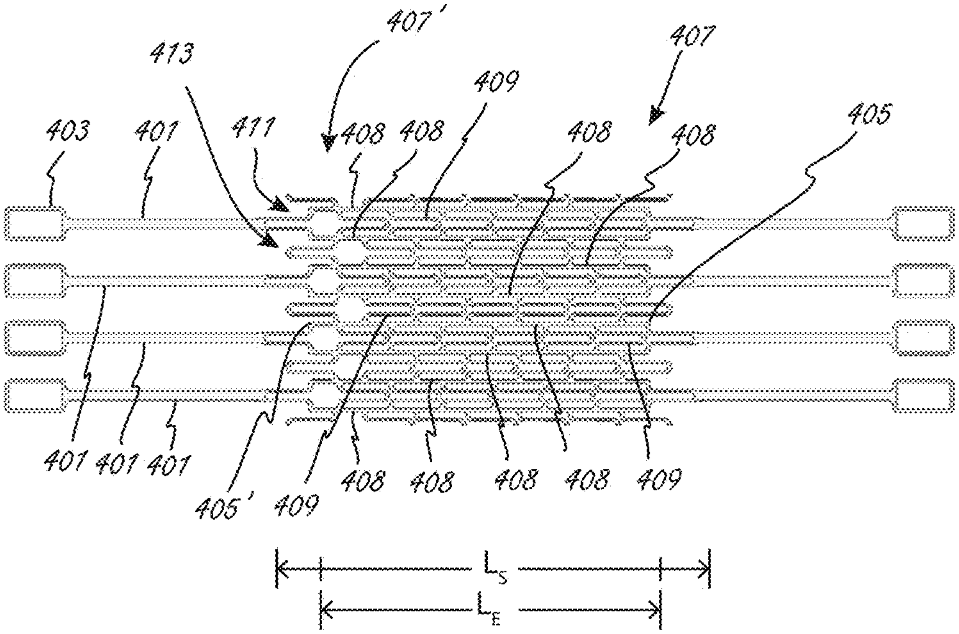
FIG. 13C illustrates a scaffold from FIGS. 13A and 13B shown in a flattened and non-expanded configuration, as well as optional distal and proximal struts extending axially therefrom.

FIGS. 13A-13C illustrate an exemplary pump portion 400 or a portion thereof that comprises an expandable impeller housing 402, wherein the expandable impeller housing having a blood conduit 404, the conduit defining a blood lumen between an housing inflow "I" and a housing outflow "O". The expandable impeller housing also includes an expandable scaffold or support member 406 at least partially surrounding an impeller (not shown in FIGS. 13A-13C) that is at least partially disposed within the conduit. FIGS. 14A-17 illustrate an expandable scaffold of the pump portion. It is understood that any expandable scaffold in any of FIGS. 13A-17 may be used in place of any expandable scaffold herein. Impeller housing 402 may illustrate the entire impeller housing, or it may only represent only a portion thereof, including only a single scaffold section, such as with any of the multi-impeller designs herein. It is thus understood that the structure shown in FIGS. 13A-C may only be a portion of the expandable housing of a pump portion. For example, a pump portion may include two of the expandable scaffold sections shown in FIGS. 13A-C, axially spaced apart, and coupled by a flexible membrane, for example.

FIGS. 13A-C illustrate an expandable impeller housing that includes a plurality of axially extending elements 408 circumferentially spaced apart around the housing 402 from adjacent axially extending elements, as shown. FIGS. 13A and 13B show an expanded configuration of the housing, while FIG. 13C illustrates a model of a flat, unexpanded configuration with unitary struts 401 extending axially therefrom, as shown. The plurality of axially extending elements may be referred to as "elements" in the context of scaffolds for simplicity, but it is understood that they are not to be considered any other type of "element" herein unless specifically indicated as such. The elements in this embodiment may be axial and linear in the housing expanded configuration. Expandable scaffold 406 also includes circumferential connectors 409 that circumferentially connect adjacent axial elements and extend from one axial element to an adjacent axial element. In this exemplary embodiment all of the connectors have the same general configuration, which includes first and second segments meeting at a rounded peak that is oriented axially (proximally or distally depending on the reference frame), otherwise stated as pointing axially. Length Ls of the scaffold and length Le of the elements is illustrated in FIG. 13C. Optional struts 401 are shown (which may be unitary with the scaffold). The axial elements 408 in this embodiment extend from a first axial element end 405 to second axial element end 405', which extend almost the entire length of the scaffold Ls. As shown, ends 405' of the elements (only one labeled) extend to a distal end region 407' of the scaffold 406. End 405 extends to proximal end region 407. The pump portion also includes a transition region 411, which includes circumferential extensions of adjacent axial elements, after which they meet to form a strut 401, as shown.

FIGS. 14A (expanded) and 14B (unexpanded) illustrate an exemplary expandable scaffold 406', which includes a plurality of axially extending elements 410. A first set of connectors 412 have "S" configurations, and a second circumferentially adjacent set of connectors 414 have inverse (reverse) "S" shapes. In the expanded configuration in FIG. 14A the axial elements 410 may be linear, or they may have a slight curvilinear configuration as shown. Scaffold 406' includes transition region 411', which may have similar features to the transition region 411 herein. The relevant description from any other embodiment may be incorporated with the scaffold in FIGS. 14A-B (e.g., lengths of scaffold or support member and axial elements, transition region, etc.). Some of the optional struts 413 are shown, as are ends 405/405' of the axial elements. Scaffold 406' may be proximal or distal scaffold, or it may extend along the length of the impeller housing.

FIGS. 15A and 15B illustrate an exemplary expandable scaffold 406" that is similar to those in FIGS. 13, 14, 16, and 17. Axially extending elements 420 are shown, adjacent ones of which are connected by circumferential connectors 422 and 424, ends of which are axially offset. A first set of connectors 422 has a general S configuration, while a second set of connectors 424 are reverse S-shaped. In this embodiments the axially extending elements 420 are curvilinear, as shown. The pattern of S and inverse-S alternates around the expandable member, as it does in the scaffolds in FIGS. 14A and 14B. Scaffold 406" also includes a transition region 421, examples of which are described elsewhere herein. Scaffold 406" may be proximal or distal scaffold, or it may extend along the length of the impeller housing.

Figure 16:
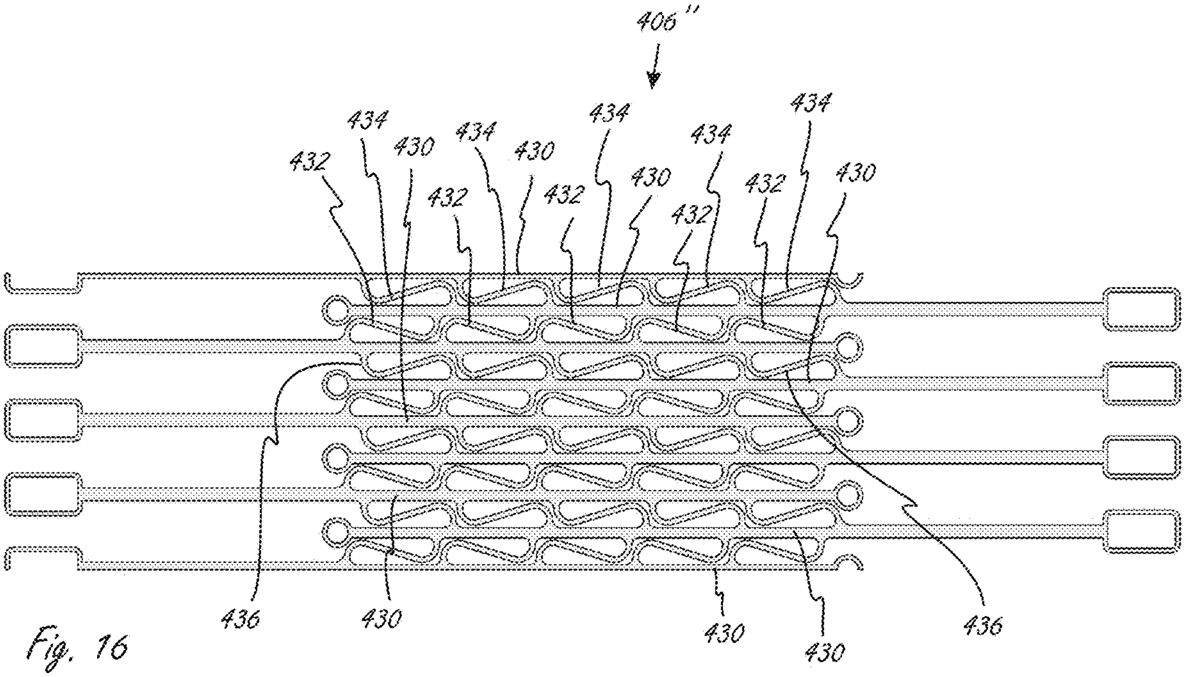
FIG. 16 illustrates an exemplary scaffold and optionally coupled struts in a flattened and non-expanded configuration.

FIG. 16 illustrates a collapsed (unexpanded) configuration of an exemplary scaffold 406'", which may have any other suitable features of any other support member or scaffold herein. Axially extending elements 430 are shown, connected by first set of S-shaped connectors 434 and a second set of inverse-S shaped connectors 432. The pattern of S and inverse-S shapes alternates circumferentially around the scaffold 406'" as shown. Scaffold 406'" may be proximal or distal scaffold, or it may extend along the length of the impeller housing.

Figure 17:
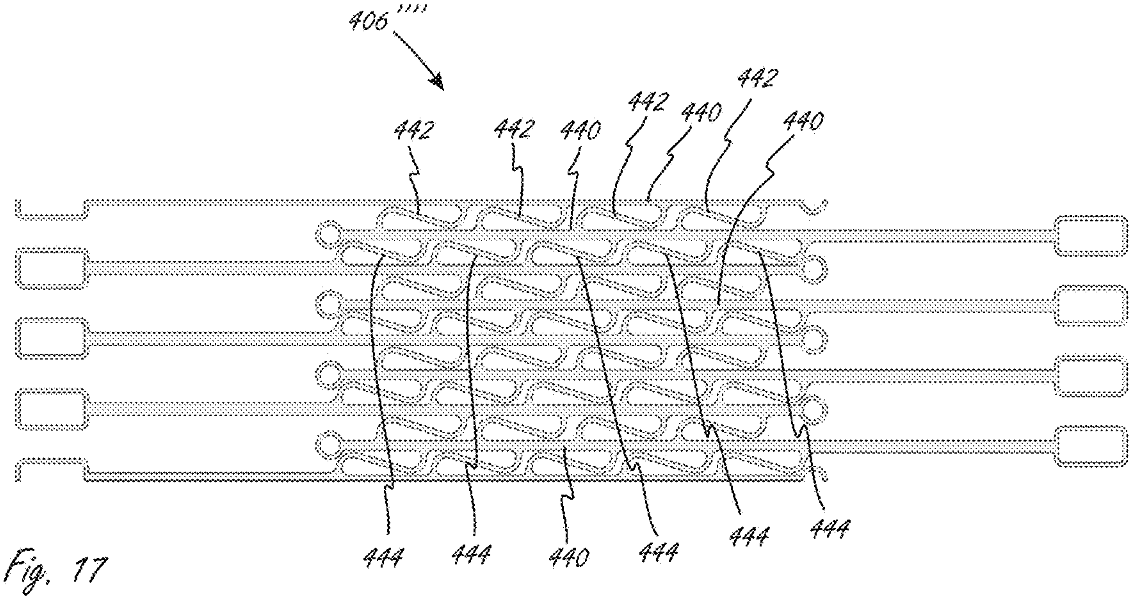
FIG. 17 illustrates an exemplary scaffold and optionally coupled struts in a flattened and non-expanded configuration.

FIG. 17 illustrates a collapsed (unexpanded) configuration of an exemplary scaffold 406"", which may have any other suitable features of any other support member or scaffold herein. Axially extending elements 440 are shown, connected by inverse-S shaped connectors. All sets of the connectors in this embodiment (e.g., set 442 and set 444) have the same configuration, and in this embodiment are all inverse-S shaped. Exemplary struts are shown axially disposed relative to the scaffold 406"", and the scaffold 406"" may include transition sections which are described elsewhere herein. Scaffold 406"" may be a proximal scaffold or a distal scaffold, or it may extend along the length of the impeller housing.

The scaffolds and blood conduit embodiments in FIGS. 13A-17 are illustrative, and may be modified to include aspects of other embodiments herein. The following description may provide modifications to the scaffolds in FIGS. 13A-17, any of which may be incorporated into any of the scaffolds in FIGS. 13A-17.

In any of the scaffolds shown in FIGS. 13A-17, at least a first end of each of the plurality of axially extending elements may extend to one or more of a proximal end region (e.g., 417', 407') and a distal end region (e.g., 417,) of the expandable scaffold.

In any of the scaffolds shown in FIGS. 13A-17, at least one of, and optionally all of, the plurality of axially extending elements may be linear. In any of the scaffolds shown in FIGS. 13A-17, at least one of, and optionally all of, the plurality of axially extending elements may be curvilinear.

In any of the scaffolds shown in FIGS. 13A-17, each one of the plurality of axially extending elements may have proximal and distal ends, wherein the proximal and distal ends are substantially circumferentially aligned.

In any of the scaffolds shown in FIGS. 13A-17, each of the plurality of axially extending elements may have a circumferential span (illustrated as "CS" in FIG. 15A) that is not larger than 10 degrees circumferentially around the expandable scaffold, optionally not larger than 5 degrees of the expandable scaffold.

In any of the scaffolds shown in FIGS. 13A-17, each of the plurality of axially extending elements may follow a path that is substantially parallel with a longitudinal axis of the expandable scaffold.

In any of the embodiments in FIGS. 13A-17, each of the plurality of axially extending elements may be continuous and axially extending over at least 55% of a length of the expandable scaffold, optionally over at least 60%, optionally over at least 65%, optionally over at least 70%, optionally over at least 75%, optionally over at least 80%, optionally over at least 85%, optionally over at least 90, optionally over at least 95.

In any of the scaffolds shown in FIGS. 13A-17, all of the connectors in all of the sets of the plurality of sets of connectors may have the same configuration. In any of the scaffolds shown in FIGS. 13A-17, all of the connectors in all of the sets of the plurality of sets of connectors may not have the same configuration. In any of the scaffolds shown in FIGS. 13A-17, each individual set of connectors may have a plurality of connectors that have the same configuration. In any of the embodiments in FIGS. 13A-17, all of the connectors in all of the sets of the plurality of sets of connectors may have an S-shape. In any of the embodiments in FIGS. 13A-17, all of the connectors in all of the sets of the plurality of sets of connectors may have a reverse (or inverted) S-shape. In any of the scaffolds shown in FIGS. 13A-17, all of the connectors in a first set of connectors may have a S shape. In any of the scaffolds shown in FIGS. 13A-17, a second set of connectors that is circumferentially adjacent to the first set of connectors may all have an inverted S shape. In any of the scaffolds shown in FIGS. 13A-17, S shape/inverted S shape connectors may alternate around the circumference of the expandable scaffold.

In any of the embodiments in FIGS. 13A-17, a first set of connectors that extend in a first circumferential direction from a first axially extending element may extend from the first axially extending element at axial locations that are different from the axial locations at which a second set of connectors extend from the first axially extending element in a second circumferential direction (i.e., the connectors have ends that are axially offset).

In any of the embodiments in FIGS. 13A-17, the expandable scaffold may include a transition region connecting a first axially extending element with a strut, optionally wherein the transition region is considered part of the expandable scaffold. A transition region may also connect the strut with a second axially extending element, the second axially being circumferentially adjacent to the first axially extending around the blood conduit. In any of the scaffolds shown in FIGS. 13A-17, the expandable scaffold may extend along substantially the entire length of the conduit. In any of the scaffolds shown in FIGS. 13A-17, the expandable scaffold may extend along less than 50% of the length of the expandable impeller housing. In any of the embodiments in FIGS. 13A-17, the expandable scaffold may extend only in a region of the expandable housing in which an impeller is disposed.

In any of the embodiments in FIGS. 13A-17, the expandable impeller housing may include a second expandable scaffold axially spaced from the first expandable scaffold. A second expandable scaffold may have an expanded configuration with a second plurality of axially extending elements that are axially extending over at least 50% of a length of the second expandable scaffold and wherein the second expandable scaffold may also include a plurality of sets of connectors, each set of connectors extending circumferentially between first and second circumferentially adjacent axially extending elements. A second expandable scaffold may include any features set forth in any of the claims or described elsewhere herein. In any of the scaffolds shown in FIGS. 13A-17, the expandable scaffold may be unitary, that is, made from a single piece of starting material.

Figure 18A:
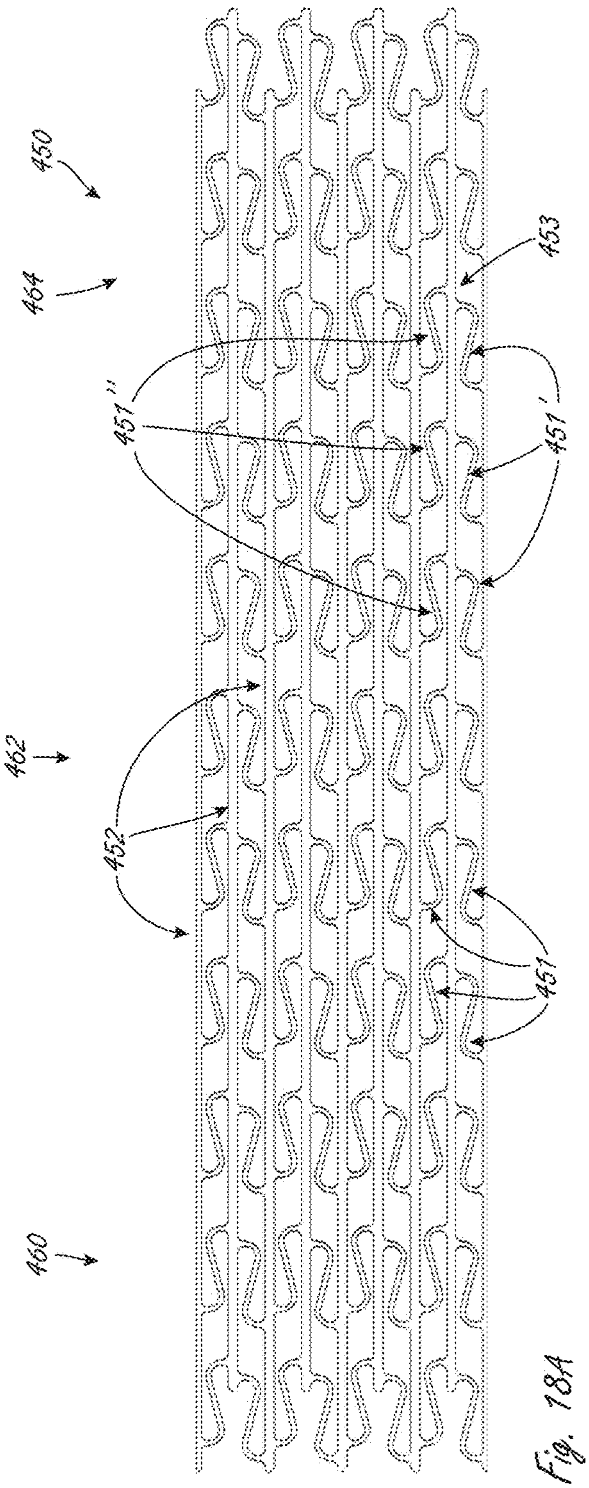
FIG. 18A illustrates an exemplary scaffold in a flattened and non-expanded configuration.
Figure 18B:
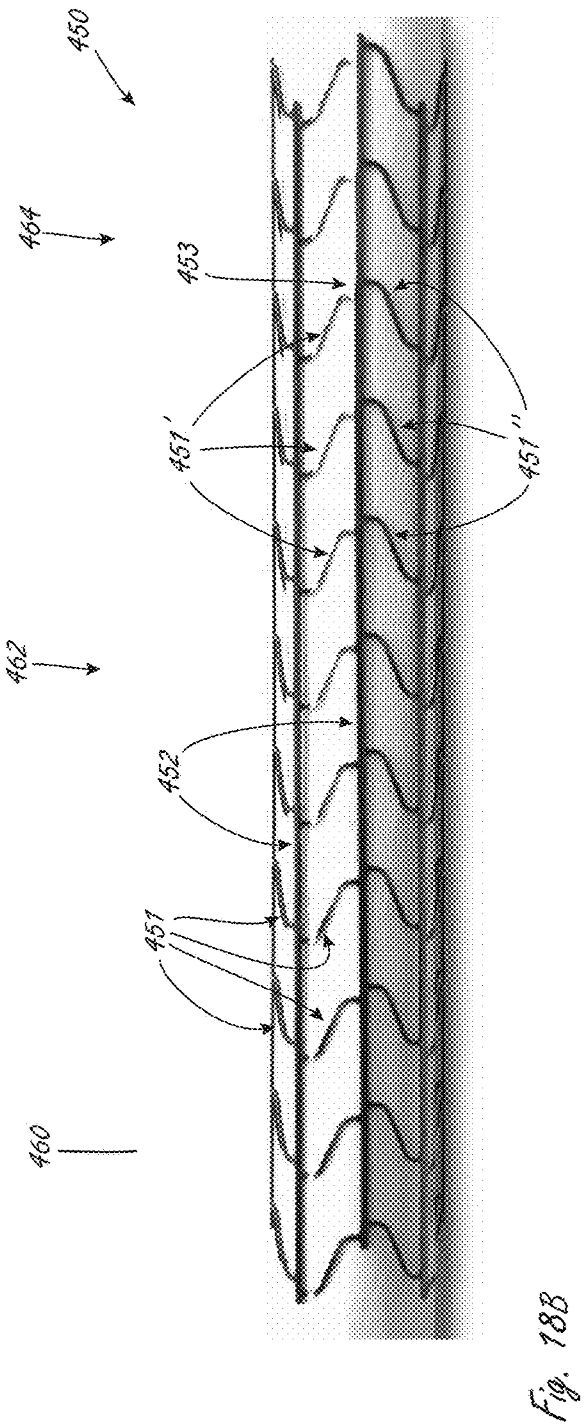
FIG. 18B illustrates the scaffold from FIG. 18A in an expanded configuration.

FIGS. 18A and 18B illustrate an exemplary scaffold 450 comprising a plurality of axially extending elements 452 (eight in this example). Scaffold 450 includes a proximal scaffold 460, a central scaffold 462, and distal scaffold 464. In this example axially extending elements 452 are linear. Central scaffold 462 is connected to proximal scaffold 460 and to distal scaffold 464 in this example, and in particular, is unitary with them in this example. FIG. 18B illustrates an expanded configuration, and FIG. 18A illustrates an as-cut flat illustration of the scaffold. The axially extending elements 452 that are labeled in FIG. 18B are circumferentially adjacent axial elements. Adjacent axially extending elements are connected by a plurality of circumferential connectors 451, which in this example have general S or inverse-S configurations, which include at least one bend formed therein. As shown, each circumferential connector is circumferentially adjacent to another circumferential connectors, and together they extend around the blood conduit. In this example, as shown, circumferentially adjacent circumferential connectors are displaced axially relative to one another. For example, circumferential connectors 451' are axially displaced (or axially offset) relative to circumferential connectors 451". Axially displaced or axially offset in this context refers to proximal ends of the connectors being axially offset, distal ends of the connectors being axially offset, or both. In this example, a section of each one of the axially extending elements connects adjacent circumferential connectors that are axially displaced. For example, section 453 of one of the axially extending elements 452 connects circumferential connector 451' and 451", which creates the axially displaced nature of the circumferentially adjacent circumferential connectors. In this example, distal ends of connectors 451" are further distally than the distal ends of the circumferentially adjacent connectors 451', as shown. FIGS. 18A and 18B also illustrate a first group of a plurality of circumferential connectors having a first axial position, and a second group of the plurality of circumferential connectors having a second axial position, wherein the first and second axial positions alternate circumferentially around the blood conduit, as shown.

Figure 19A:
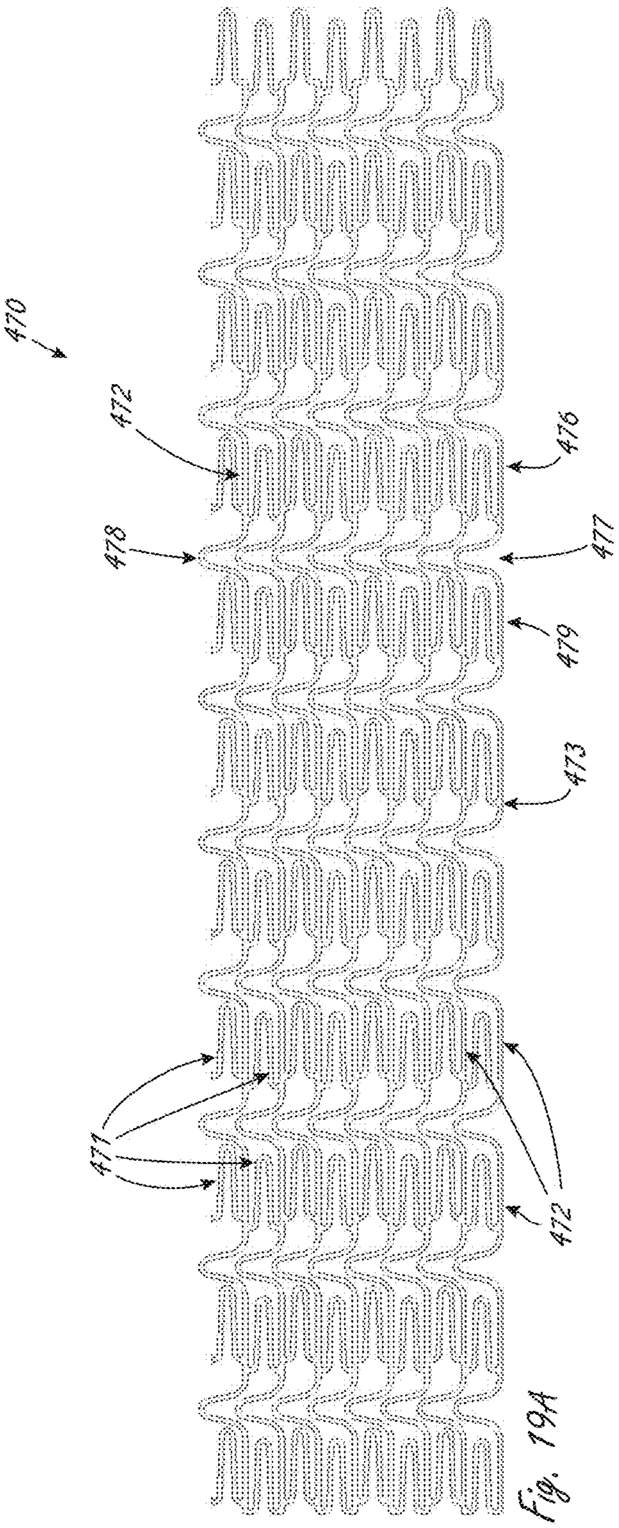
FIG. 19A illustrates an exemplary scaffold in a flattened and non-expanded configuration.
Figure 19B:
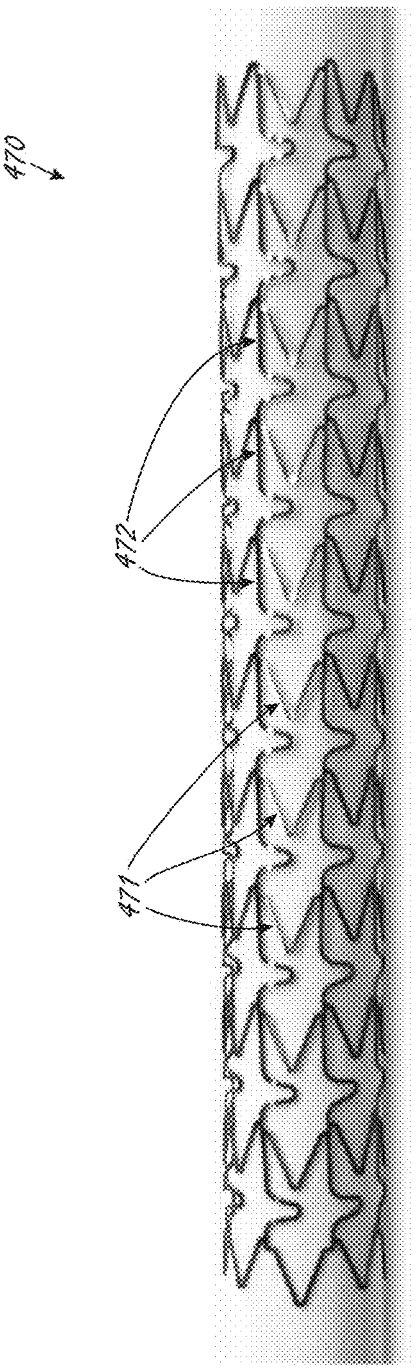
FIG. 19B illustrates the scaffold from FIG. 19A in an expanded configuration.

FIGS. 19A and 19B illustrate an exemplary scaffold 470. Scaffold 470 includes a plurality of axially extending elements 472, which are linear is sections but are not linear along the entire scaffold 470 length. Scaffold 470 also includes connectors 471 that circumferentially connect circumferentially adjacent axial elements 472. Connectors 471 includes peaks that are oriented, or point, axially, and in this example may be oriented distally or proximally Scaffold 470 includes a proximal scaffold, a central scaffold, and a distal scaffold that are connected, and in this example are unitary, just as with the scaffold in FIGS. 18A and 18B. Both the proximal scaffold, central scaffold, and distal scaffold comprise a plurality of linear axially extending elements spaced apart around the blood conduit, wherein first and second adjacent linear axially extending elements are each connected by a circumferential connector having at least one bend formed therein. The circumferential connectors defining a plurality of circumferential connectors around the blood conduit, and wherein circumferentially adjacent circumferential connectors of the plurality of circumferential connectors are displaced axially relative to one another. Like in FIGS. 18A and 19B, a section 473 of each one of the axially extending elements (in this example linear) connects circumferentially adjacent circumferential connectors that are axially displaced, as shown. FIGS. 19A and 19B illustrate a first group of a plurality of circumferential connectors having a first axial position, and wherein a second group of the plurality of circumferential connectors have a second axial position, wherein the first and second axial positions alternate circumferentially around the blood conduit. In this embodiment, the proximal, central, and distal scaffolds are generally have the same configuration (except the ends of the distal and proximal scaffolds).

Scaffold 470 also includes second region 477 that is axially adjacent first region 476, wherein second region 477 comprises a plurality of peaks 478 that are shown oriented orthogonally relative to a long axis of the blood conduit (membrane not shown for clarity). In this example, each of the plurality of peaks 478 is an extension of one of the axially extending elements 472 in the first region 476, as shown. Scaffold 470 also includes third region 479 that is axially adjacent second region 477, the third region 470 comprising a second plurality of linear axially extending elements as shown that are spaced apart around the blood conduit, and a second plurality of circumferential connectors 471, where the second region 477 joins the first region 476 and third region 479. In this example this pattern continues along the length of the scaffold.

Figure 20A:
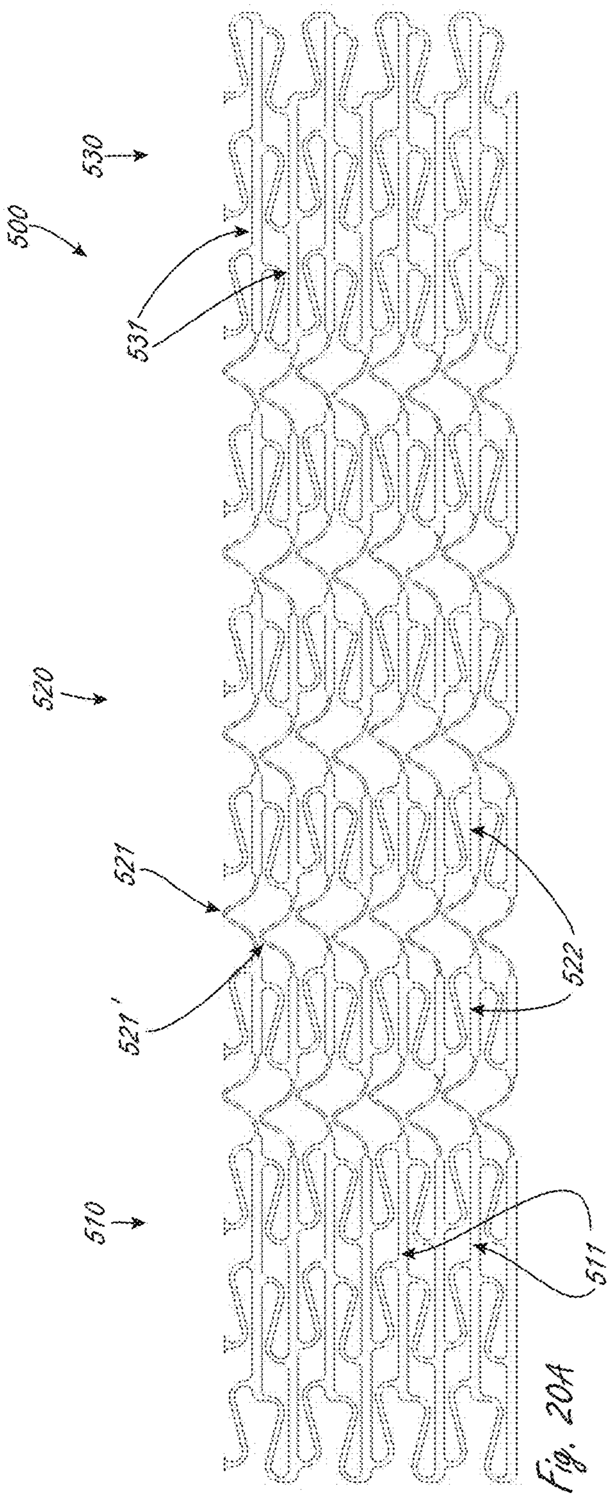
FIG. 20A illustrates an exemplary scaffold in a flattened and non-expanded configuration.
Figure 20B:
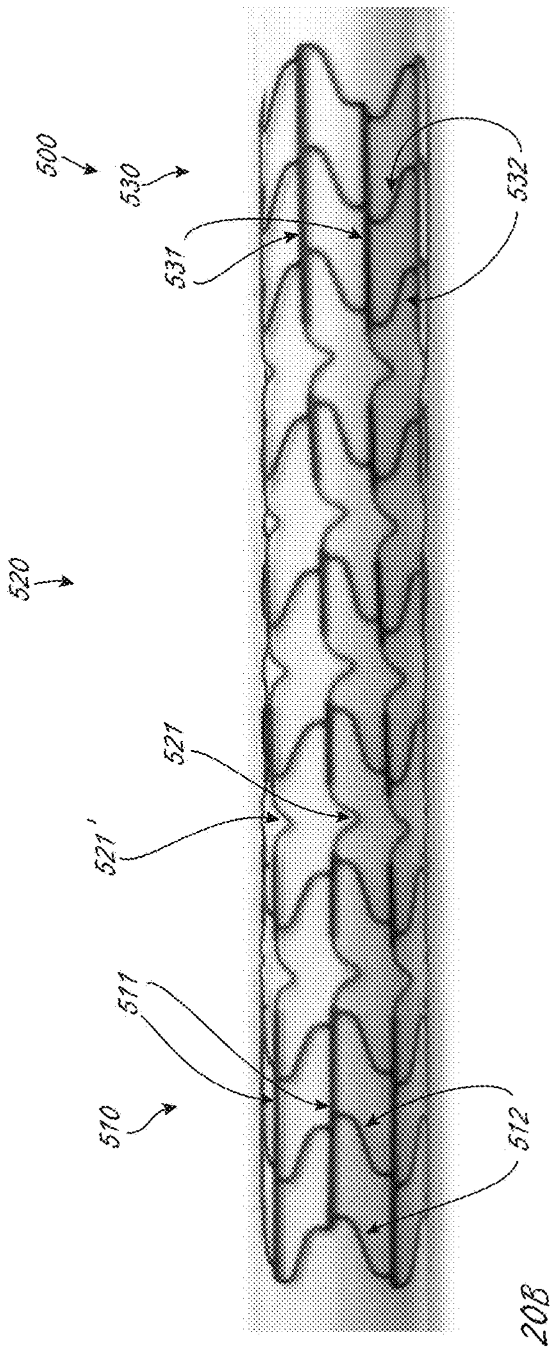
FIG. 20B illustrates the scaffold from FIG. 20A in an expanded configuration.

FIGS. 20A and 20B illustrate exemplary scaffold 500, with FIG. 20B showing the expanded configuration and FIG. 20A illustrating a flattened non-expanded configuration. Features that are shown in FIGS. 20A and 20B that are the same as features shown in other scaffolds herein may be expressly included in this embodiment even if not described herewith. Scaffold 500 includes proximal scaffold 510, central scaffold 520 and distal scaffold 530, which are unitary in this embodiment. In this embodiment the central scaffold 520 has a pattern and configuration such that it is less stiff in response to a radially inward force than proximal scaffold 510 and distal scaffold 530. Proximal scaffold 510 may be a proximal impeller scaffold, and distal scaffold 530 may be a distal impeller scaffold, within at least a portion of which a proximal impeller and a distal impeller may be disposed, respectively. Scaffold 500 central scaffold 520 has a pattern that is different than the pattern in scaffold sections 510 and 530. In this example, scaffold sections 510 and 530 have patterns that are substantially the same. Scaffold 500 includes circumferential connectors in proximal scaffold 510, central scaffold 520, and distal scaffold 530, as shown. For example, proximal scaffold 510 includes circumferential connectors 512, and distal scaffold 530 includes circumferential connectors 532. The circumferential connectors in scaffold 500 have the same configurations as circumferential connectors 451 in the scaffold 450 in FIGS. 18A and 18B, and all descriptions thereof are incorporated by reference with the circumferential connectors into all scaffold sections in scaffold 500. For example only, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. The central scaffold 520 in scaffold 500 also includes peaks 521 and 521', similar to peaks 478 in the scaffold in FIGS. 19A and 19B. A first plurality of peaks 521 have a first axial position, and a second plurality of peaks 521' have a second axial position, which can be seen clearly in FIG. 20A. The axial position alternates circumferentially around the scaffold, as shown. Peaks 521 and 521' extend from axially extending elements 522 like the scaffold in FIGS. 19A and 19B. The proximal scaffold and the distal scaffold do not include peaks in this embodiment. Axially extending elements 522 in the central scaffold section have a width that is greater than the width of the scaffold in peak 521 regions, as shown. This difference in width can provide the peak regions with greater flexibility, while the wider axially extending element provide sufficient radial support in the central scaffold. Any of the scaffold sections with the peaks may be considered a first region, and the axially adjacent sections with circumferential connectors and axially extending elements may be considered second regions, examples of which are described elsewhere herein. In this embodiment the axially extending elements are linear as shown, but may be curvilinear in other embodiments.

Figure 21A:
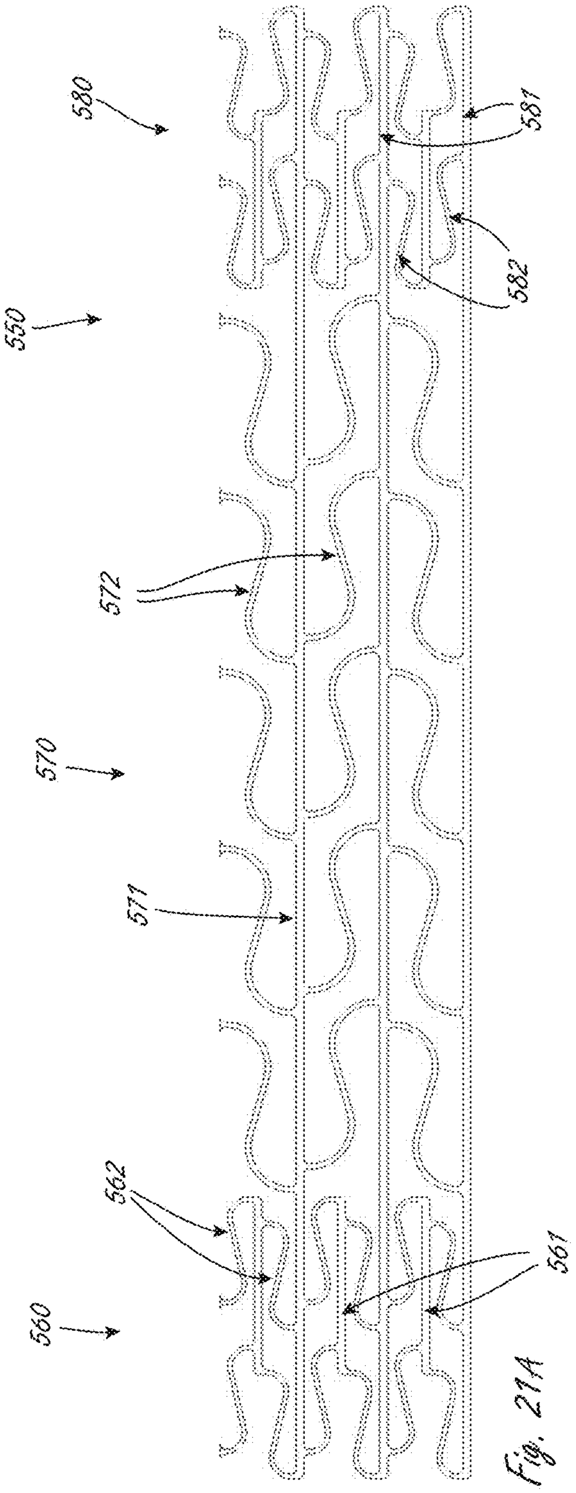
FIG. 21A illustrates an exemplary scaffold in a flattened and non-expanded configuration.
Figure 21B:
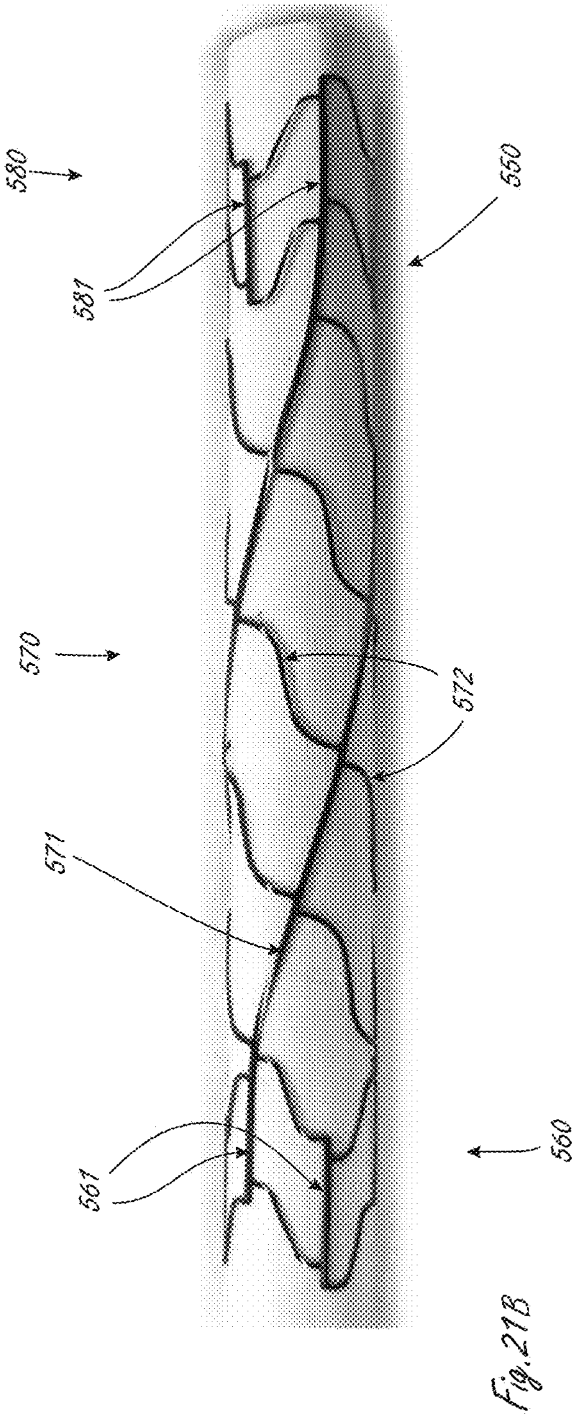
FIG. 21B illustrates the scaffold from FIG. 21A in an expanded configuration.

FIGS. 21A and 21B illustrate exemplary scaffold 550, with FIG. 21B showing the expanded configuration and FIG. 21A illustrating a flattened non-expanded configuration. Features that are shown in FIGS. 21A and 21B that are the same as features shown in other scaffolds herein may be expressly included in this embodiment even if not described herewith. Scaffold 550 includes proximal scaffold 560, central scaffold 570 and distal scaffold 580, which are unitary in this embodiment. Proximal scaffold 560 may be a proximal impeller scaffold, and distal scaffold 580 may be a distal impeller scaffold, within at least a portion of which a proximal impeller and a distal impeller may be disposed, respectively. Scaffold 550 central scaffold 570 has a pattern that is different than the pattern in scaffold sections 560 and 580. In this example, scaffold sections 560 and 580 have patterns that are substantially the same. Scaffold 550 includes circumferential connectors in proximal scaffold 560, central scaffold 570, and distal scaffold 580, as shown. For example, proximal scaffold 560 includes circumferential connectors 562, and distal scaffold 580 includes circumferential connectors 582. The circumferential connectors in scaffold 550 have the same configurations as circumferential connectors 451 in the scaffold 450 in FIGS. 18A and 18B, and all descriptions thereof are incorporated by reference with the circumferential connectors into all scaffold sections in scaffold 550. For example only, circumferentially adjacent circumferential connectors are axially displaced (i.e., axially offset) relative to one another, which is described in more detail elsewhere herein. The circumferential connectors also have the S and inverse-S configurations, which is described with respect to other scaffolds herein. Elements 571 in the central scaffold extend into the proximal and distal scaffold sections as shown, forming linear axially extending elements in the proximal and distal scaffolds. Axially extending elements 561 in proximal scaffold 560 do not extend into the central scaffold, as shown. Similarly, axially extending elements 581 in distal scaffold 580 do not extend into the central scaffold, as shown. Elements 571 in the central scaffold 570 have helical configurations as shown. Adjacent elements 571 are connected with connectors 572 as shown. Connectors 572 may have any characteristics of any circumferential connectors herein, such as the alternating S and inverse-S configurations. FIG. 21A illustrates a flattened non-expanded configuration, and the scaffold 550 may be formed into the configuration shown in FIG. 21B, such as by twisting the ends relative to one another and setting the scaffold in the configuration shown in FIG. 21B.

Figure 22A:
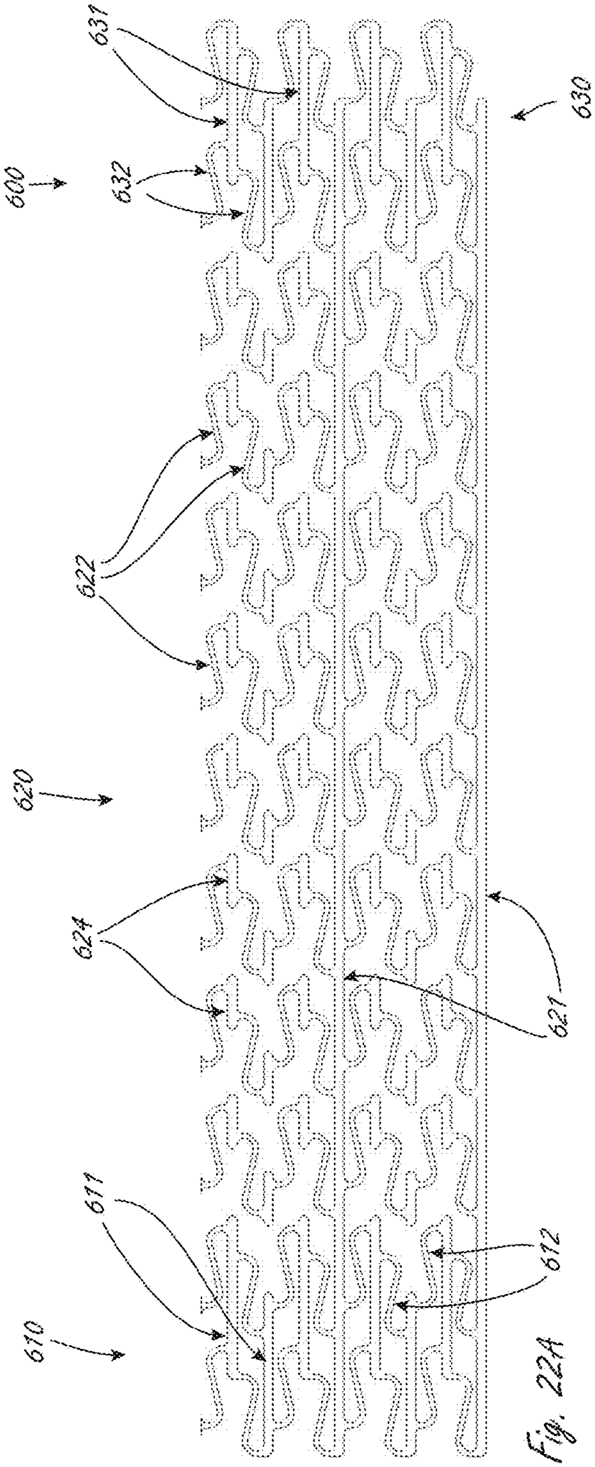
FIG. 22A illustrates an exemplary scaffold in a flattened and non-expanded configuration.
Figure 22B:
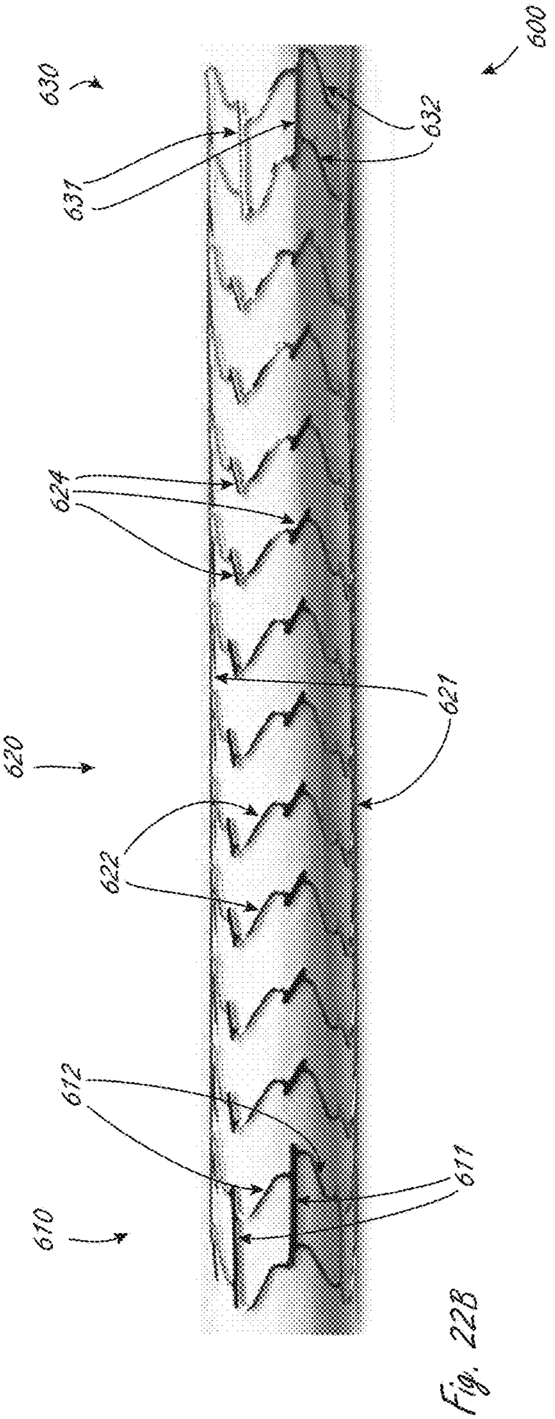
FIG. 22B illustrates the scaffold from FIG. 22A in an expanded configuration.

FIGS. 22A and 22B illustrate exemplary scaffold 600, with FIG. 22B showing the expanded configuration and FIG. 22A illustrating a flattened non-expanded configuration. Features that are shown in FIGS. 22A and 22B that are the same as features shown in other scaffolds herein may be expressly included in this embodiment even if not described herewith. Scaffold 600 includes proximal scaffold 610, central scaffold 620 and distal scaffold 630, which are unitary in this embodiment. Proximal scaffold 610 may be a proximal impeller scaffold, and distal scaffold 630 may be a distal impeller scaffold, within at least a portion of which a proximal impeller and a distal impeller may be disposed, respectively. Scaffold 600 central scaffold 620 has a pattern that is different than the pattern in scaffold sections 610 and 630. In this example, scaffold sections 610 and 630 have patterns that are substantially the same. Scaffold 600 includes circumferential connectors in proximal scaffold 610, central scaffold 620, and distal scaffold 630, as shown. For example, proximal scaffold 610 includes circumferential connectors 612, and distal scaffold 630 includes circumferential connectors 632. The circumferential connectors in the proximal and distal sections of scaffold 600 have the same configurations as circumferential connectors 451 in the scaffold 450 in FIGS. 18A and 18B, and all descriptions thereof are incorporated by reference with the circumferential connectors into all scaffold sections in scaffold 600. For example only, circumferentially adjacent circumferential connectors are axially displaced (i.e., axially offset) relative to one another, which is described in more detail elsewhere herein, and connect axially extending elements 611 and 631, respectively. The circumferential connectors also have S and inverse-S configurations, which is described with respect to other scaffolds herein. Axially extending elements 621 in the central scaffold extend into the proximal and distal scaffold sections as shown, wherein the elements 621 are linear axially extending elements in the proximal and distal scaffolds as well as the central scaffold. Axially extending elements 611 in proximal scaffold 610 do not extend into the central scaffold, as shown. Similarly, axially extending elements 631 in distal scaffold 630 do not extend into the central scaffold, as shown. Elements 621 in the central scaffold 620 have axially extending linear configurations as shown. Central scaffold 620 includes axially extending elements 621 that are connected by circumferential connectors. The circumferential connectors include a plurality of axially extending elements 624, each of which connect circumferentially adjacent circumferential connectors 622, as shown. When scaffold 600 is expanded to the configuration shown in FIG. 22B, the circumferential connectors assume the configuration shown, wherein elements 624 are no longer purely axially extending, such that they form an angle with a long axis of the scaffold, as shown.

FIGS. 23A and 23B illustrate exemplary scaffold 650, with FIG. 23B showing the expanded configuration and FIG. 23A illustrating a flattened non-expanded configuration. Features that are shown in FIGS. 23A and 23B that are the same as features shown in other scaffolds herein may be expressly included in this embodiment even if not described herewith. Scaffold 650 includes proximal scaffold 660, central scaffold 670 and distal scaffold 650, which are unitary in this embodiment. Proximal scaffold 660 may be a proximal impeller scaffold, and distal scaffold 650 may be a distal impeller scaffold, within at least a portion of which a proximal impeller and a distal impeller may be disposed, respectively. Scaffold 650 central scaffold 670 has a pattern that is different than the pattern in scaffold sections 660 and 680. In this example, scaffold sections 660 and 680 have patterns that are substantially the same. Scaffold 650 includes circumferential connectors in proximal scaffold 660, central scaffold 670, and distal scaffold 680, as shown. For example, proximal scaffold 660 includes circumferential connectors 662, and distal scaffold 650 includes circumferential connectors 682. The circumferential connectors in the proximal and distal sections of scaffold 650 have the same configurations as circumferential connectors 451 in the scaffold 450 in FIGS. 18A and 18B, and all descriptions thereof are incorporated by reference with the circumferential connectors into all scaffold sections in scaffold 650. For example only, circumferentially adjacent circumferential connectors are axially displaced (i.e., axially offset) relative to one another, which is described in more detail elsewhere herein, and connect axially extending elements 661 and 681, respectively. The circumferential connectors also have S and inverse-S configurations, which is described with respect to other scaffolds herein. Axially extending elements 671 in the central scaffold extend into the proximal and distal scaffold sections as shown, wherein the elements 671 are linear axially extending elements in the proximal and distal scaffolds as well as the central scaffold. Axially extending elements 661 in proximal scaffold 660 do not extend into the central scaffold, as shown. Similarly, axially extending elements 681 in distal scaffold 650 do not extend into the central scaffold, as shown. Elements 671 in the central scaffold 670 have axially extending linear configurations as shown. Central scaffold 670 includes axially extending elements 671 that are connected by circumferential connectors. The circumferential connectors include a plurality of axially extending elements 674, each of which connect circumferentially adjacent circumferential connectors 672, as shown. When scaffold 650 is expanded to the configuration shown in FIG. 23B, the circumferential connectors 672 assume the configuration shown, wherein elements 674 are no longer purely axially extending, such that they form an angle with a long axis of the scaffold, as shown. Elements 674 in FIG. 23A are formed by removing material axially disposed between axially adjacent elements 674.

Figure 24A:
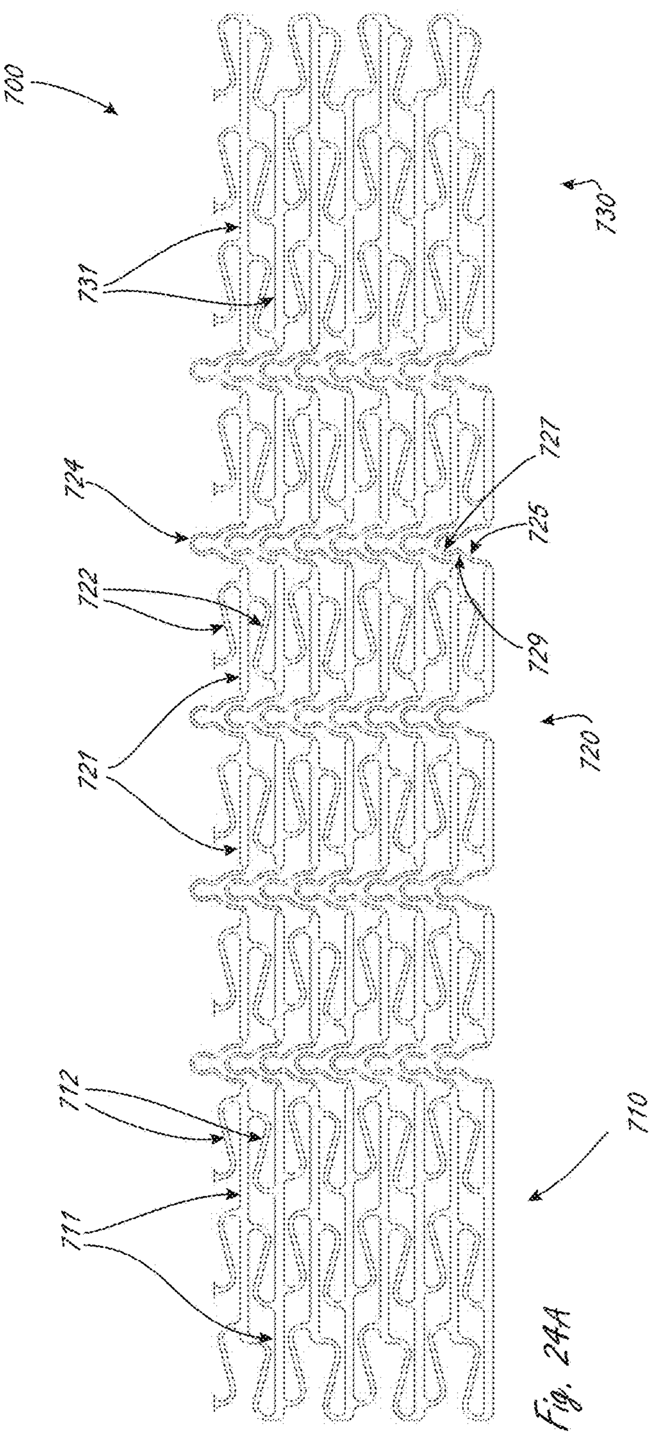
FIG. 24A illustrates an exemplary scaffold in a flattened and non-expanded configuration.
Figure 24B:
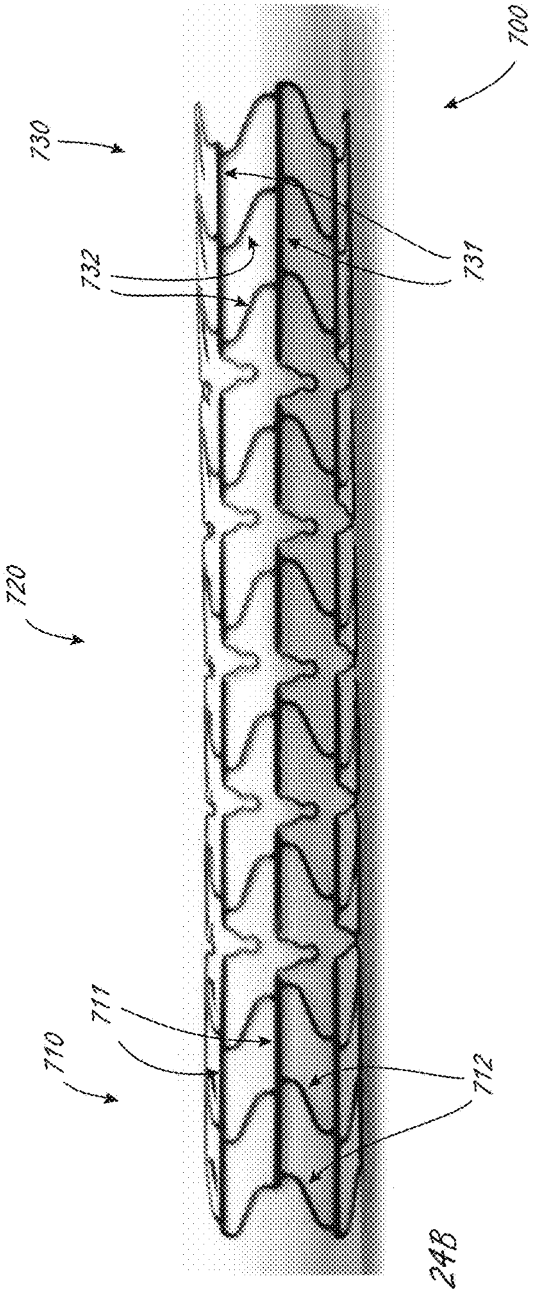
FIG. 24B illustrates the scaffold from FIG. 24A in an expanded configuration.

FIGS. 24A and 24B illustrate exemplary scaffold 700, with FIG. 24B showing the expanded configuration and FIG. 24A illustrating a flattened non-expanded configuration. Features that are shown in FIGS. 24A and 24B that are the same as features shown in other scaffolds herein may be expressly included in this embodiment even if not described herewith. For example, scaffold 700 is the same in some ways to the scaffolds shown in FIGS. 19A, 19B, 20A and 20B. Scaffold 700 includes proximal scaffold 710, central scaffold 720 and distal scaffold 730, which are unitary in this embodiment. Proximal scaffold 710 may be a proximal impeller scaffold, and distal scaffold 730 may be a distal impeller scaffold, within at least a portion of which a proximal impeller and a distal impeller may be disposed, respectively. Scaffold 700 central scaffold 720 has a pattern that is different than the pattern in scaffold sections 710 and 730. In this example, scaffold sections 710 and 730 have patterns that are substantially the same. Scaffold 700 includes circumferential connectors in proximal scaffold 710, in central scaffold 720, and in distal scaffold 730, as shown. For example, proximal scaffold 710 includes circumferential connectors 712, and distal scaffold 730 includes circumferential connectors 732. The circumferential connectors in the proximal and distal sections of scaffold 700 have the same configurations as circumferential connectors 451 in the scaffold 450 in FIGS. 18A and 18B, and all descriptions thereof are incorporated by reference with the circumferential connectors into all scaffold sections in scaffold 700. For example only, circumferentially adjacent circumferential connectors are axially displaced (i.e., axially offset) relative to one another, which is described in more detail elsewhere herein, and connect axially extending elements 711 and 731, respectively. The circumferential connectors also have S and inverse-S configurations alternating circumferentially around the scaffold, which is described with respect to other scaffolds herein. Scaffold 700 includes a plurality of axially extending elements 711, which are linear in sections but do not extend along the entire length of scaffold 700. Scaffold 700 also includes circumferential connectors 712 that circumferentially connect circumferentially adjacent axial elements 711. The proximal scaffold, central scaffold, and distal scaffold comprise a plurality of linear axially extending elements 711, 721, and 731, respectively, that are circumferentially spaced apart around the respective scaffold section, wherein first and second adjacent linear axially extending elements are each connected by a circumferential connector 712, 722, and 732, respectively, having at least one bend formed therein. The circumferential connectors define a plurality of circumferential connectors around the scaffold, and wherein circumferentially adjacent circumferential connectors of the plurality of circumferential connectors are displaced axially relative to one another, as shown and described elsewhere herein. As is the case in FIGS. 18A and 19B, a section of each one of the axially extending elements (in this example linear elements) connects circumferentially adjacent circumferential connectors that are axially displaced, as shown. FIGS. 24A and 24B illustrate a first group of a plurality of circumferential connectors having a first axial position, and wherein a second group of the plurality of circumferential connectors have a second axial position, wherein the first and second axial positions alternate circumferentially around the scaffold.

Scaffold 700 also includes a second region that is axially adjacent a first region, wherein the second region comprises a plurality of peaks 724 that are shown oriented orthogonally relative to a long axis of the scaffold 700. In this example, each of the plurality of peaks 724 is an extension of one of the axially extending elements 721, as shown. Scaffold 700 also includes a third region that is axially adjacent the second region, the third region comprising a second plurality of linear axially extending elements as shown that are spaced apart around the scaffold, and a second plurality of circumferential connectors 722, where the second region joins the first region and third region. In this embodiment, the second region includes first convex section 725 and second convex section 727, connected at location 729.

Figure 25A:
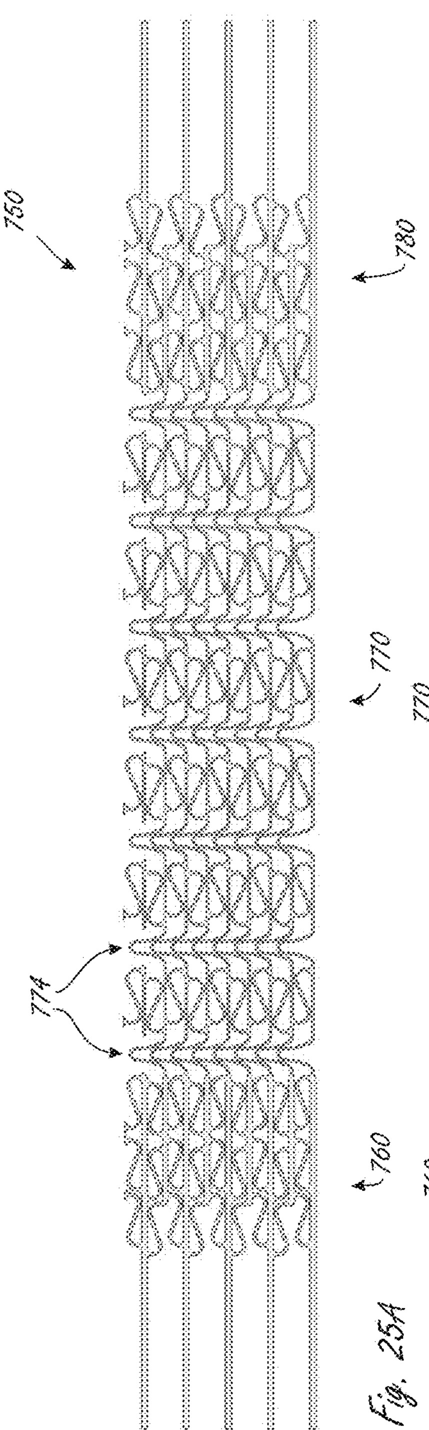
FIG. 25A illustrates an exemplary scaffold in a flattened and non-expanded configuration.
Figure 25B:
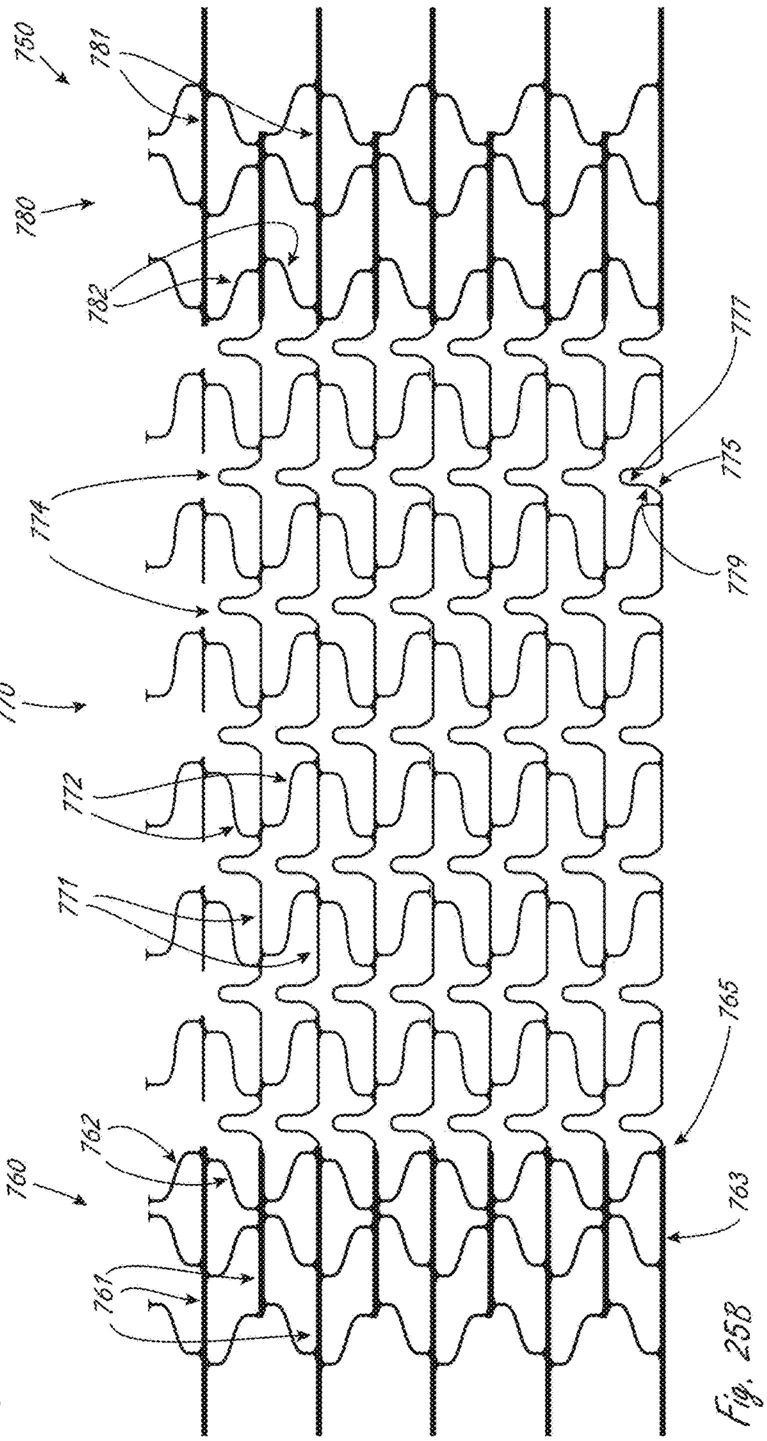
FIG. 25B illustrates the scaffold from FIG. 25A in an flattened expanded configuration.

FIGS. 25A and 25B illustrate an exemplary scaffold 750, which in this example includes a proximal scaffold 760, central scaffold 770 and distal scaffold 780, which are unitary. Scaffold 750 is similar in several ways to scaffold 700 in FIGS. 24A and 24B, the disclosure of which is completely incorporated by reference in the description of FIGS. 25A and 25B, any features of which may be included in scaffold 750. One difference is that scaffold 750 central scaffold 770 includes a first region that includes peaks 774, wherein the first region includes sections 775 and 777 connected at location 779, wherein sections 775 and 777 create a smoother curvilinear region than sections 725 and 727 in scaffold 700. An additional difference is that scaffold 750 includes proximal and distal scaffolds that both include mirrored sections, such as sections 763 and 765 as shown in FIG. 25B. The mirrored aspect refers to axially adjacent connectors 762 in section 763 that are mirrored with respect to connectors 762 in section 765. The same mirrored aspect is shown in distal scaffold 780. The mirrored sections in proximal scaffold 760 are closer to central scaffold 770 than the mirrored sections in distal scaffold 780, as shown. In alternative embodiments, mirrored sections in a distal scaffold may be closer to a central scaffold than mirrored sections in a proximal scaffold. The description of all other aspects of scaffolds herein, including axially extending elements (761, 771, 781) and circumferential connectors (762, 772, 782), are incorporated by reference herein into the scaffold 750. FIG. 25B shows a flat expanded configuration, while FIG. 25A shows a flat non-expanded configuration.

Figure 26A:
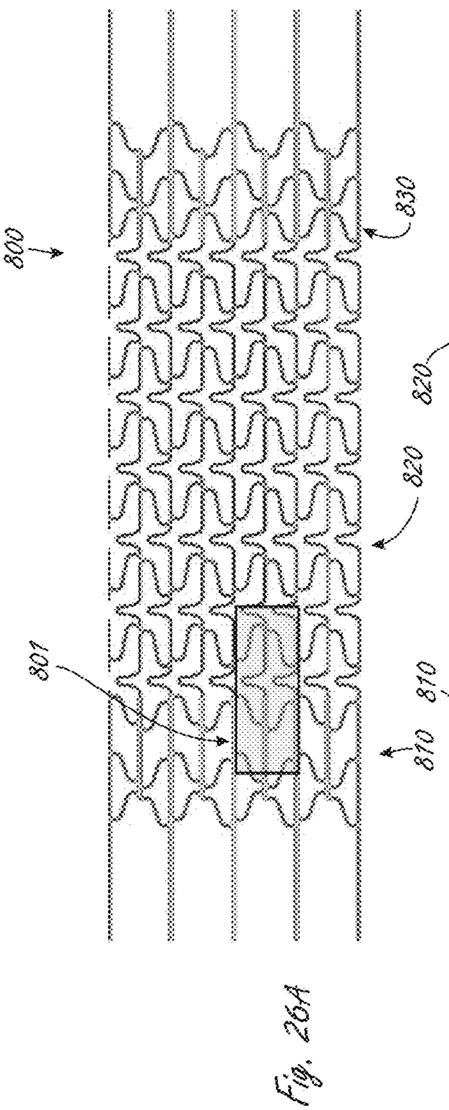
FIG. 26A illustrates an exemplary scaffold in a flattened and non-expanded configuration.
Figure 26B:
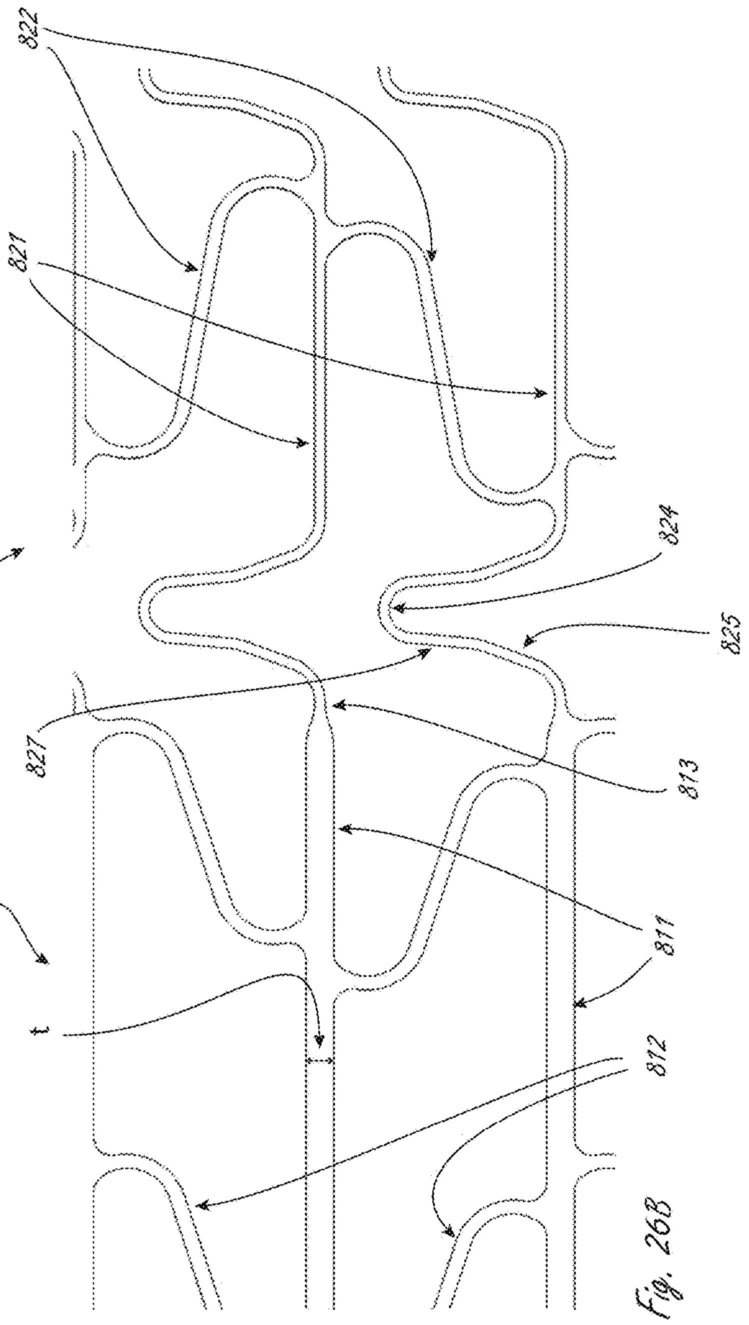
FIG. 26B highlights an exemplary section of the scaffold shown in FIG. 26A.

FIGS. 26A and 26B illustrate scaffold 800, which as shown includes many of the same features as scaffold 750 shown in FIGS. 25A and 25B. FIG. 26A illustrate a flattened unexpanded configuration, while FIG. 26B illustrates transition region 801 of scaffold 800 called out in FIG. 26A. A difference between the scaffolds is that in FIGS. 26A and 26B, proximal scaffold 810 includes mirrored sections that are further from central scaffold 820 than mirrored section in distal scaffold, as shown. FIG. 26B illustrates a transition region between proximal scaffold 810 and central scaffold 820. Scaffold 800 includes orthogonally oriented peaks 824 as described elsewhere herein. Scaffold first regions includes sections 825 and 827, which may be the same as sections 775 and 777 in scaffold 750. FIG. 26B illustrates the widths of axially extending elements 811 being greater than the widths of elements 821 in central scaffold, as shown. The thickness measurements are into the page in the figures (in the "z" direction), while the width measurements are in the plane of the page in the figures shown. One thickness "t" of element 811 is labeled for reference. As shown, the thickness "t" of element 811 is greater than the thickness of elements 821 in the central scaffold section.

Figure 27A:
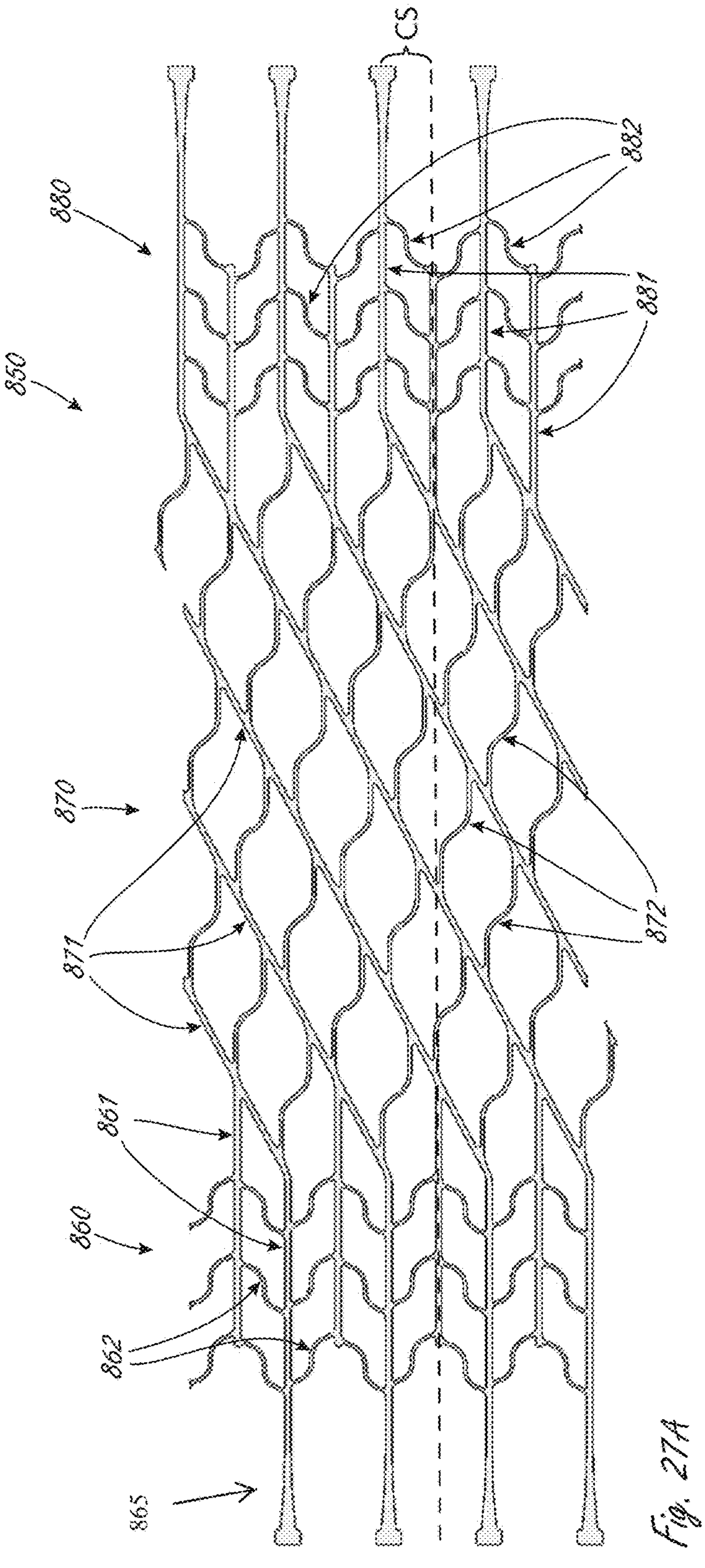
FIG. 27A illustrates an exemplary scaffold in a flattened and non-collapsed configuration.
Figure 27B:
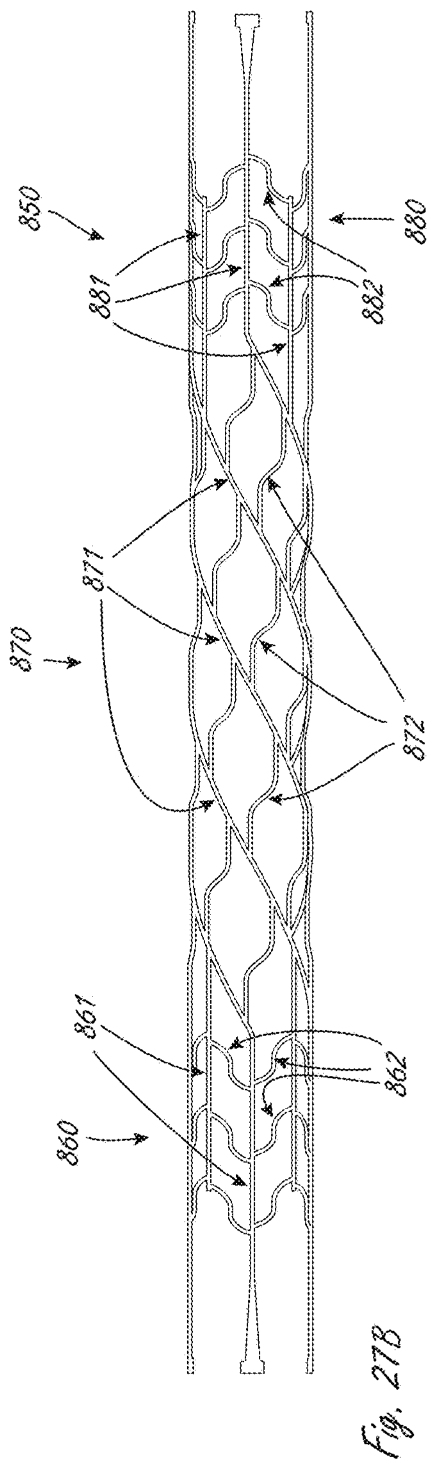
FIG. 27B illustrates the scaffold from FIG. 27A in a non-collapsed configuration.

FIGS. 27A and 27B illustrate exemplary scaffold 850, which is similar in several ways to scaffold 550 shown in FIGS. 21A and 21B. Scaffold 850 includes proximal scaffold 860, central scaffold 870 and distal scaffold 880, which in this embodiment may be unitary. Scaffold 850 central scaffold 870 includes helical elements 871 in the non-collapsed configuration (FIG. 27A) and the wrapped configuration (FIG. 27B). In this and any other embodiment herein the scaffold may be manufactured (e.g., including laser cutting of a tubular member) such that the expanded configuration is the configuration is which the scaffold is laser-cut from the tubular member. This is in contrast to any examples herein in which the scaffold is laser cut from a smaller diameter tubular member, and then expanded and set into an expanded configuration. In any of the embodiments herein, a laser cut diameter may be equal to a non-collapsed diameter to, for example without limitation, provide better concentricity. This may also allow coating of a membrane to adhere to struts and have a smoother inner diameter.

Proximal scaffold 860 and distal scaffold 880 have substantial the same configuration, but they are displaced circumferentially by circumferential spacing "CS" (labeled in FIG. 27A). Adjacent helical elements 871 are connected by connectors 872. All other similar aspect of other scaffolds herein may be incorporated herein, including, by way of example only, axially extending elements (861, 881) and the axially offset nature of circumferentially adjacent circumferential connectors (862, 882) in proximal scaffold 860 and distal scaffold 880.

FIG. 27A illustrates exemplary distal and proximal struts extending axially from the scaffold, only one strut of which 865 is labeled. In this example there are four proximal and four distal struts. As shown, the struts are tapered and are wider at ends further from the scaffold, which may increase stability over the impellers compared to struts that have a constant width over their entire length. Any of the pump portions herein may include any number of struts that have the same configuration as struts 865.

In any of the embodiments herein, the scaffold may be cut from a tubular member that has an expanded scaffold diameter. In these embodiments, the tubular member has a diameter that is the same or substantially the same as the desired scaffold deployed configuration (un-sheathed). Alternatively, in any of the embodiments herein, the scaffold may be cut from a tubular member that has a non-expanded scaffold diameter. In this embodiments, the tubular member has a diameter less than a scaffold expanded diameter, and after being cut the scaffold may be expanded set in the expanded deployed configuration.

In any of the embodiments herein, a distal scaffold may have a length that is greater than a length of a proximal scaffold. In any of the embodiments herein, a distal scaffold may have a length that is less than a length of a proximal scaffold. In any of the embodiments herein, a distal scaffold may have a length that is the same as a length of a proximal scaffold.

In any embodiment herein, a central scaffold may have a length that is greater than a length of one or both of a proximal scaffold and a distal scaffold.

Any of the different scaffold sections herein may be connected with one or more welds, and may not be unitary with each other.

In any of the embodiments herein, any section or sections of the scaffold may have a thickness (measured radially between a scaffold inner diameter and a scaffold outer diameter) that is the same as or different than a thickness of any other section of the scaffold. For example, a thickness of a scaffold section may be decreased by electropolishing one or more sections more than other sections (which may include no electropolishing). Varying the thickness may be in addition to or alternative to varying the width, which may allow for more design options, as may be desired.

In any of the embodiments herein, an axial distance between proximal and distal scaffold sections may be from 30 mm to 50 mm, such as from 35 mm to 45 mm.

In any of the embodiments herein, the pump portion may be from 40 mm and 80 mm, such as from 50 mm to 70 mm, such as from 55 mm to 65 cm.

In any of the embodiments herein that include first and second impellers, an axial distance between impellers may be from 40 mm to 60 mm, such as from 45 mm to 55 mm.

In any of the embodiments herein, a diameter of the expanded (or non-collapsed) blood conduit may be from 6 mm to 8.5 mm, such as from 6 mm to 8 mm, such as from 6.5 mm to 7.5 mm In any of the embodiments herein, a diameter of any of the impellers when expanded may be from 5 mm to 7 mm, such as from 5.5 mm to 6.5 mm

What is claimed is:

1. A catheter blood pump ("blood pump"), comprising:

an expandable pump portion extending distally relative to a catheter, the pump portion including an impeller housing that includes an expandable blood conduit defining a blood lumen, the expandable blood conduit comprising:

a plurality of struts extending distally from the catheter, a proximal impeller scaffold portion extending distally from the plurality of struts, a distal impeller scaffold portion, and a central scaffold portion disposed between the proximal impeller scaffold portion and the distal impeller scaffold portion, the proximal impeller scaffold portion and the distal impeller scaffold portion having a plurality of linear axial elements and a plurality of circumferentially adjacent circumferential connectors, the central scaffold portion having a different configuration than the proximal impeller scaffold portion and the distal impeller scaffold portion and including a plurality of helical elements having a helical configuration between the proximal impeller scaffold portion and the distal impeller scaffold portion, wherein each of the helical elements is an extension of a linear element in at least one of the proximal impeller scaffold portion or the distal impeller scaffold portion, wherein the proximal impeller scaffold portion and the distal impeller scaffold portion do not include helical elements, the central scaffold portion being less stiff in response to a radially inward force than the proximal and distal impeller scaffold portions, and a membrane coupled to the proximal impeller scaffold portion, the central scaffold portion, and the distal impeller scaffold portion, the membrane at least partially defining the blood lumen, and at least one impeller disposed at least partially within at least one of the proximal impeller scaffold portion and the distal impeller scaffold portion.

2. The blood pump of claim 1, wherein the central scaffold portion is connected with at least one of the proximal impeller scaffold portion and the distal impeller scaffold portion.

3. The blood pump of claim 2, wherein the central scaffold portion is connected with the proximal impeller scaffold portion and the distal impeller scaffold portion.

4. The blood pump of claim 3, wherein the central scaffold portion is unitary with the proximal impeller scaffold portion and the distal impeller scaffold portion.

5. The blood pump of claim 3, wherein the central scaffold portion is attached to the proximal impeller scaffold portion and attached to the distal impeller scaffold portion.

6. The blood pump of claim 1, wherein the proximal impeller scaffold portion and the distal impeller scaffold portion have the same or substantially the same configuration.

7. The blood pump of claim 6, wherein a dimension of a first feature of the proximal impeller scaffold portion is different than a corresponding feature of the distal impeller scaffold portion.

8. The blood pump of claim 1, wherein the proximal impeller scaffold portion and the distal impeller scaffold portion have different configurations.

9. The blood pump of any of claims 1-5, wherein the distal impeller scaffold portion has a length that is greater than a length of the proximal impeller scaffold portion.

10. The blood pump of any of claims 1-5, wherein a width dimension of the helical elements is less than a width dimension of the plurality of linear axial elements.

11. The blood pump of claim 1, wherein the plurality of linear axial elements are spaced apart around the blood conduit, wherein first and second adjacent linear axial elements are each connected by a circumferential connector of the plurality of circumferentially adjacent circumferential connectors having at least one bend formed therein, and wherein the plurality of circumferentially adjacent circumferential connectors are displaced axially relative to one another, and wherein each one of the linear axial elements connects adjacent circumferential connectors that are axially displaced.

12. The blood pump of claim 11, wherein a first group of the plurality of circumferential connectors have a first axial position, and wherein a second group of the plurality of circumferential connectors have a second axial position, wherein the first and second axial positions alternate circumferentially around the blood conduit.

13. The blood pump of claim 12, wherein the proximal impeller scaffold portion and the distal impeller scaffold portion each comprise a separate plurality of linear axial elements.

14. The blood pump of claim 1, wherein the at least one impeller extends proximally out of the blood conduit.

15. The blood pump of claim 1, wherein the plurality of helical elements comprises more than two and less than fifteen helical elements.

16. The blood pump of claim 1, wherein the plurality of helical elements consists of four helical elements.

17. The blood pump of claim 1, wherein the proximal scaffold portion and the distal scaffold portion have the same or substantially the same configuration.

18. The blood pump of claim 17, wherein the distal scaffold portion is circumferentially offset relative to the proximal scaffold portion.

19. The blood pump of claim 18, wherein the distal scaffold portion is circumferentially offset between one and 90 degrees relative to the proximal scaffold portion.

20. The blood pump of claim 17, wherein first circumferential members in the distal scaffold portion are closer together than corresponding second circumferential members in the proximal scaffold portion.

21. A catheter blood pump, comprising:

an elongate catheter shaft;

an expandable scaffold extending distally from the elongate catheter shaft, the expandable scaffold comprising:

a plurality of proximal struts coupled to the elongate catheter shaft and defining a blood outlet;

a proximal scaffold portion extending distally from the proximal struts, the proximal scaffold portion including a first plurality of linear axial elements and a first plurality of circumferentially adjacent circumferential connectors, the proximal impeller scaffold portion not including helical elements;

a distal scaffold portion positioned distal to the proximal scaffold portion, the distal scaffold portion including a second plurality of linear axial elements and a second plurality of circumferentially adjacent circumferential connectors, the distal scaffold portion not including helical elements;

a central scaffold portion positioned between the proximal scaffold portion and the distal scaffold portion, the central scaffold portion having a helical configuration that is different than the proximal scaffold portion and the distal scaffold portion, the helical configuration including a plurality of helical elements, wherein each of the plurality of helical elements is an extension of at least one of the first plurality of linear axial elements of the proximal scaffold portion or the second plurality of linear axial elements of the distal scaffold portion, the central scaffold portion being less stiff in response to a radially inward force than the proximal and distal impeller scaffold portions;

a plurality of distal struts extending distally from the distal scaffold portion and defining a blood inlet;

at least one impeller disposed at least partially within at least one of the proximal scaffold portion and the distal scaffold portion; and a membrane coupled to the expandable scaffold and extending from the proximal scaffold portion to the distal scaffold portion, the membrane at least partially defining a blood lumen between the inlet and the outlet.

* * * * *